United States Patent
Bagga et al.

(10) Patent No.: US 9,629,728 B2
(45) Date of Patent: Apr. 25, 2017

(54) BIOACTIVE SPINAL IMPLANTS AND METHOD OF MANUFACTURE THEREOF

(71) Applicant: Orthovita, Inc., Malvern, PA (US)

(72) Inventors: Charanpreet S. Bagga, Basking Ridge, NJ (US); Erik M. Erbe, Chesterfield, MO (US); James P. Murphy, Newtown Square, PA (US); James M. Freid, Austin, TX (US); Gregory J. Pomrink, Newberry, FL (US)

(73) Assignee: Orthovita, Inc., Malvern, PA (US)

( * ) Notice: Subject to any disclaimer, the term of this patent is extended or adjusted under 35 U.S.C. 154(b) by 0 days.

(21) Appl. No.: 14/936,139

(22) Filed: Nov. 9, 2015

(65) Prior Publication Data

US 2016/0058568 A1    Mar. 3, 2016

Related U.S. Application Data

(60) Continuation of application No. 14/244,354, filed on Apr. 3, 2014, now Pat. No. 9,211,194, which is a
(Continued)

(51) Int. Cl.
*A61F 2/44*    (2006.01)
*A61F 2/46*    (2006.01)
(Continued)

(52) U.S. Cl.
CPC ............ *A61F 2/442* (2013.01); *A61F 2/4455* (2013.01); *A61F 2/4611* (2013.01); *A61L 27/446* (2013.01); *A61L 27/50* (2013.01); *A61L 31/16* (2013.01); *A61L 31/18* (2013.01); *A61B 17/1659* (2013.01); *A61B 17/1671* (2013.01); *A61B 17/86* (2013.01);
(Continued)

(58) Field of Classification Search
CPC ........ A61F 2/44; A61F 2/4455; A61F 2/4611; A61F 2310/00023; A61F 2310/00017
See application file for complete search history.

(56) References Cited

U.S. PATENT DOCUMENTS 4,065,360 A    12/1977    Kreb, III
4,110,184 A    8/1978    Dart et al.
(Continued)

FOREIGN PATENT DOCUMENTS

DE    19738052 A1    3/1999
FR    2795945 A1    1/2001
(Continued)

OTHER PUBLICATIONS

International Search Report for Application No. PCT/US02/39184 dated May 20, 2003.
(Continued)

*Primary Examiner* — Thomas J Sweet
*Assistant Examiner* — Tiffany Shipmon
(74) *Attorney, Agent, or Firm* — Lerner, David, Littenberg, Krumholz & Mentlik, LLP

(57) ABSTRACT

A bioactive spinal implant used in cervical fusion, Anterior Lumbar Interbody Fusion (ALIF), Posterior Lumbar Interbody Fusion (PLIF), and Transforaminal Interbody Fusion (TLIF), having properties and geometries that enhance bone contact, stability, and fusion between adjacent vertebral bodies.

22 Claims, 56 Drawing Sheets

Related U.S. Application Data division of application No. 11/736,314, filed on Apr. 17, 2007, now Pat. No. 8,715,353, which is a division of application No. 10/256,566, filed on Sep. 26, 2002, now Pat. No. 7,238,203.

(60) Provisional application No. 60/339,871, filed on Dec. 12, 2001.

(51) Int. Cl.

| | | |
|---|---|---|
| *A61L 27/44* | (2006.01) | |
| *A61L 27/50* | (2006.01) | |
| *A61L 31/16* | (2006.01) | |
| *A61L 31/18* | (2006.01) | |
| *A61B 17/16* | (2006.01) | |
| *A61B 17/86* | (2006.01) | |
| *A61F 2/30* | (2006.01) | |
| *A61F 2/36* | (2006.01) | |
| *A61F 2/28* | (2006.01) | |

(52) U.S. Cl.
CPC ............ *A61F 2/30965* (2013.01); *A61F 2/36* (2013.01); *A61F 2/44* (2013.01); *A61F 2/447* (2013.01); *A61F 2/4684* (2013.01); *A61F 2002/2835* (2013.01); *A61F 2002/2892* (2013.01); *A61F 2002/305* (2013.01); *A61F 2002/3008* (2013.01); *A61F 2002/30062* (2013.01); *A61F 2002/30133* (2013.01); *A61F 2002/30448* (2013.01); *A61F 2002/30578* (2013.01); *A61F 2002/30599* (2013.01); *A61F 2002/30616* (2013.01); *A61F 2002/30617* (2013.01); *A61F 2002/30784* (2013.01); *A61F 2002/30828* (2013.01); *A61F 2002/30904* (2013.01); *A61F 2002/30957* (2013.01); *A61F 2002/3631* (2013.01); *A61F 2002/4475* (2013.01); *A61F 2002/4622* (2013.01); *A61F 2002/4623* (2013.01); *A61F 2002/4627* (2013.01); *A61F 2002/4628* (2013.01); *A61F 2002/4629* (2013.01); *A61F 2002/4681* (2013.01); *A61F 2210/0004* (2013.01); *A61F 2220/005* (2013.01); *A61F 2220/0016* (2013.01); *A61F 2220/0025* (2013.01); *A61F 2230/0015* (2013.01); *A61F 2250/0063* (2013.01); *A61F 2250/0097* (2013.01); *A61F 2250/0098* (2013.01); *A61F 2310/00017* (2013.01); *A61F 2310/00023* (2013.01); *A61F 2310/00029* (2013.01); *A61F 2310/00161* (2013.01); *A61F 2310/00179* (2013.01); *A61F 2310/00293* (2013.01); *A61F 2310/00329* (2013.01); *A61L 2430/38* (2013.01)

(56) References Cited

U.S. PATENT DOCUMENTS

| | | | |
|---|---|---|---|
| 4,491,453 A | 1/1985 | Koblitz et al. | |
| 4,698,373 A | 10/1987 | Tateosian et al. | |
| 4,801,263 A | 1/1989 | Clark | |
| 4,801,528 A | 1/1989 | Bennett | |
| 5,009,597 A | 4/1991 | Schaefer | |
| 5,024,232 A | 6/1991 | Smid et al. | |
| 5,415,546 A | 5/1995 | Cox, Sr. | |
| 5,425,772 A | 6/1995 | Brantigan | |
| 5,681,742 A | 10/1997 | MersKelly et al. | |
| 5,681,872 A | 10/1997 | Erbe | |
| 5,766,252 A | 6/1998 | Henry et al. | |
| 5,772,665 A | 6/1998 | Glad et al. | |
| 5,824,084 A | 10/1998 | Muschler | |
| 5,865,845 A | 2/1999 | Thalgott | |
| 5,914,356 A | 6/1999 | Erbe | |
| 5,939,039 A | 8/1999 | Sapieszko et al. | |
| 5,989,289 A | 11/1999 | Coates et al. | |
| 6,039,762 A | 3/2000 | McKay | |
| 6,049,026 A | 4/2000 | Muschler | |
| 6,113,638 A * | 9/2000 | Williams ................ | A61F 2/442 128/898 |
| 6,123,731 A | 9/2000 | Boyce et al. | |
| 6,132,465 A | 10/2000 | Ray et al. | |
| 6,143,033 A | 11/2000 | Paul et al. | |
| 6,241,771 B1 | 6/2001 | Gresser et al. | |
| 6,261,586 B1 | 7/2001 | McKay | |
| 6,277,149 B1 | 8/2001 | Boyle et al. | |
| 6,383,519 B1 | 5/2002 | Sapieszko et al. | |
| 6,432,106 B1 | 8/2002 | Fraser et al. | |
| 6,458,159 B1 | 10/2002 | Thalgott | |
| 6,482,233 B1 | 11/2002 | Aebi et al. | |
| 6,503,279 B1 | 1/2003 | Webb et al. | |
| 6,520,993 B2 | 2/2003 | James et al. | |
| 6,669,699 B2 | 12/2003 | Ralph et al. | |
| 6,964,687 B1 | 11/2005 | Bernard et al. | |
| 6,987,136 B2 | 1/2006 | Erbe et al. | |
| 7,045,125 B2 | 5/2006 | Erbe et al. | |
| 2001/0005796 A1 | 6/2001 | Zdeblick et al. | |
| 2002/0062153 A1* | 5/2002 | Paul ......................... | A61F 2/28 623/17.11 |
| 2002/0161443 A1 | 10/2002 | Michelson | |
| 2005/0125029 A1 | 6/2005 | Bernard et al. | |

FOREIGN PATENT DOCUMENTS

| | | |
|---|---|---|
| WO | 0059413 A1 | 10/2000 |
| WO | 0103615 A1 | 1/2001 |
| WO | 0128465 A2 | 4/2001 |

OTHER PUBLICATIONS

John W. Brantigan, MD., "Compression strength of donor bone for posterior lumbar interbody fusion", Spine, 1993, 1213-1221.

Pattin, C.A. et al., "Cyclic mechanical property degradation during fatigue loading of cortical bone", J Biomechanics, 1996, 29(1), 69-79.

Zioupos, P., et al., "Experimental and theoretical quantification of the development of damage in fatigue tests ofbone and antler", 1996, 29(8), 989-1002.

International Search Report for Application No. PCT/US02/20887 dated Sep. 18, 2002.

* cited by examiner

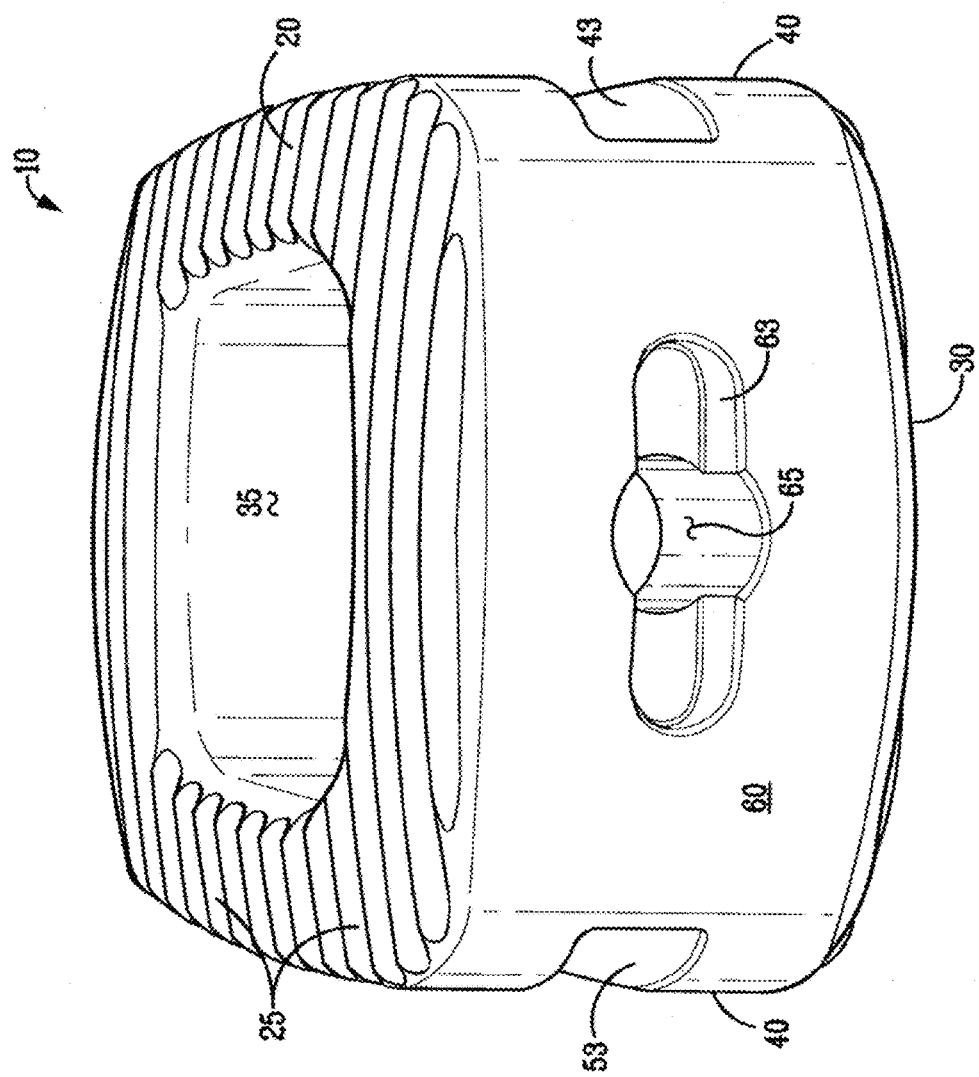

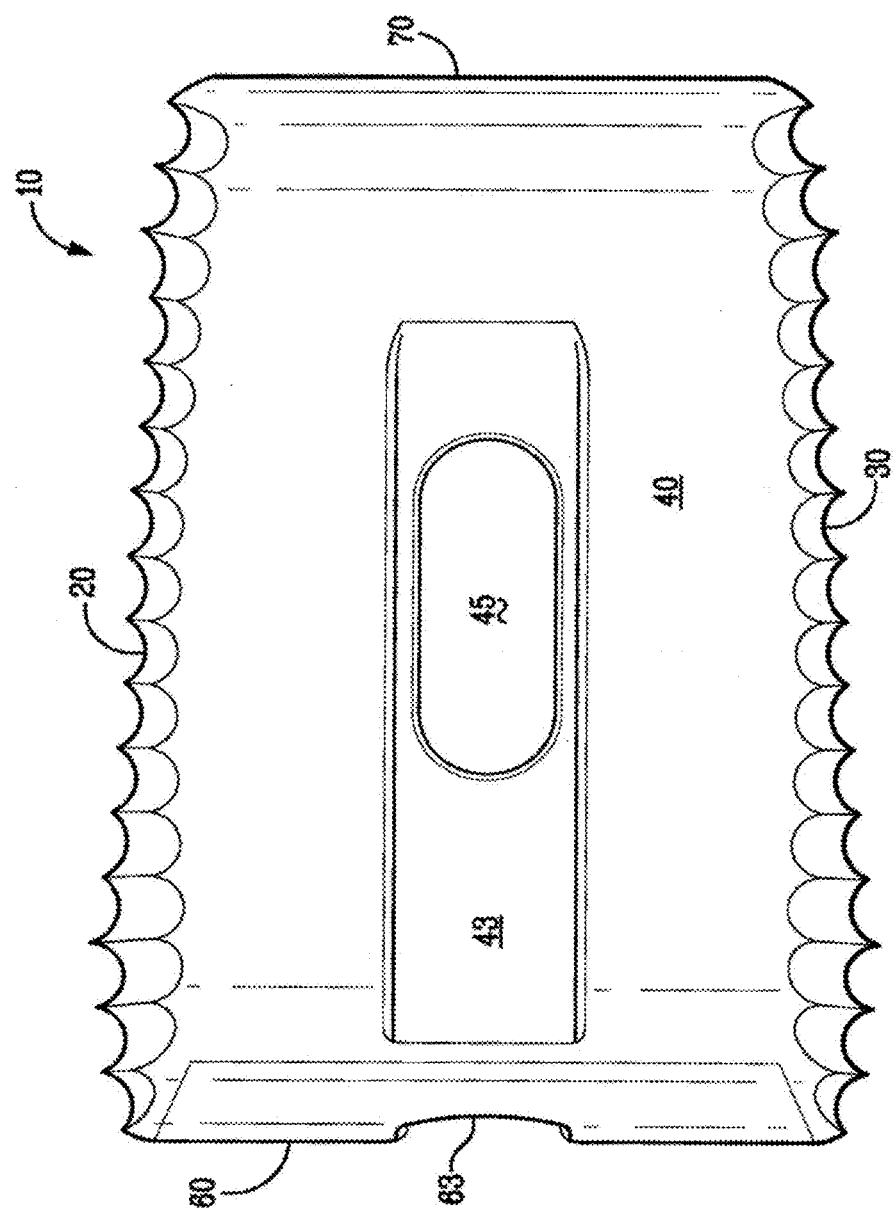

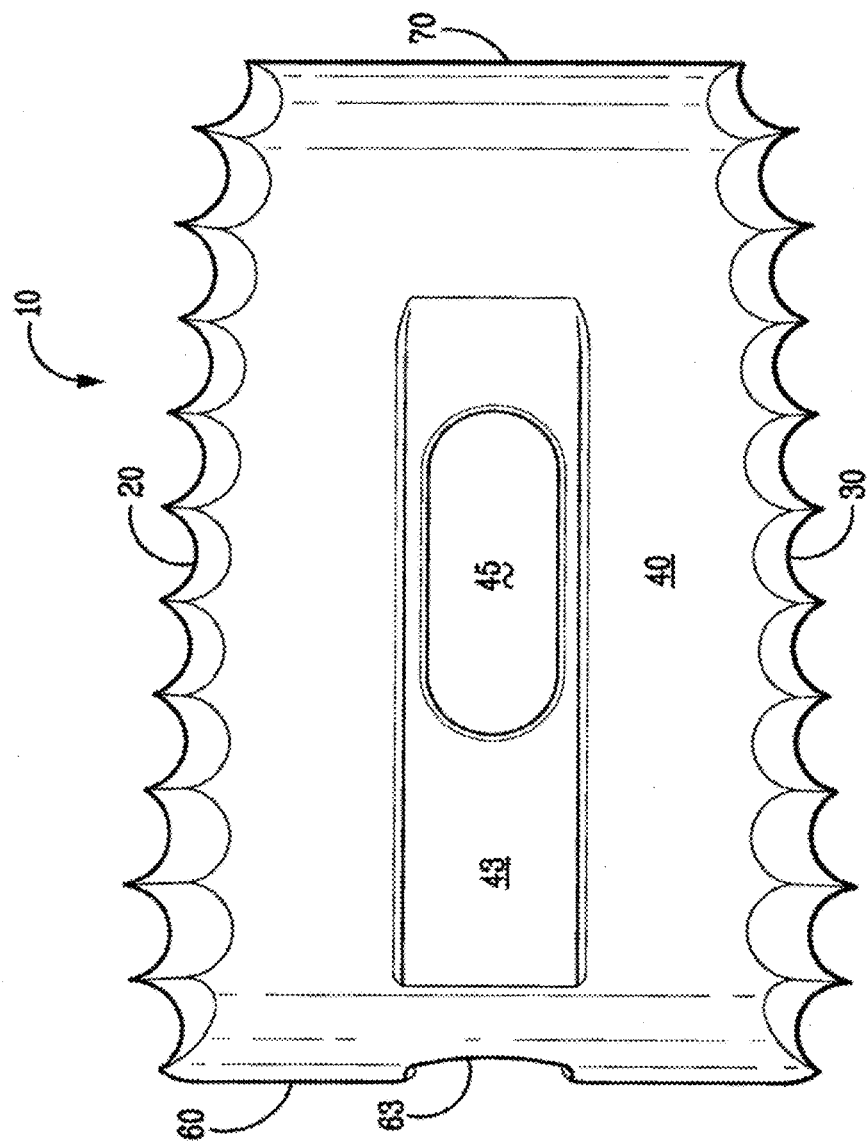

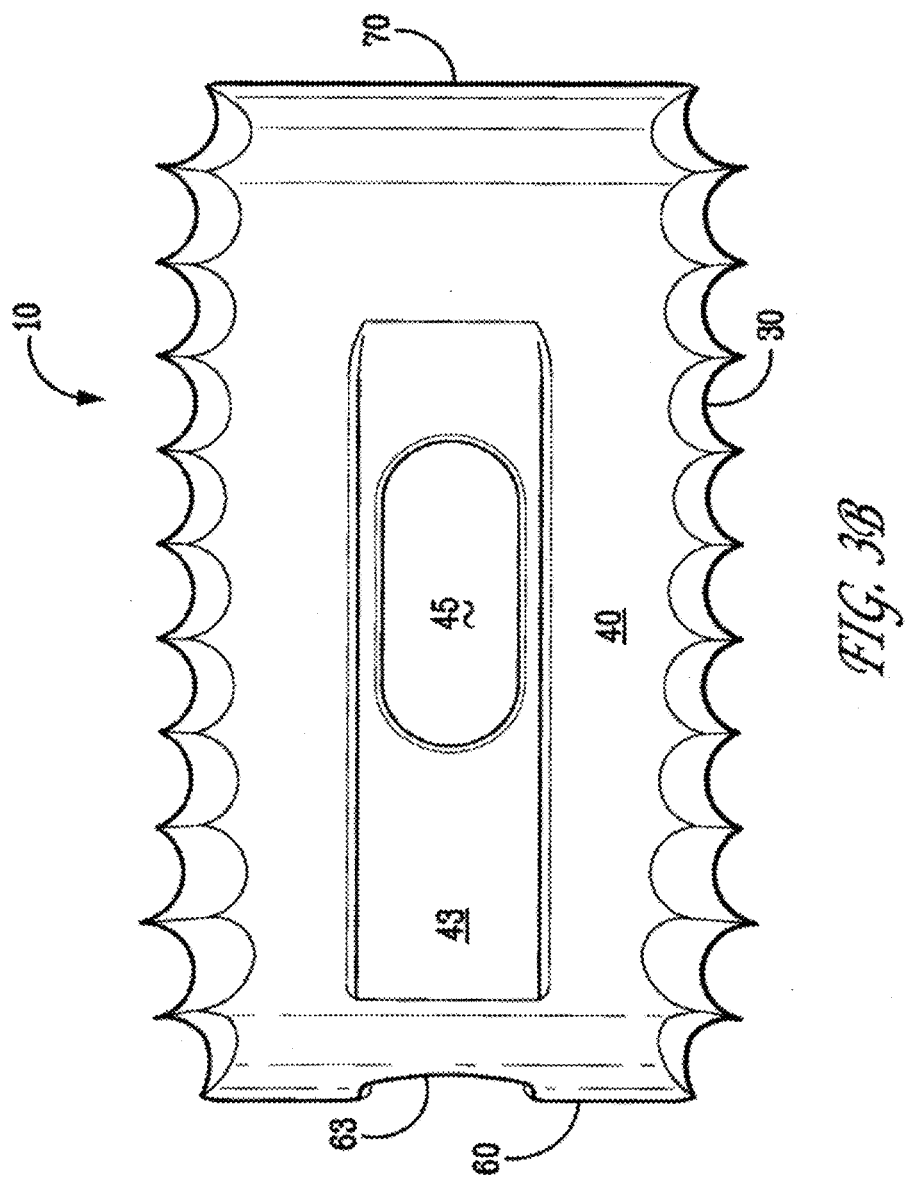

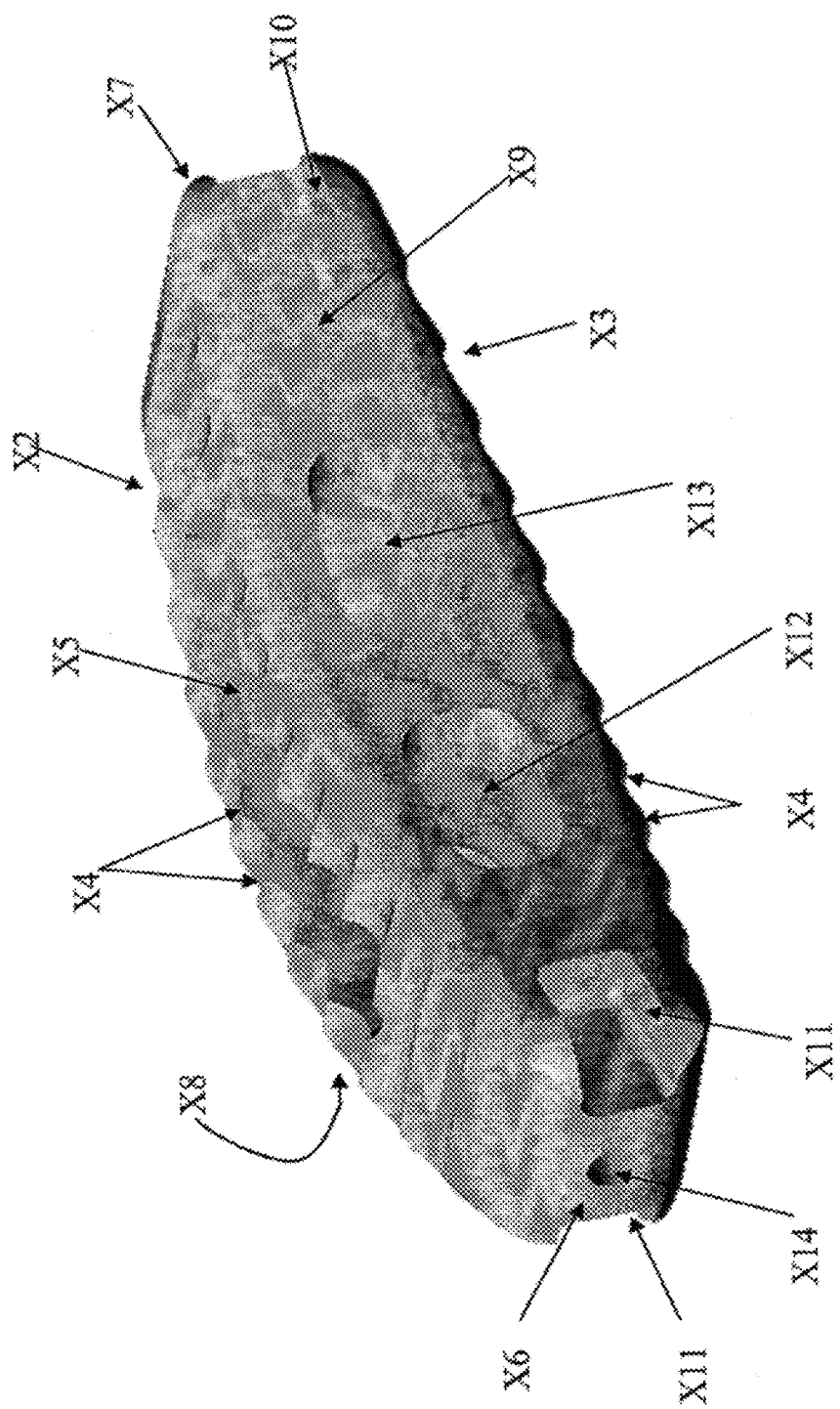

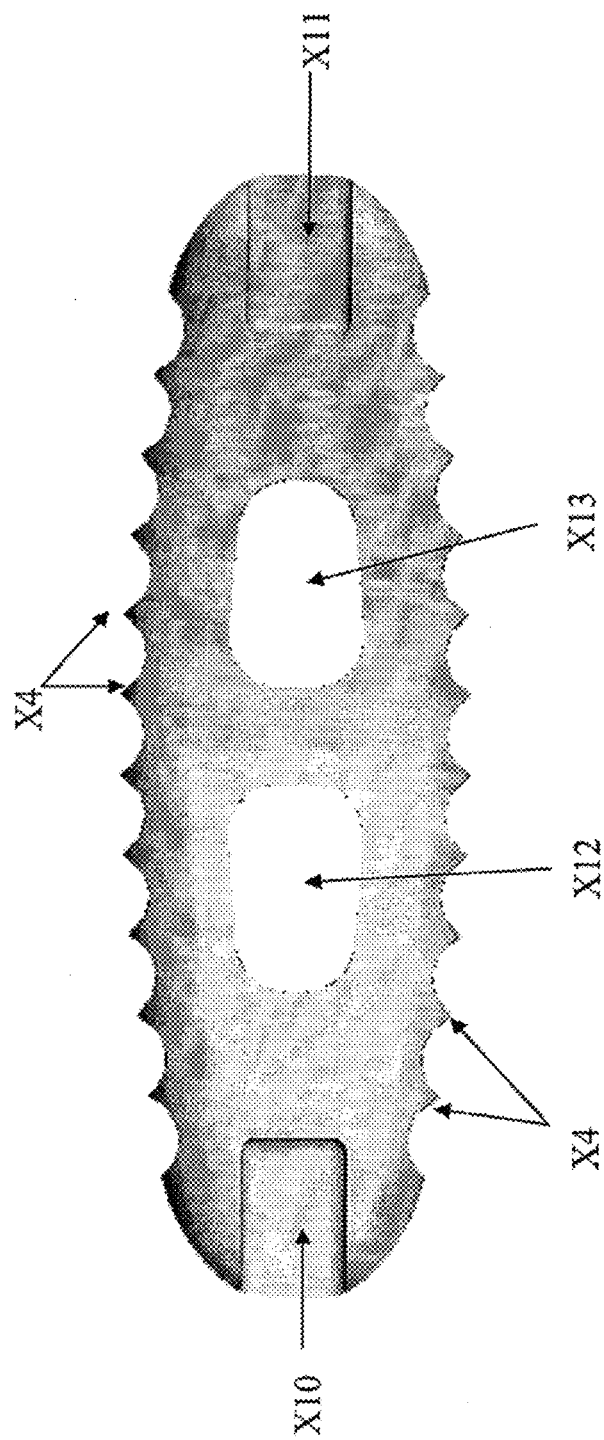

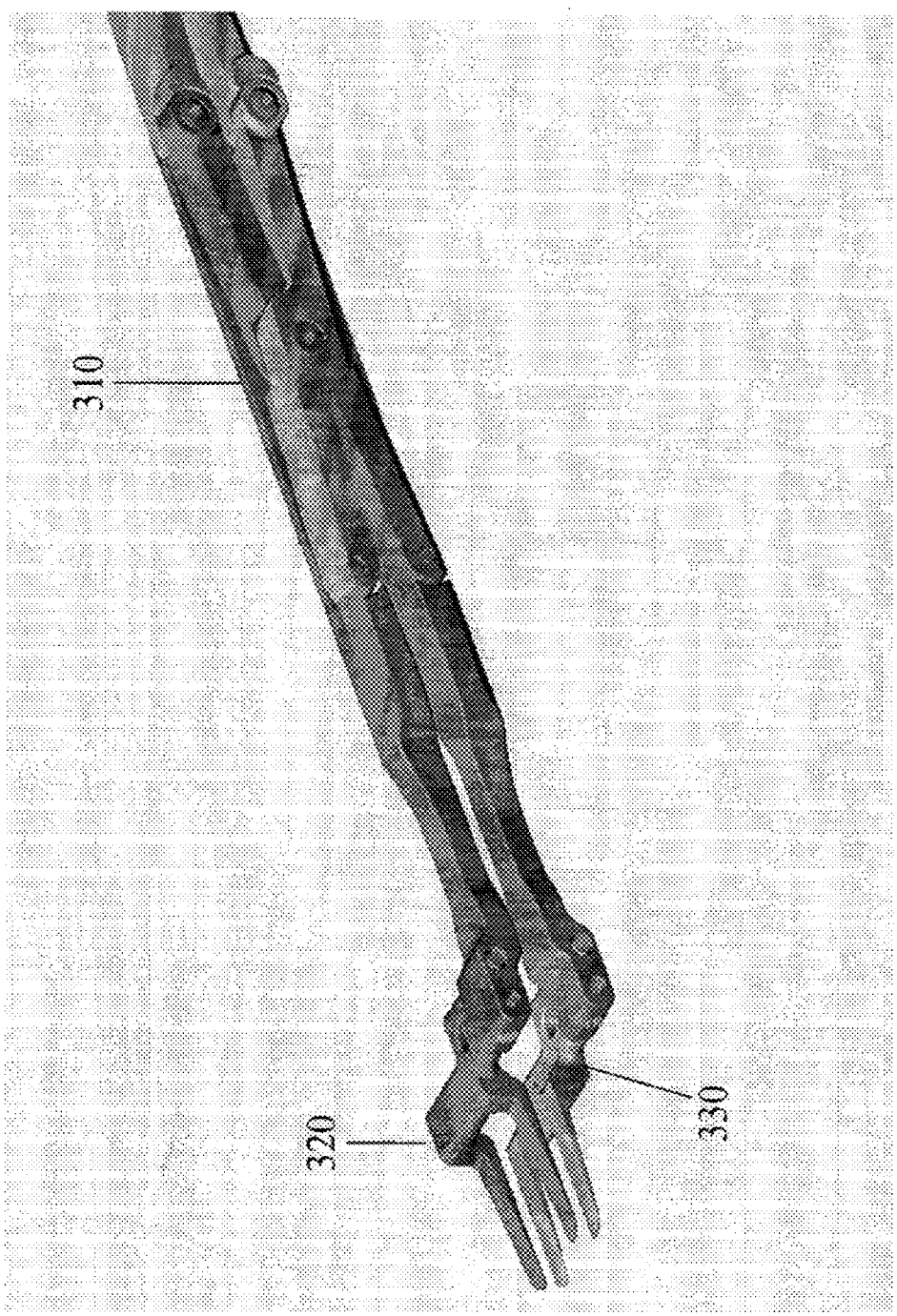

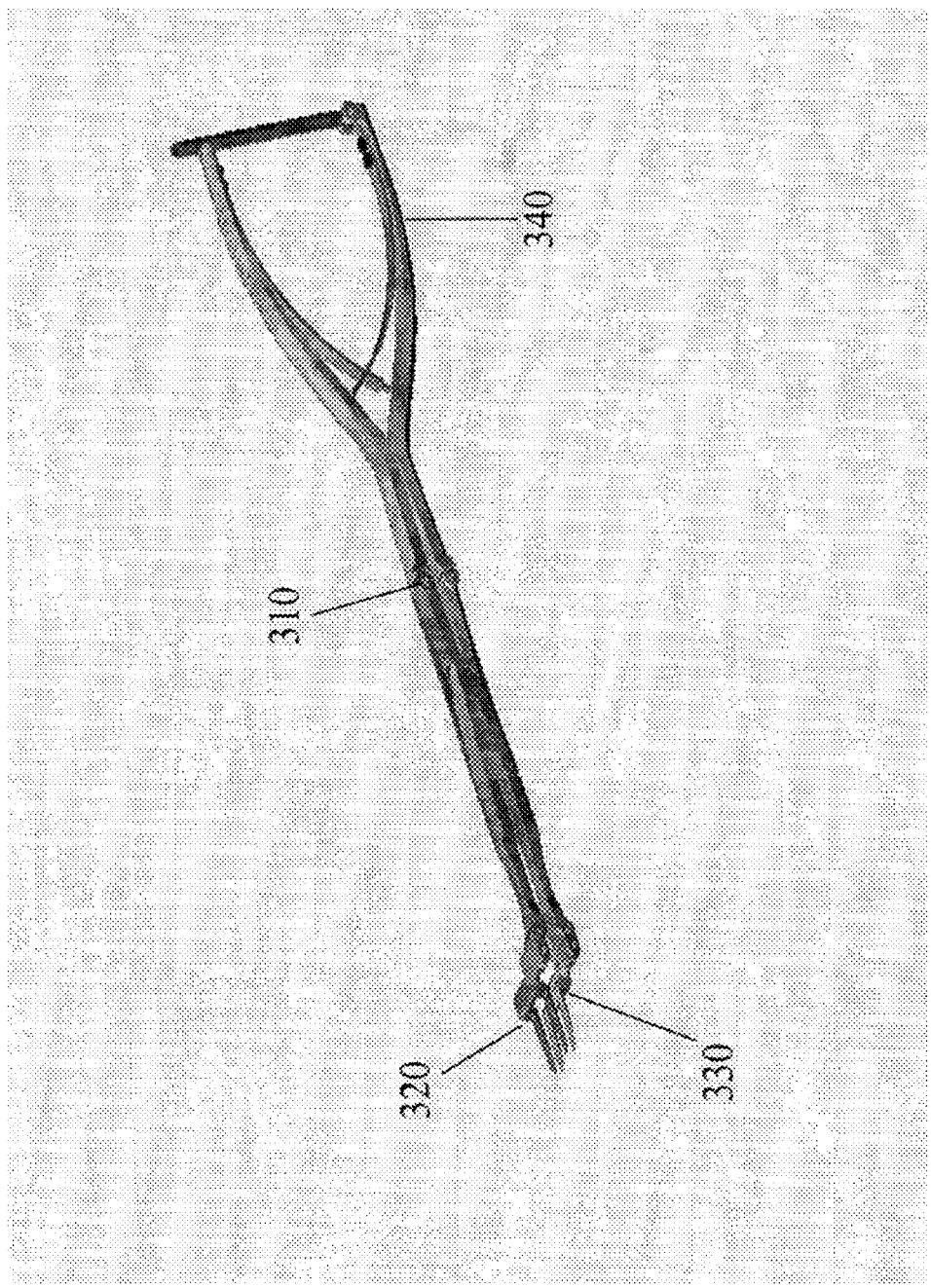

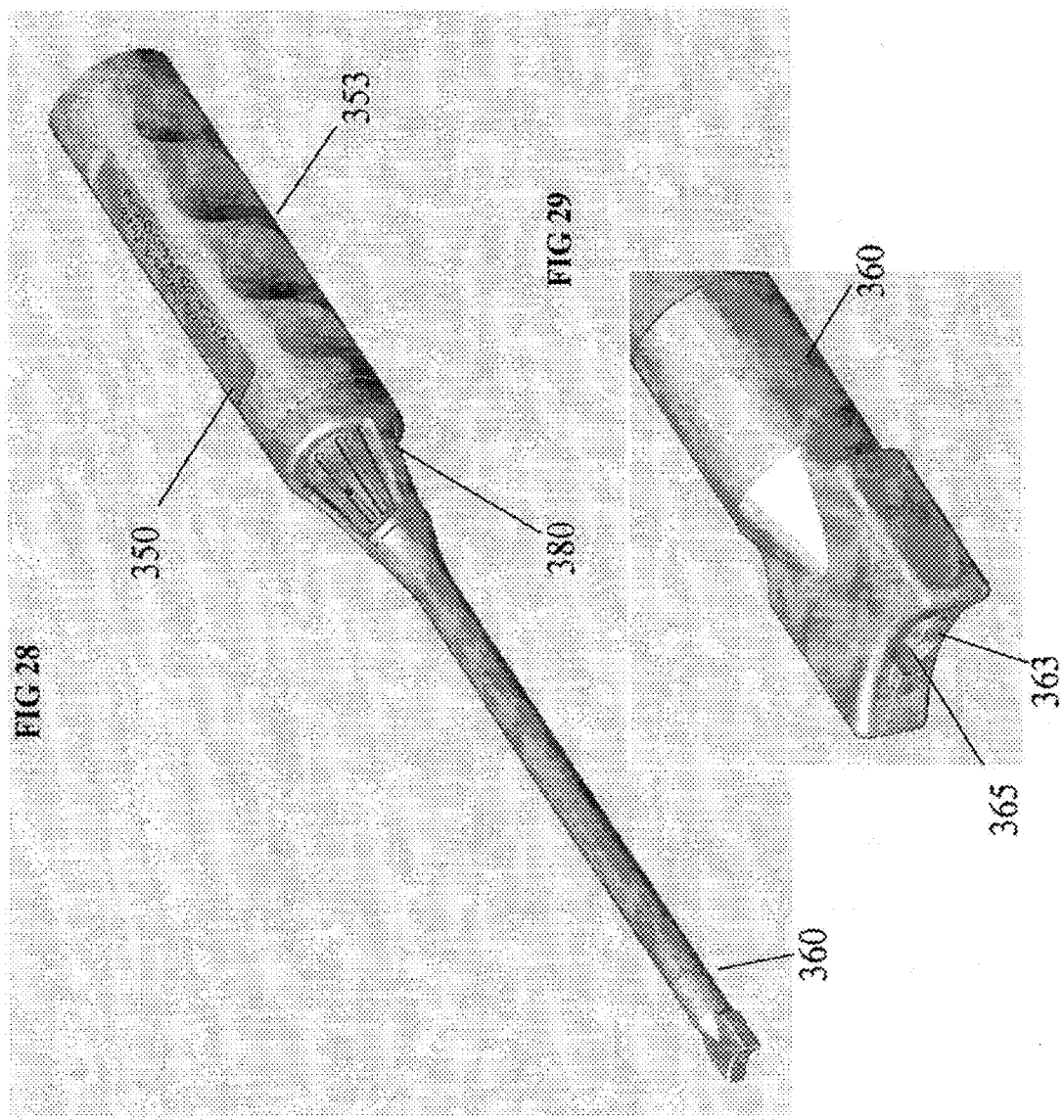

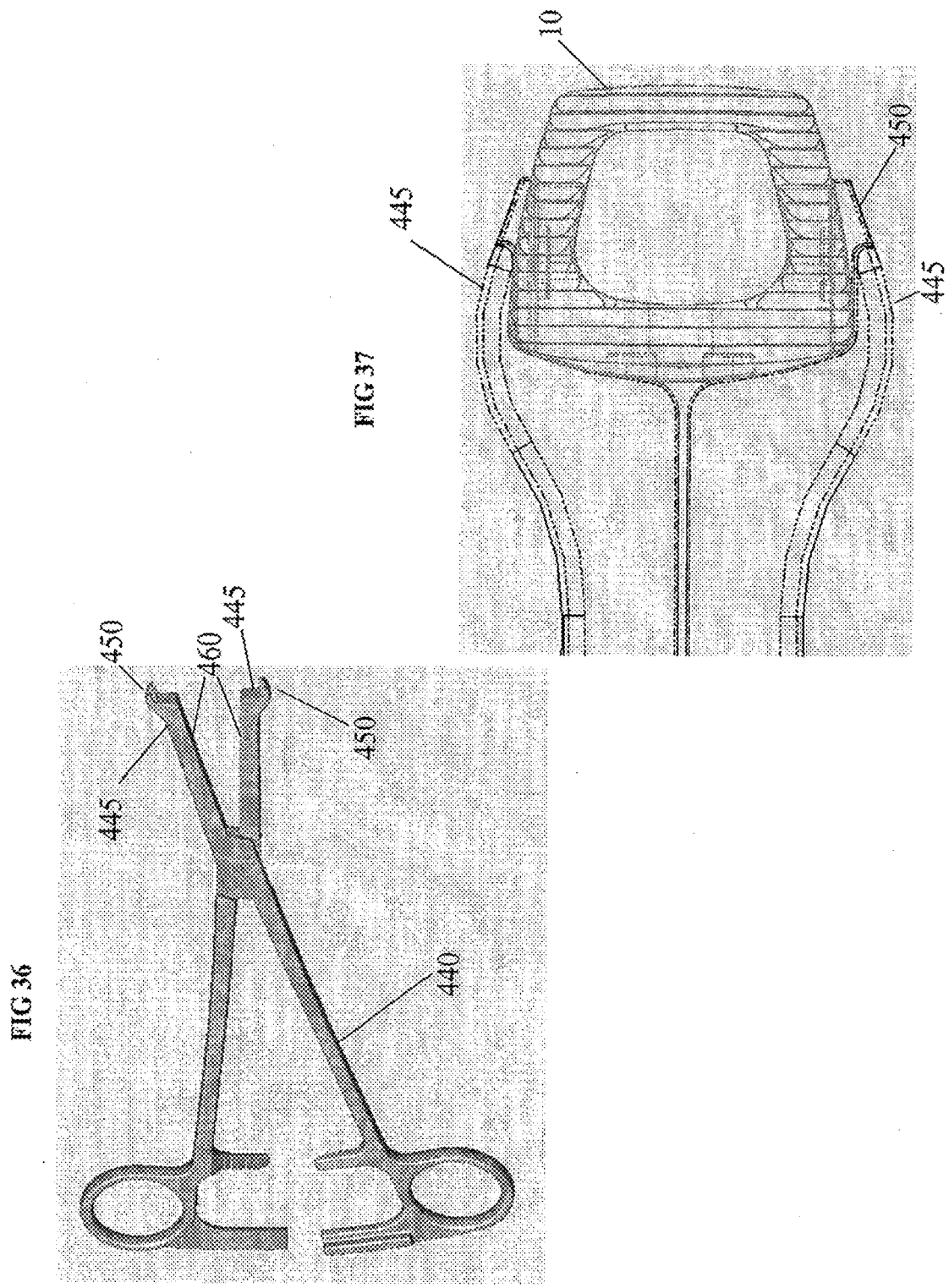

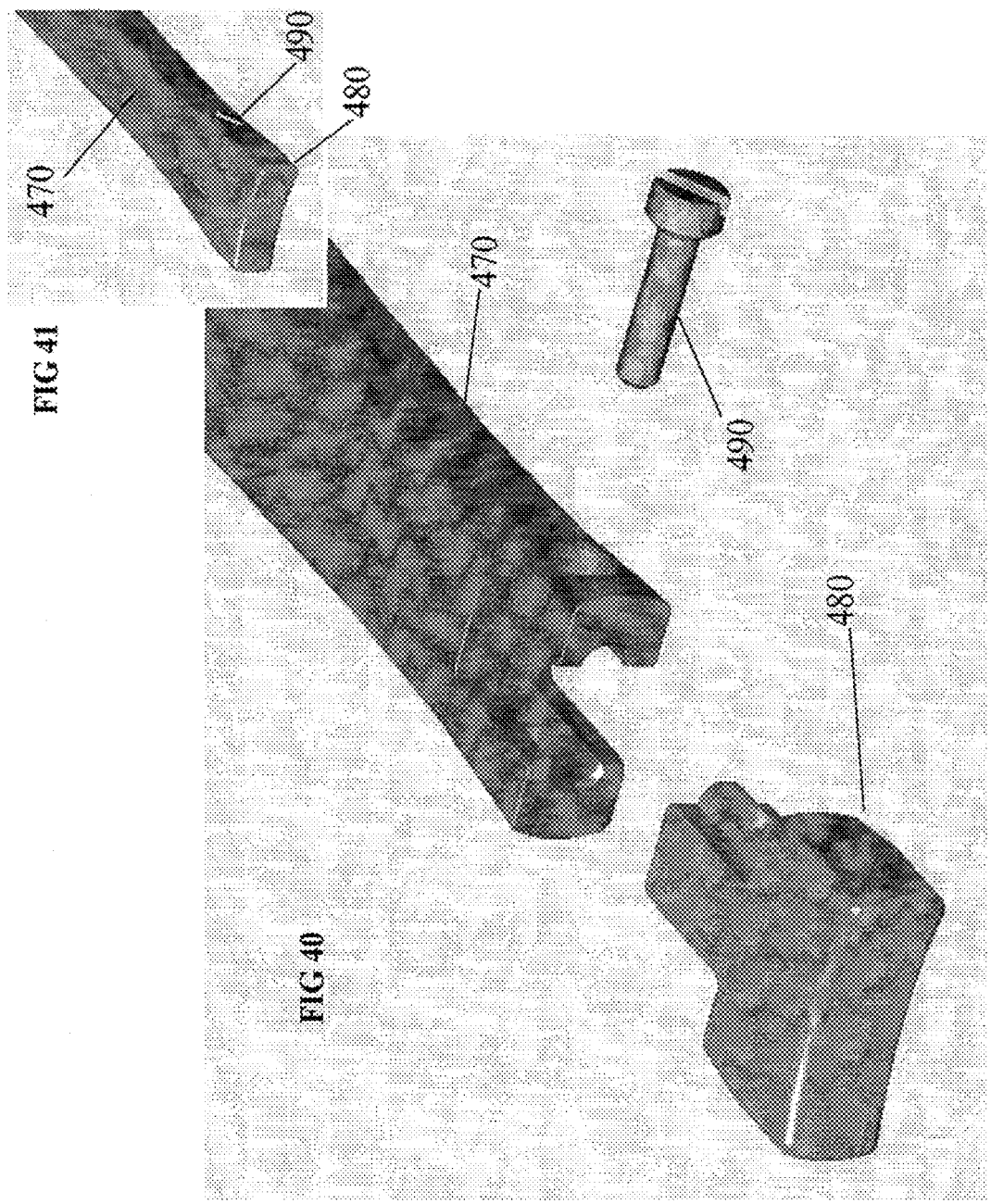

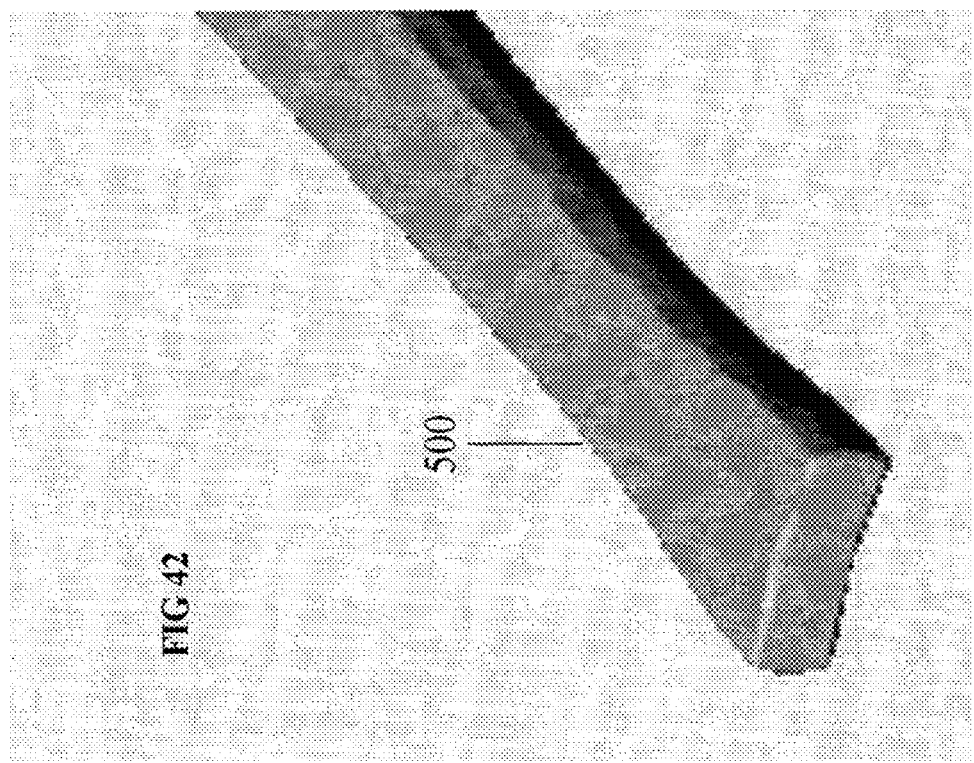

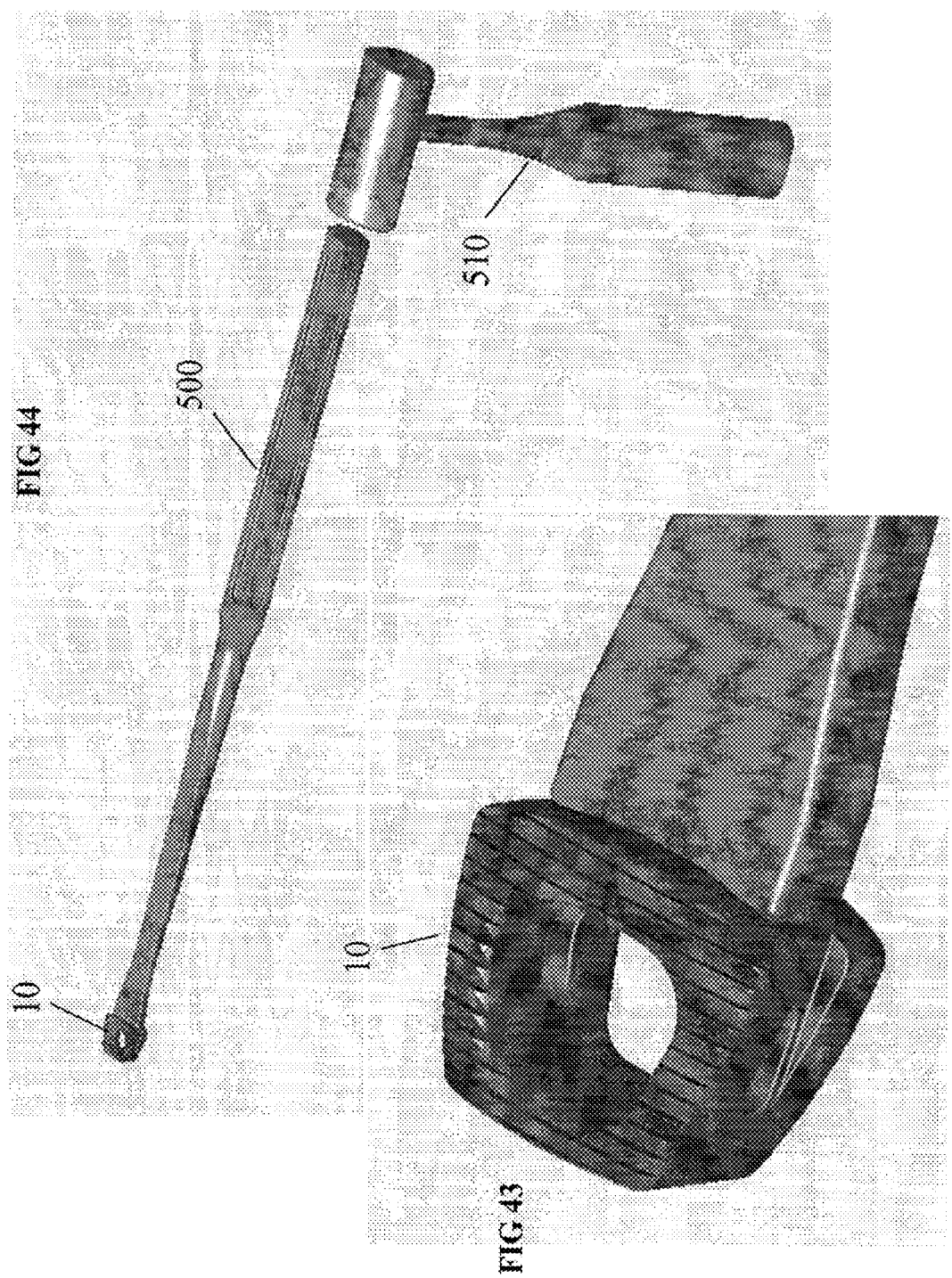

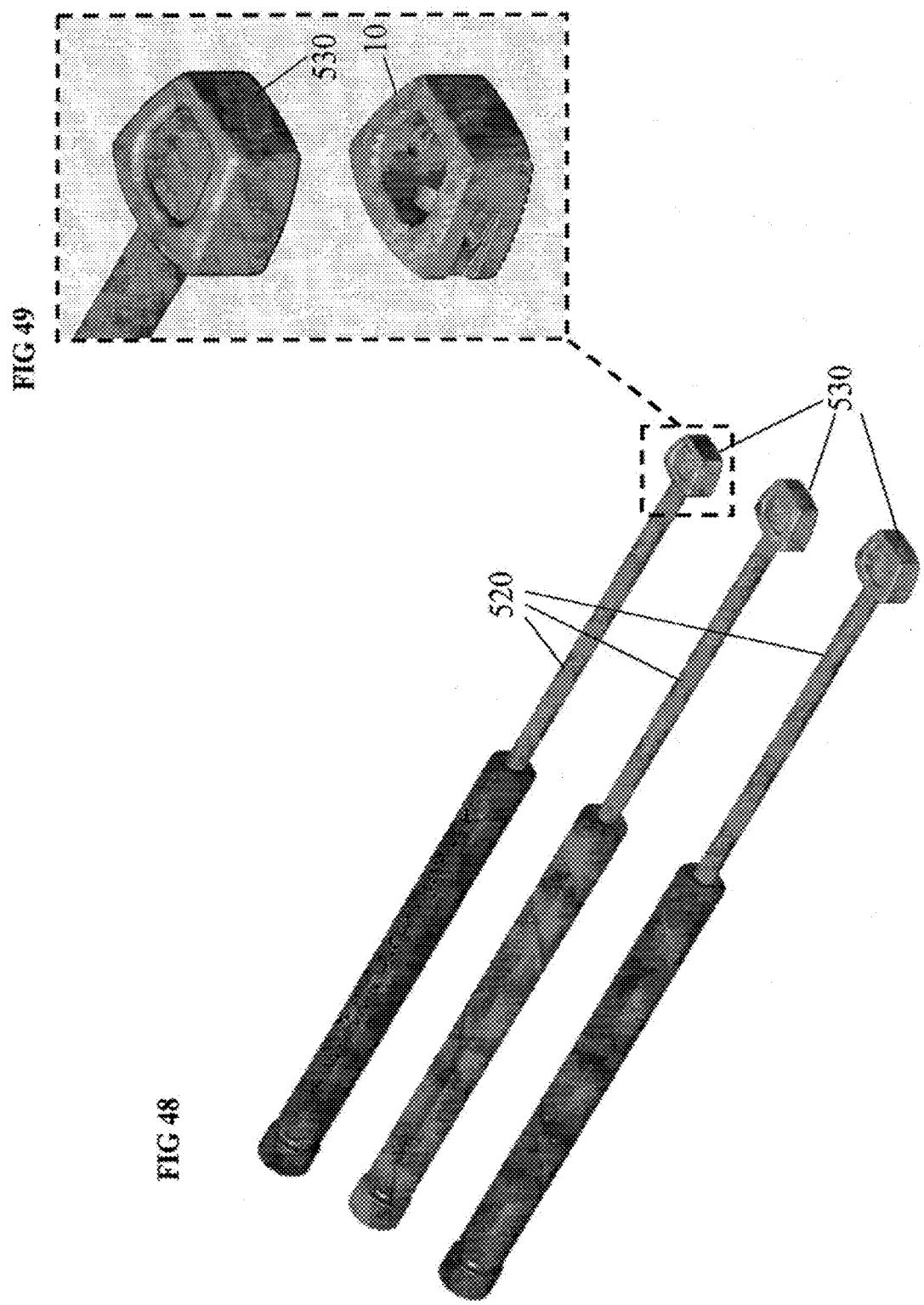

BIOACTIVE SPINAL IMPLANTS AND METHOD OF MANUFACTURE THEREOF

CROSS-REFERENCE TO RELATED APPLICATIONS

This application is a continuation of U.S. application Ser. No. 14/244,354, filed Apr. 3, 2014, which is a divisional of U.S. application Ser. No. 11/736,314, filed Apr. 17, 2007 and now U.S. Pat. No. 8,715,353, which is a divisional of U.S. application Ser. No. 10/256,566, filed Sep. 26, 2002 and now U.S. Pat. No. 7,238,203, which claims priority to U.S. Provisional Application No. 60/339,871, filed on Dec. 12, 2001, the contents of which are incorporated herein by reference in their entireties.

FIELD OF THE INVENTION

This present invention generally relates to spinal fixation devices, and spinal implants, suitable for use in orthopedic applications in which the implant is subjected to dynamic, compressive loads. The implants of the present invention may be used in procedures such as cervical fusion, Anterior Lumbar Interbody Fusion (ALIF), Posterior Lumbar Interbody Fusion (PLIF), and Transforaminal Lumbar Interbody Fusion (TLIF). They may be implanted between adjacent vertebrae to treat or prevent back pain in patients with conditions such as degenerative disc disease. The present invention also relates to methods of making bioactive implants and apparatuses for manipulating them.

BACKGROUND OF THE INVENTION

Lower back and neck pain is oftentimes attributed to the rupture or degeneration of intervertebral discs due to degenerative disk disease, spondylolisthesis, deformative disorders, trauma, tumors and the like. This pain typically results from the compression of spinal nerve roots by damaged discs between the vertebra, the collapse of the disc, or the resulting adverse effects of bearing the patient's body weight through a damaged, unstable vertebral structure. To remedy this, spinal implants have been inserted between vertebral bodies to restore the structure to its previous height and conformation and stabilize motion at that spinal segment.

Surgical treatments to restore vertebral height typically involve excision of the ruptured soft disc between two vertebrae, usually with subsequent insertion of a spinal implant or interbody fusion device to fuse and stabilize the segment. Spinal implants or interbody fusion devices have been used to fuse adjacent vertebral bodies since the 1960's. Currently, spinal implant devices are comprised of either allograft materials, natural, porous materials such as coral, or synthetic materials. A major drawback associated with allograft devices is the risk of disease transmission. Further, since companies that provide allograft implants obtain their supply from donor tissue banks, there tend to be limitations on supply. Synthetic devices, which are predominantly comprised of metals, such as titanium, also present drawbacks. For instance, the appearance of metal spinal implants on x-ray tends to have an artificial fuzziness, which makes assessment of fusion (one of the clinical criteria of a successful interbody fusion device) very difficult. Moreover, synthetic materials of this type (metals) tend to have mechanical properties that are unevenly matched to bone. Coral and other natural materials generally perform poorly.

Accordingly, there is a need in the art for a synthetic spinal implant material that does not carry the risk of disease transmission as with allograft materials.

There is also a need for a synthetic spinal implant material with a radiopacity similar to bone. A radiopacity similar to bone would allow for visualization of the implant between the vertebrae to assess radiographic fusion without distortion.

Further, there is a need for implants with mechanical properties similar to that of bone that can share the physiologic, dynamic compressive loads rather than shield them.

Moreover, there is a need for implants that are comprised of a material that bonds directly to bone and is bioactive.

In addition to the material limitations associated with existing implants on the market, there is also a need to provide spinal implants that are anatomically shaped with proper geometry and features to prevent expulsion or retropulsion. The term "expulsion" as used herein relates to the migration of the implant device in a forward (or backward) direction from the intervertebral space. Moreover, there is a need for a device with an increased surface area to allow for optimal contact with the cortical bone to prevent subsidence or sinking of the implant into each adjacent vertebra. There is a need to provide an implant that is bioactive with an open geometry for packing with graft materials that allows enhanced fusion between the endplates of adjacent vertebrae both via the bioactive surface of the implant and a preferred graft-packed opening.

BRIEF DESCRIPTION OF THE DRAWINGS

The invention will be more clearly understood when considered in conjunction with the drawing figures, wherein:

FIG. 2 provides a front view illustrating the anterior side of the cervical implant 10.

FIG. 3 provides a side view illustrating the medial side of the cervical implant 10.

FIGS. 3a and 3b provide side views illustrating the cervical implant 10 with and without a lordotic angle, respectively.

FIG. 22C provides an isometric view of one embodiment of a TLIF implant x1 illustrating two lateral openings.

FIG. 22D provides a planar view illustrating the openings x12 and x13 and recesses on the anterior x8 and posterior xa sides of the TLIF implant x1.

FIG. 26 provides a detailed, isometric view of the parallel distraction instrument 310.

FIG. 27 provides an isometric view of the parallel distraction instrument 310 illustrating the grasping end 340 or handle of the instrument.

FIG. 28 provides an isometric view of one embodiment of the implant insertion tool 350.

FIG. 29 provides a detailed view of the tip of the implant insertion tool 350.

FIG. 36 provides a planar view of one embodiment of forceps 440.

FIG. 37 provides a detailed, planar view of the forceps 440 engaging cervical implant 10.

FIG. 40 provides an exploded, isometric view of one embodiment of the insertion tool 470 of the present invention.

FIG. 41 provides an isometric view of the assembled insertion tool 470.

FIG. 42 provides an isometric view of another embodiment of the insertion tool 500.

FIG. 43 provides a detailed isometric view of an embodiment of the insertion tool 500 of the present invention engaging the cervical implant 10.

FIG. 44 provides an isometric view of the insertion tool 00 and one embodiment of the impactor hammer 510 of the present invention.

FIG. 48 provides isometric views of one embodiment of trial implant tools of the present invention.

FIG. 49 provides a detailed, isometric view of the trial implant of FIG. 48.

SUMMARY OF THE INVENTION

Figure 1:
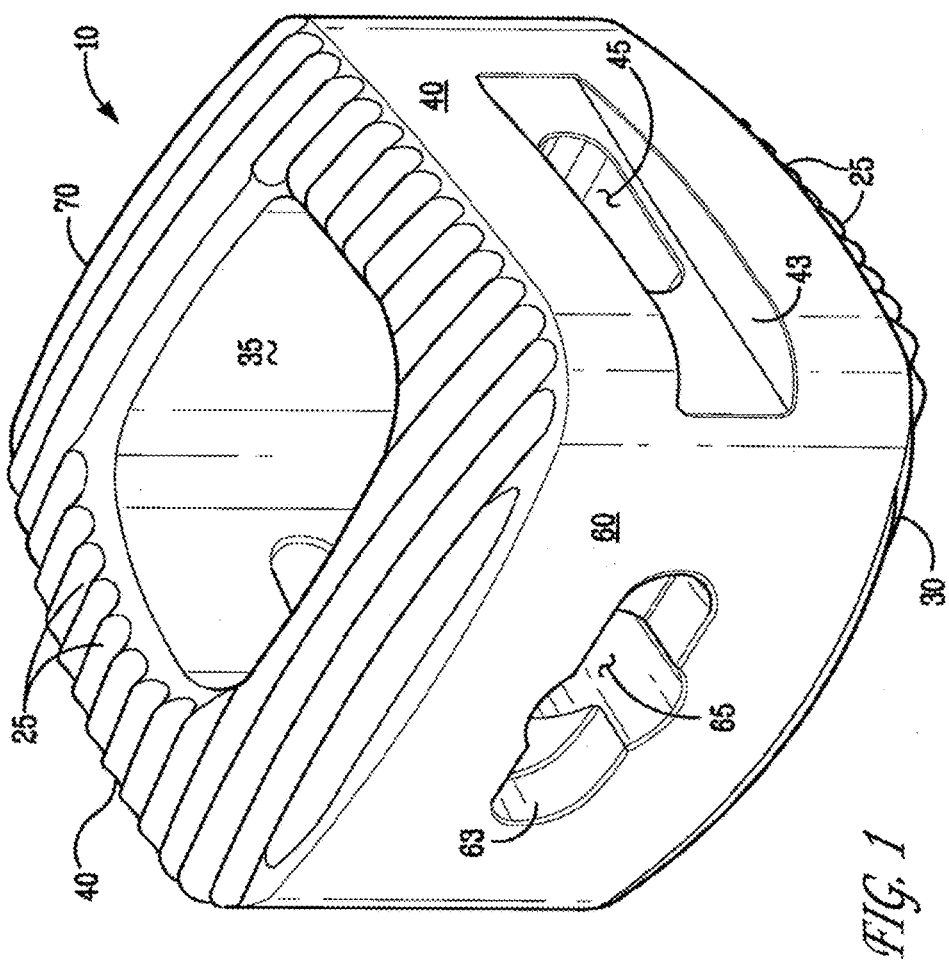
FIG. 1 provides an isometric view of one embodiment of a cervical implant 10.

The present invention provides spinal implants that have a radiopacity similar to bone for facilitating radiographic assessment of fusion. The present invention also provides spinal implants having properties and geometries that enhance bone contact, stability and fusion between adjacent vertebral bodies. The implants of the present invention are comprised of bioactive and biocompatible materials capable of withstanding physiologic dynamic, compressive loads. As used herein, bioactive relates to the chemical formation of a calcium phosphate layer, such as, via ion exchange between surrounding fluid and the implant material. More broadly, it also relates to a material that elicits a reaction which leads to bone formation or attachment into or adjacent to the implant, for example, bone formation or apposition directly to the implant usually without intervening fibrous tissue. Biocompatible as used herein relates to a material that does not invoke a prolonged, adverse immunologic or host response.

The present invention also provides methods for making such implants and instrumentation for inserting same. In one embodiment of the present invention, there is provided a spinal implant comprised of a top and a bottom surface having a substantially trapezoidal cross-section, a plurality of wave-like protrusions, and at least one opening. The top and bottom surface are preferably substantially convex with respect to each other; and have a pair of medial and lateral sides that extend between the top and bottom surfaces. The medial and lateral sides preferably have at least one indentation and at least one opening. A pair of anterior and posterior sides preferably extends between the top and bottom surfaces and contacts at least a portion of the pair of medial and lateral sides. The anterior or posterior sides also preferably have at least one opening.

In another embodiment of the present invention the implant has a generally trapezoidal, ring-shaped body with bowed sides and convex superior and inferior surfaces. Such configuration is particularly suitable for use in orthopedic applications, such as in the spine, as a spinal implant. The implant is anatomically shaped to prevent subsidence and preferably includes projections, ridges, warps or teeth on the superior and inferior surfaces for gripping adjacent bone and preventing migration of the device. The implant also preferably has at least one opening which accommodates insertion of the device and at least one opening which accommodates packing of the implant with graft material to facilitate the formation of a solid fusion structure.

In certain embodiments of the present invention, the implant materials of the present invention can be comprised of a biocompatible polymeric matrix reinforced or coated with bioactive fillers and fibers. The implants can probably be comprised of a diurethane dimethacrylate (DUDMA) and tri-ethylene glycol dimethacrylate (TEGDMA) blended resin and a plurality of fillers and fibers including bioactive fillers and E-glass fibers. The implants may also be comprised of a variety of other monomers and fillers as described herein.

I. Implant Materials

The present invention provides bioactive and biocompatible implant materials for formulation of shaped bodies capable of withstanding large dynamic, compressive loads, especially spinal implants. Further, the implant materials of the present invention overcome the risks associated with disease transmission present with allograft devices. Moreover, the implant materials of the present invention exhibit a radiopacity similar to that of bone for radiographic assessment of fusion as described in U.S. Pat. No. 6,987,136, issued Jan. 17, 2006, and incorporated herein by reference in its entirety.

The materials of this invention are preferably comprised of a biocompatible, hardenable polymeric matrix reinforced with bioactive and non-bioactive fillers. The materials can be comprised of about 10% to about 90% by weight of the polymeric matrix and about 10% to about 90% by weight of one or more fillers. The materials can also be comprised of about 20% to about 50% by weight of the polymeric matrix and about 50% to about 80% by weight of one or more fillers. In order to promote bone bonding to the implants, the implants of the present invention can be comprised of a bioactive material that can comprise a polymeric blended resin reinforced with bioactive ceramic fillers. Examples of such bioactive materials can be found, for example, in U.S. Pat. Nos. 5,681,872 and 5,914,356 and 6,987,136, which are assigned to the assignee of the present invention and incorporated herein by reference in their entireties.

The polymeric matrixes of the implant materials are comprised of polymerizable monomer, monomers, dimers or trimers. They can comprise ethylenically unsaturated monomers or even an acrylate functional group. The term "monomers," as used herein, can also represent dimers, trimers, resins, resin components, or any other polymerizable component. Examples of the monomers include, but are not limited to, DUDMA, bisphenol-A-glycidyl methacrylate (bis GMA), TEGDMA, ethoxylated bisphenol-A-dimethacrylate (bis-EMA), or combinations thereof. Still, further examples of monomers that can be used in the present invention include the adducts of 2,2,3-trimethylhexane diisocyanate with hydroxyethyl methacrylate, hydroxypropyl methacrylate, and other hydroxyacrylic acrylic species can also be used. Other examples of polymerizable species that can be used in the present invention include those disclosed in U.S. Pat. Nos. 5,681,872 and 5,914,356, and 6,987,136, which are incorporated herein by reference in their entireties.

Methyl methacrylate, ethyl methacrylate, propyl methacrylate, higher methacrylates, acrylates, ethacrylates, and similar species can be employed as all or part of the polymerizable materials of the implant materials of the present invention. It is also possible to employ other types of polymerizable material such as epoxide compounds, polyurethane-precursor species, and a wide host of other materials. For example, other monomers useful in the production of hardenable compositions of this invention include methyl-, ethyl, isopropyl-, tertbutyloctyl-, dodecyl-, cyclohexyl-, chloromethyl-, tetrachloroethyl-, perfluorooctyl-, hydroxyethyl-, hydroxypropyl-, hydroxybutyl-, 3-hydroxyphenyl-, 4-hydroxphenyl-, aminoethyl-, aminophenyl-, thiophenyl-, acrylate, methacrylate, ethacrylate, propacrylate, butacrylate, and chloromethacrylate, as well as the homologous mono-acrylic acid esters of bisphenol-A, dihydroxydiphenyl sulfone, dihydroxydiphenyl ether, dihydroxybiphenyl, dihydroxydiphenyl sulfoxide, and 2,2bis(4-hydroxy-2,3,5,6-tetrafluorophenyl)propane. Polymerizable monomers capable of sustaining a polymerization reaction such as the di-, tri-, and higher acrylic ethylene glycol dimethacrylate, diethylene glycol dimethacrylate, trimethylene glycol dimethacrylate, trimethylol propane trimethacrylate, analogous acrylates, and similar species are also useful. Polyetheretherketone (PEEK), carbon fiber reinforced PEEK, and carbon fiber reinforced barium sulfate impregnated Peek may also be used. Other polymers that may be used include polyethlene and polylactic acid (PLA). PLA may be used with pteroylgutamic acid (PGA) or PGA may be used without PLA. Poly-L-lactic acid (PLLA) may also be used. It is also possible to employ mixtures of more than two polymerizable species to good effect.

The implant materials can also comprise non-bioactive substances. Titanium, stainless steel, and cobalt chromium may also be used in the substances that comprise the spinal implant.

The implant materials of the present invention can further comprise polymeric additives that include, but are not limited to, polymerization inhibitors, polymerization activators, polymerization initiators, stabilizers such as UV-9, radiopacifiers, reinforcing components (i.e., fibers, particles, micro spheres, flakes, etc.), bioactive fillers, neutralizing resins, diluting resins, antibiotic agents, coloring agents, plasticizers, coupling agents, free radical generators, radiographic contrast agents, and antibiotics.

In many embodiments, the implant materials include a blended resin of DUDMA to impart strength, TEGDMA to impart flexibility, a benzoyl peroxide initiator (BPO) or any peroxide initiator that is consumed during the polymelization reaction, and at least one polymer stabilizer. The implant materials can also include a plurality of fillers and fibers. The fillers can be of the combeite type, such as the combeite filler described in U.S. Pat. Nos. 5,681,872 and 5,914,356, incorporated herein by reference in their entireties, to render the material bioactive and encourage direct bone bonding. Alternatively, the filler can be selected from a group of fillers including, but not limited to, borosilicate, silica, Wollastonite, hydroxyapatite (HA), beta-tricalcium phosphate, calcium sulfate, alumina, and the like. In embodiments where the implants further comprise fibers, the fibers can further include E-glass fibers of the composition type [$SiO_2$ CaO $Al_2O_3$ $B_2O_3$], A-glass fibers, silica, or a plurality of other fibers including but not limited to Kevlar and carbon fibers for imparting toughness and strength to the implant. In certain embodiments, the fillers and fibers are surface treated for incorporation and bonding between them and the resin. For example, the fillers and fibers can be silanated, silicone-oil treated, or provided with coupling agents such alumina, titania, or zirconia coupling agents.

In one embodiment of the present invention, the monomers, fillers, and other additives are blended together to form a paste composition. The paste compositions are easily mixed via a low speed, high shear rotary mixer. The duration of the blending operation will vary depending upon the constituents that comprise the paste composition precursors. In one embodiment, the blending of the monomers and other additives within the paste composition precursors activates the polymerization of the composition. In another embodiment, exposure to heat either during or after blending activates the polymerization. The exposure can occur in temperature ranges of about 40° C. to about 180° C. or about 60° C. to about 120° C. in some instances.

The implant materials of the present invention can be comprised of a one-paste system or combined with two or more paste compositions to form a multiple paste system. Depending upon whether the implant material is a one paste or multiple paste system determines the hardening of the material. The paste compositions of the present invention can be hardened by thermal energy, photochemical energy, and treatment by chemical process. One skilled in the art may also choose to do so in a controlled fashion. In certain embodiments wherein the implant materials comprise a one-paste system, the paste composition is hardened or cured via exposure to heat or light. Alternatively, the paste composition could be cured via gamma radiation. In some embodiments, additional exposure to gamma radiation can impart additional strength. In other embodiments wherein the implant materials comprise a multiple paste system, the paste compositions are admixed and hardened via thermal energy or heat cured. The paste compositions can also be chemically cured via catalyst or redox systems. It will be understood, however, that a wide variety of polymerization systems and materials for use therein can be employed to good advantage in connection with the present invention and all such systems are contemplated hereby. Depending upon the system that is employed, the paste composition can generally comprise heat-culling catalysts, photopolymerization, or redox (i.e. N,N(dihydroxyethyl)-p-toluidine (DHEPT), BPO, Fe(II), tertiary butyl hydro-peroxide (t-BHP)) initiators. Polymerization materials and catalytic systems known in the art and not inconsistent with the objects of this invention can be employed.

In multiple paste systems where heat curing is used to harden the composition, a catalytic system is employed such that when two components of the hardenable composition are mixed together, the catalytic action begins, leading to hardening. This system is familiar and can be applied to a wide variety of polymerizable species including many which are suitable in the present invention. Radical initiators such as peroxides, especially benzoyl peroxide (also called dibenzoyl peroxide) are conventional, economic, and convenient. A stabilizer such as butyl hydroxy toluene is customary, as is employment of co-catalysts like dimethyl-p-toluidine, N—N-substituted toluidine, and other conventional catalysts including tertiary amine structures with double bond functionality like diethyl aminoethyl methacrylate and N,N-dimethyl-p-toluidine. In general, one of the pastes incorporates both the radical initiator and stabilizer, such as a peroxide, and the other paste incorporates the accelerator, such as an amine or toluidine. Curing is initiated by an oxidation-reduction mechanism upon mixing the two pastes together.

In paste systems where culling via exposure to heat or other means is used to harden the composition, a photoinitiation system can be included with the hardenable compositions and the same caused to be activated by exposure to actinic light of a suitable wavelength. Both ultraviolet and visible photocuring systems are known for use in restorative surgery and dentistry and any such system can be employed herein. Exemplary systems are described in U.S. Pat. No. 4,110,184 to Dart et al., U.S. Pat. No. 4,698,373 to Tateosian et al., U.S. Pat. No. 4,491,453 to Koblitz et al., and U.S. Pat. No. 4,801,528 to Bennett, which are incorporated herein by reference in their entireties to provide enablement for such known systems.

A particularly useful system employs visible light culling, thus avoiding the potential danger inherent in culling with ultraviolet radiation. Visible light culling has been well refined in the dental field and the same can also be applied to restorations of bony tissues. Quinones, as a class, find wide utility as photochemical initiators for visible light sensitizing systems, preferably when the same are admixed with tertiary amines. Some skilled artisans may prefer that an alpha diketone (quinone) such as camphoroquinone or biacetyl be admixed with an amine reducing agent such as n-alkyl dialkanolamine or trialkanolamine. Other such photo-initiator systems include a 2-benzyl-2-(dimethylamino)-4'-morpholinobutyrophenone, or 50%/50% weight composition of 2-hydroxyethyl-2-methyl-1-phenyl-1-propanone and diphenyl(2,4,6-trimethylbenzyl)phosphine oxide. However, other such curing systems or combinations of curing systems can also be employed with the materials of the present invention.

In some embodiments, one or more fillers are blended into the paste composition after the monomers and other additives comprising the resin blend have been combined. The fillers are preferably added incrementally to avoid binding during the blending process. A vacuum may be applied during blending to minimize porosity and dusting. In embodiments comprising multiple fillers, such as E-glass fibers, borosilicate fillers, silica fillers, and combeite fillers, the E-glass fibers may be added first followed by the remaining fillers in a designated order. Alternatively, one or more fillers may be pre-blended together prior to incorporation into the resin blend. After the filler has been combined with the resin mixture, the completed paste mixture may be agitated via a vibrating table, ultrasonic, or similar means for a period of time ranging from about 5 minutes to about 60 minutes to further reduce porosity. A vacuum may be applied during the agitation step.

Although the uses described above are exemplary for the present invention, there are other embodiments that may be foreseen by those skilled in the art. Within the dental field, the implants of the present invention can have use as dental crowns (temporary or crown) and dental implants, including Maryland bridges. The implant materials can also have use as implants for other areas of the animal body. Such foreseeable implants include cochlear, cranial, tumor, sternum, or other custom implants that can be MRI compatible or functional shapes made for the body. Other embodiments can be used for formulation of universal plates for orthopedic use, bone screws, rods, and pins for orthopedic use (IM nails, femoral rods or plugs, long bone fractures, etc.), tendon anchors, suture anchors and tacks, graft retainers, and marrow sampling ports.

Other uses include non-articulating artificial joint surfaces, sensor anchors or housings, bone spacers or wedges (tibial, femoral), cartilage beds or anchors, or drug delivery. It is also foreseeable that the implant materials can be used in methods for repairing the iliac harvest site. The materials can be incorporated into drug delivery beads into bone or in interbody balls. There can also be applications for mandibular joints (TMJ) and orbital reconstruction.

One embodiment of the present invention involves machining of the implantable materials into morsels for use in methods to treat segmental defects. The morsels can also be used for minimally invasive load bearing applications. The material can be made into a mesh for postero-lateral fusion or cages for other materials. Other embodiments involve the material being used as a cannulated screw with peripheral holes used in methods for treating vertebral augmentation. The present invention can have embodiments involving synthetic bones.

II. Cervical Implant

The bioactive implant material may be formed into a variety of shapes for use as spinal implantation or spinal fixation devices. In one embodiment, the implant material is preferably formed into a cervical implant device. While the present invention is described in terms of the implant material of the present invention, it is understood that other materials may be used to form the cervical implant of the present invention.

FIGS. 1 through 4 illustrate various aspects of one embodiment of the cervical implant 10 of the present invention. Implant 10 may vary is size to accommodate differences in the patient's anatomy. The implant 10 is comprised of an anterior side 60, a posterior side 70 opposing the anterior side 60, and a pair of opposing sidewalls 40. The anterior side 60, the posterior side 70, and the sidewalls 40 are generally outwardly curved in transverse cross-section. The curved sides are convex as viewed from the outside of the implant 10. The anterior side 60, the posterior side 70, and the sidewalls 40 join at points that generally define, in transverse cross section, a trapezoid. The transverse cross-section, as used herein, is the plane perpendicular to the z-axis. As used herein, a trapezoid is a quadrilateral having two parallel sides, or any shape having the form of a trapezoid. The present invention employs geometric shapes to illustrate a preferred embodiment, but the present invention is not limited to such shape. Rather, the present invention broadly encompasses any variation in the claimed shapes within the spirit of the disclosure, including (for example) configurations in which gradually merge with adjacent sides and non-uniform shapes that vary according to the transverse or longitudinal cross section.

The implant also comprises a top surface 20 and a bottom surface 30 that is generally opposite the top surface 20. The top 20 and bottom surfaces 30 can also be convex, or outwardly curved, in the longitudinal cross-section. The curvature and shape of each side grants the implant superior anatomical compatibility. The surfaces also maximize contact with cortical bone to minimize subsidence of the implant into the endplates.

The top 20 and bottom 30 surfaces further include a plurality of projections 25, preferably wave-like or scalloped in shape (i.e., pointed apex with rounded valleys), for gripping adjacent vertebrae. The scalloped shape tooth design eliminates the stress concentration typically associated with other tooth designs and more evenly distributes the compressive physiologic loads from the bone to the implant. The projections 25 can be substantially uniform, upwardly protruding ribs. One skilled in the art would recognize these projections 25 as being substantially uniform, upwardly protruding, elongated ribs separated by concave channels. In alternative embodiments, the projections are randomly disposed or, in other words, situated in various directions. These projections 25 may also be upwardly protruding spikes. The wave-like shape of the projections 25 increases the surface area of the implant for maximal vertebral contact. Further, the wave-like projections 25 provide significant resistance to expulsion and retropulsion. In certain preferred embodiments, the projections 25 have an angular pitch of between 1.75 degrees to 1.9 degrees, a minimum depth of 0.022 inches, and an internal radius of about 0.022 inches. Other dimensional sizes of the projections 25 would not depart from the present invention including upwardly protruding spikes.

FIGS. 3a and 3b illustrate two alternative embodiments of the present invention. FIG. 3a illustrates implant 10 wherein the wall of the anterior 60 side has greater height than the wall of the posterior 70 side. The implant 10 of FIG. 3a has a lordotic angle. FIG. 3b illustrates implant 10 having no lordotic angle wherein the height of the wall for the anterior 60 side is equal to the wall height of the posterior 70 side. Due to the variety of machinations that may be used to make the implants of the present invention, minute variations may exist in the height of the anterior 60 and posterior sides that would not render them exactly the same height. Preferable lordotic angles fall in the range of about −20 degrees to about +20 degrees.

Figure 4:
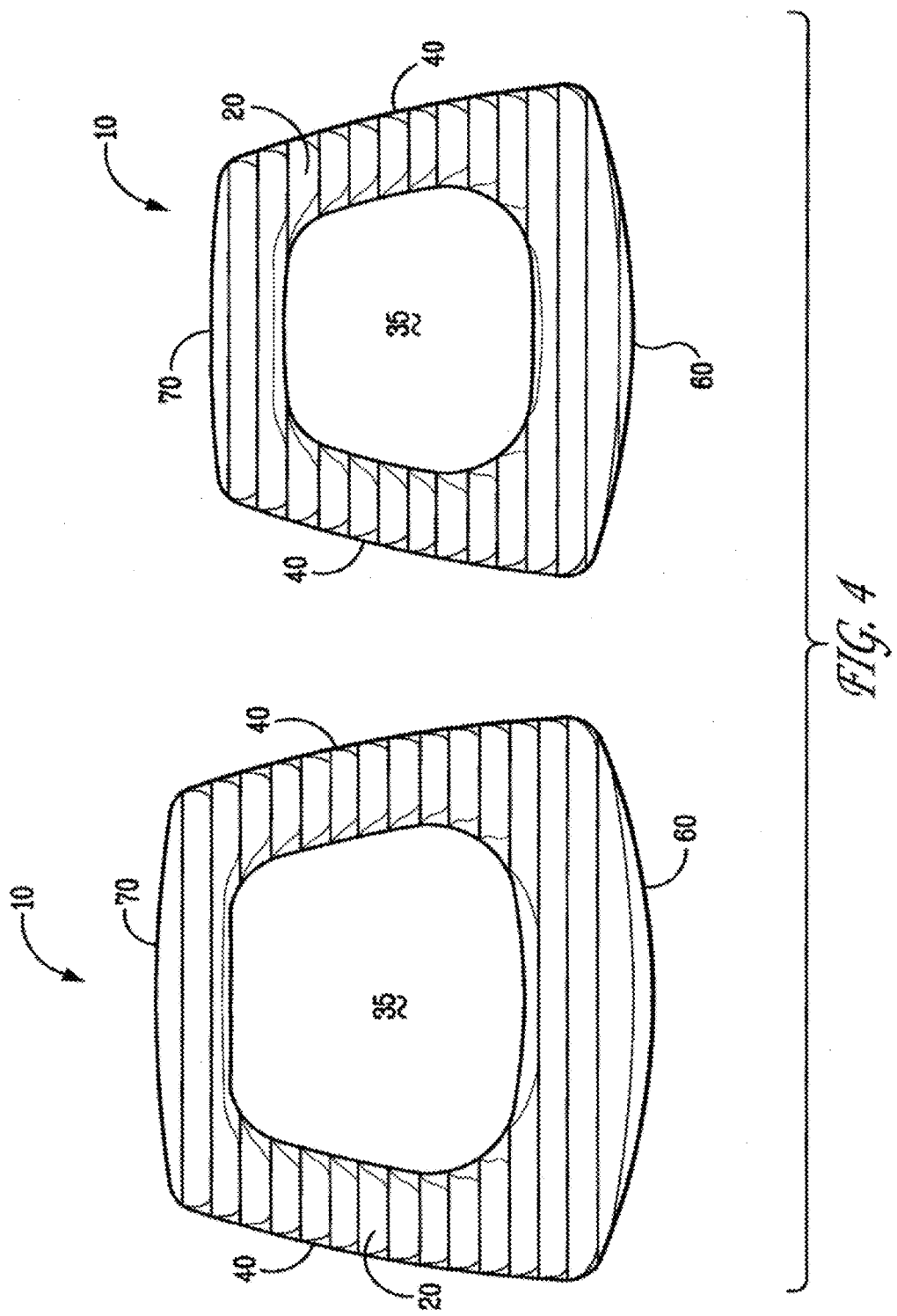
FIG. 4 provides a planar view illustrating the substantially trapezoidal shape of the top and bottom surfaces of the cervical implant 10.

In FIG. 4, the implant 10 has a trapezoidal shape defined by the sidewalls 40, anterior 60, and posterior 70 sides. This shape maximizes contact with cortical bone. In preferred embodiments, the top 20 and bottom 30 surfaces are substantially identical in size and shape. The shape also allows one skilled in the art to place graft material within a major recess 35 bordered by the sidewalls 40, anterior 60, and posterior sides. This major recess 35 is formed in the body and is in communication with at least one of the top or bottom surfaces. A preferred embodiment has the major recess 35 having a through-aperture that is in communication with both top 20 and bottom 30 surfaces.

The implant also has a handling feature that may comprise at least one pair of elongated side recesses 43 and 53 for receiving forceps and a front recess 63 for receiving an impaction tool. The front recess 63 may be used in conjunction with the anterior side 60 and front opening 65 as to communicate with an implant holder or insertion tool. The front recess 63 may be elongated with a major axis that is substantially transverse. The front recess 63 may have an aperture, the front opening 65, formed therein. This handling feature allows for handling and insertion of the spinal implant using instruments such as forceps. In some embodiments, the handling feature consists of only the front recess 63. In FIGS. 1 through 3, the sidewalls 40 further comprise side recesses 43 and 53 that may mate with an instrument to aid in insertion or removal of the implant. The sidewalls 40 also comprise at least one opening 45 (FIGS. 1 and 3) to allow fluid to enter the major recess 35 after insertion. Graft material may be supplied with blood and other biologic fluids through the openings 45. In other embodiments, the handling feature consists of only the side recesses 43 and 53. The surfaces of these recesses may be textured with an anti-skid material to prevent slippage of the insertion tool.

In FIGS. 1 and 2, the front recess is used to prevent rotation of the implant. The front recess 63 and a front opening 65 can mate with an implant insertion tool. The front recess 63 may be comprised of some other geometry suitable to prevent the implant from rotating on the end of the implant insertion tool during insertion or removal of the implant. In certain embodiments, the front opening 65 may be threaded to mate with a corresponding implant insertion tool. In other embodiments, the front recess 63 is eliminated.

Figure 5:
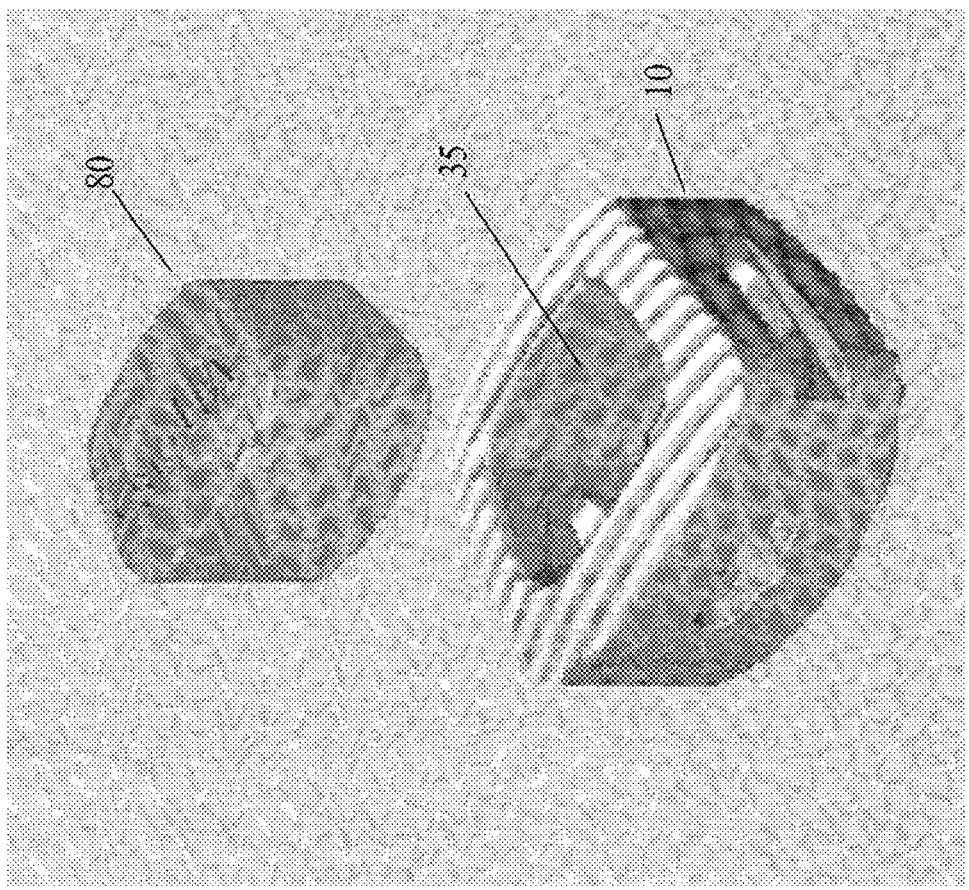
FIG. 5 provides an exploded view of the cervical implant 10 with a synthetic graft material.

FIG. 5 provides an exploded view of the implant 10 showing graft material 80 being placed in the major recess 35. Graft material may be comprised of allograft material, autograft material, or synthetic materials that have similar properties to allograft or autograft materials. The synthetic graft material is preferably comprised of a biocompatible, osteoconductive, osteoinductive, or osteogenic material to facilitate the formation of a solid fusion column within the patient's spine. One such example of such a synthetic graft material is VITOSS® Synthetic Cancellous Bone Void Filler material, which is manufactured by Orthovita, Inc. of Malvern, Pa. To foster bone fusion, the VITOSS® calcium phosphate material may be saturated with the patient's own bone marrow aspirate, or therapeutic material such as growth factor, proteins, bone marrow aspirate and other materials such as those disclosed in U.S. Pat. No. 7,045,125, issued May 16, 2006, incorporated herein by reference. It should be noted that in preferred embodiments, the posterior side 70 does not have an opening therethrough. This facet of the design is a safety feature implemented to prevent leakage of graft materials placed in the major recess 35 into the spinal canal.

Figure 6:
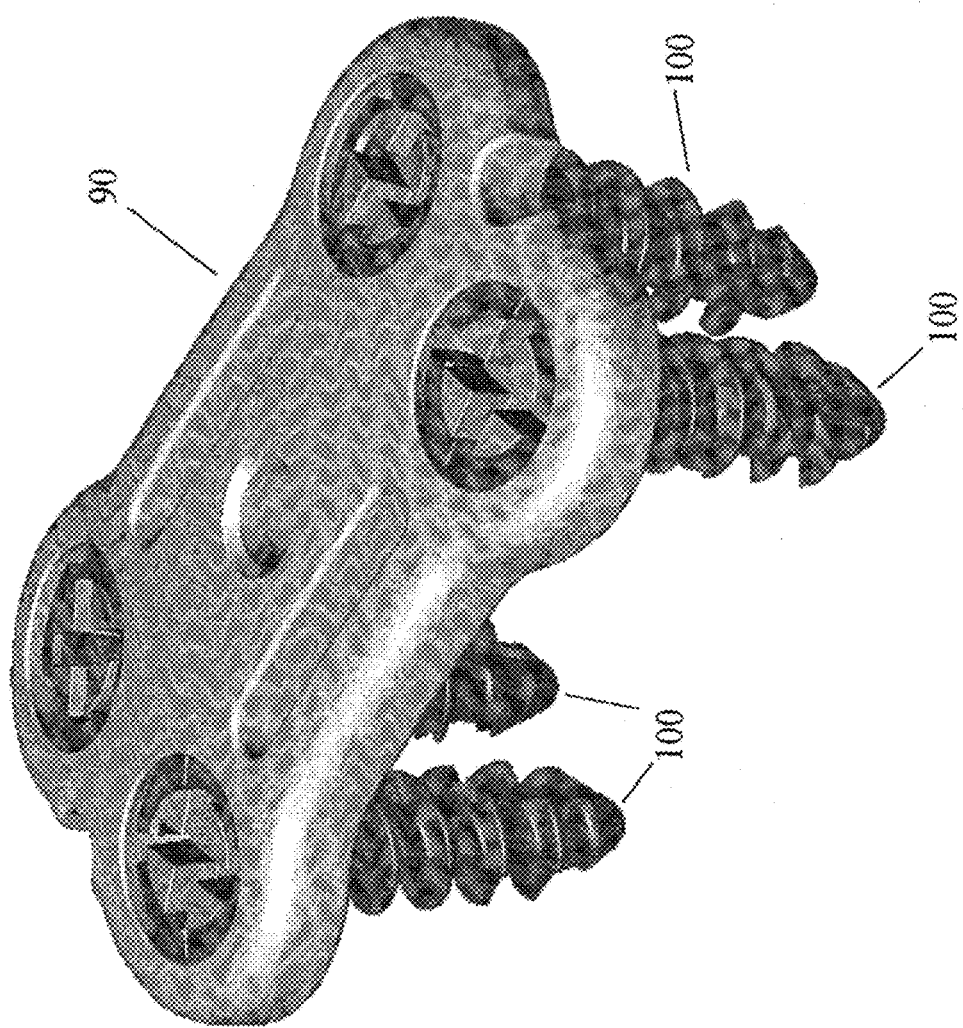
FIG. 6 provides an isometric view of a cervical plate and fastener assembly 100.
Figure 7:
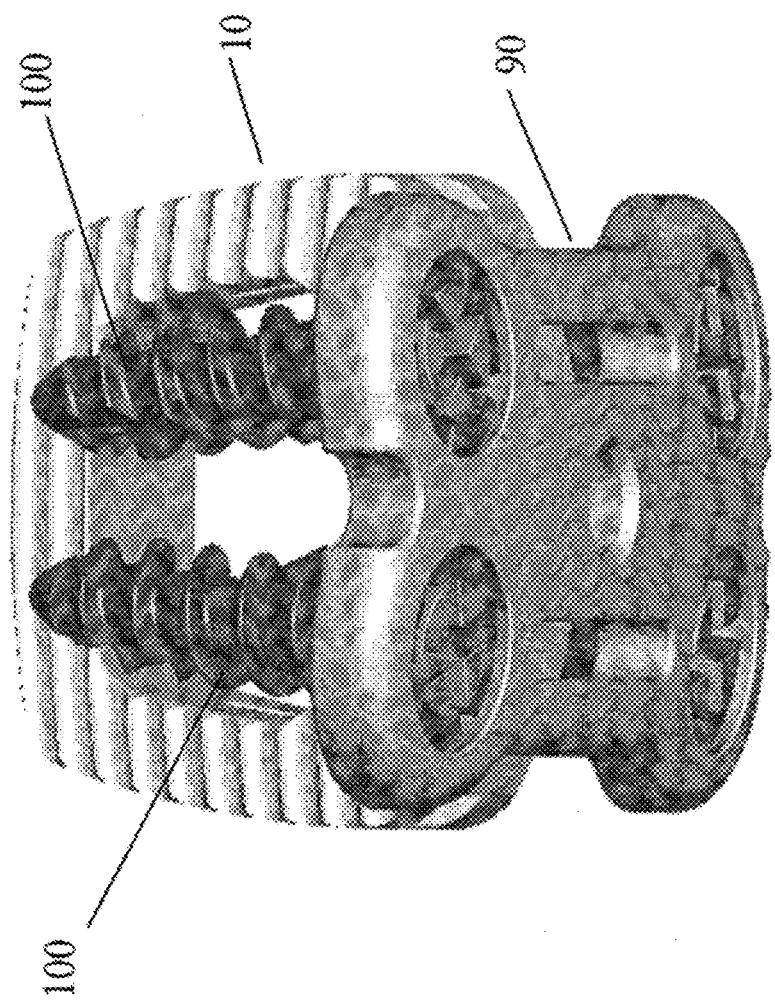
FIG. 7 provides an isometric view of the cervical implant 10 with a cervical plate and fastener assembly 100.
Figure 8:
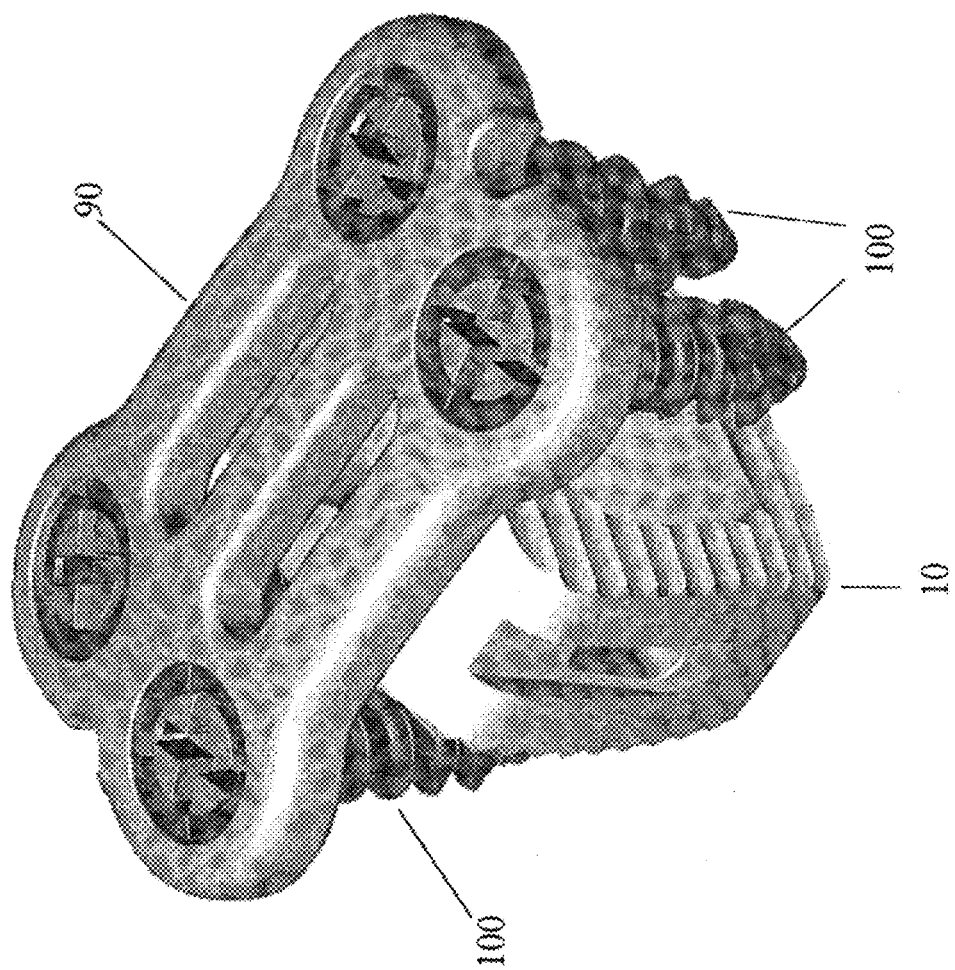
FIG. 8 provides another view of the cervical implant 10 with the cervical plate and fastener assembly 100.

FIGS. 6 through 8 show a plate 90 and fastener 100 assembly that may be used in conjunction with implant 10. The plate and fastener assembly may facilitate fusion of adjacent vertebrae by stabilizing the implant in place between the vertebrae. Fasteners 100 may be comprised of screws, pins, nails, and the like. They are inserted into openings within plate 90 to engage the adjoining vertebral bodies. Upon insertion, one pair of fasteners is inserted in the upper vertebral body and one pair is inserted in the lower vertebral body.

Figure 9:
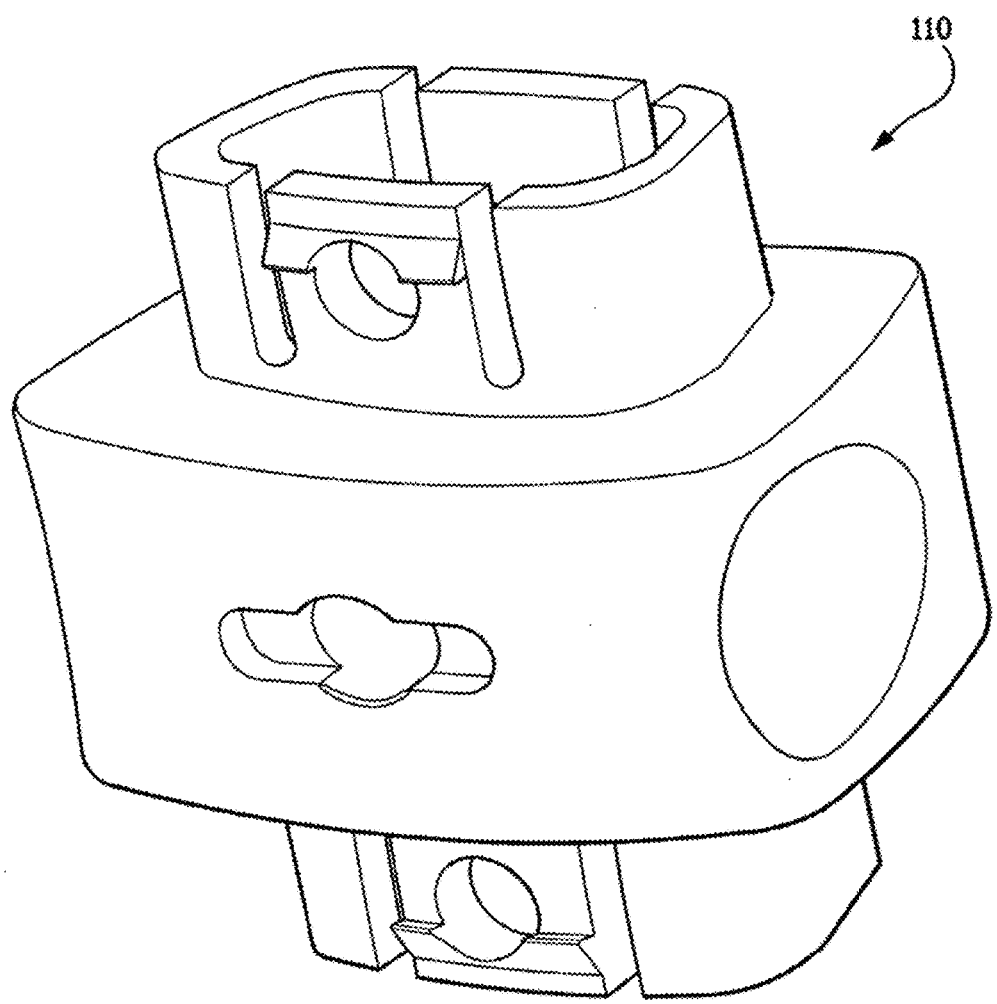
FIG. 9 provides an isometric view of an embodiment of a connector accessory 110 that may be used in connection with the cervical implant 10.
Figure 10:
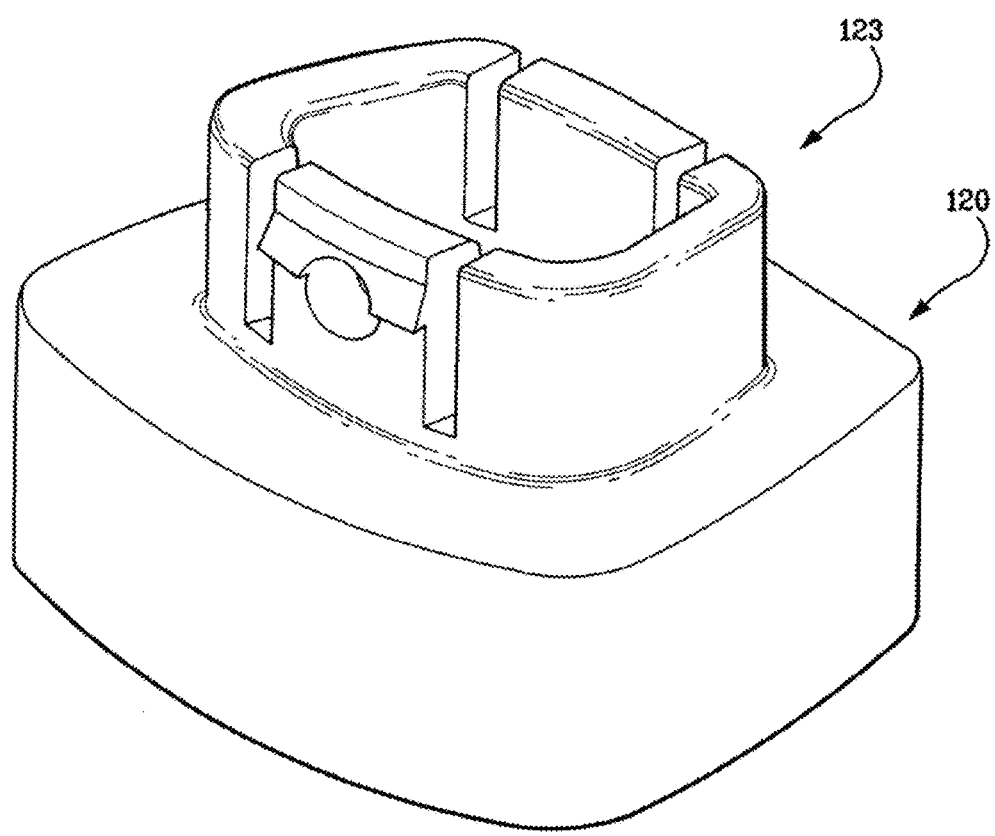
FIG. 10 provides an isometric view of another embodiment of a spacer accessory 120 that may be used in connection with the cervical implant 10.
Figure 11:
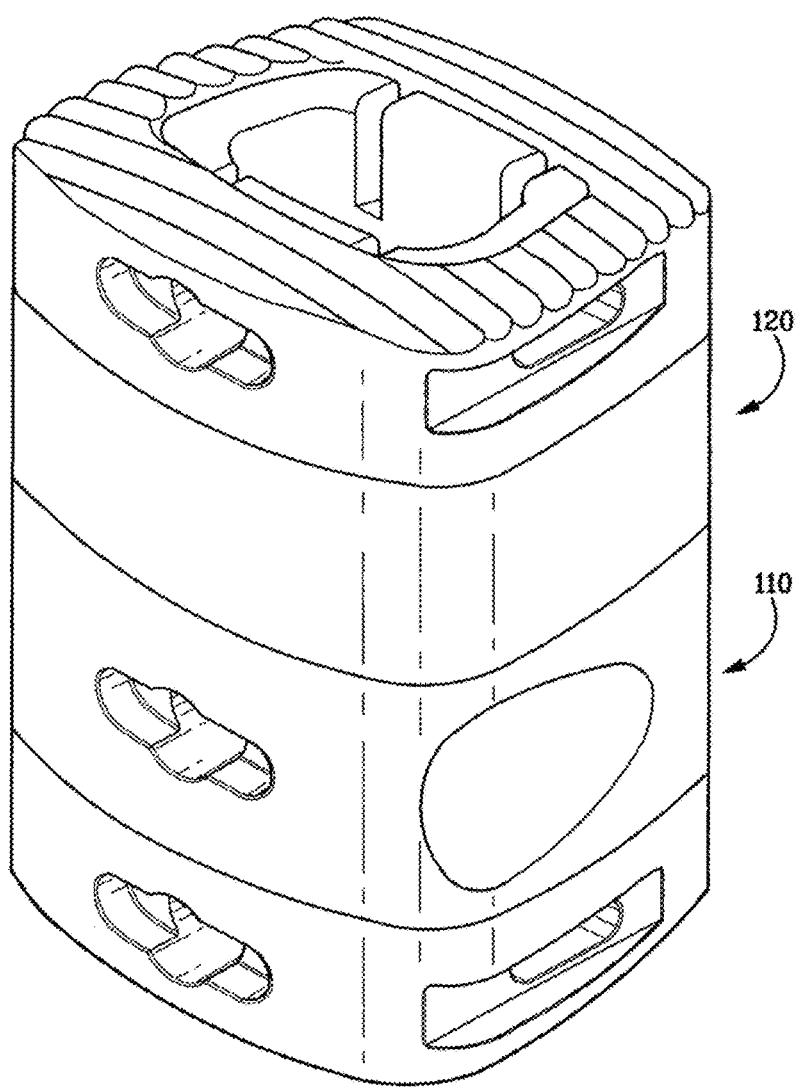
FIG. 11 provides an isometric view of the connector accessory 110 and the spacer accessory 120 that may be used to mate two cervical implants 10.

FIGS. 9 through 11 show accessories 110 and 120 that are used to connect one or more implants 10 as shown in FIG. 11. Accessories 110 and 120 may be used in corpectomy procedures in which the surgeon removes one or more vertebrae and needs to restore the spine to its former height. In FIG. 9, accessory 110 has two male ends that may engage, for example, the major recess 35 of implant 10 or the female end of accessory 120. In FIG. 10, accessory 120 has a male end 123 and a female end that allows implants to be joined together as shown in FIG. 11. Accessories 110 and 120 may be joined together with implants 10 via snap or compression fit via one or more flexible tabs, fasteners, adhesives, or other means.

III. ALIF Implant

The bioactive material of the present invention may also be formed into an implant suitable for ALIF procedures. ALIF implant devices are generally suitable for implantation in the lumbar regions of the spine.

Figure 12:
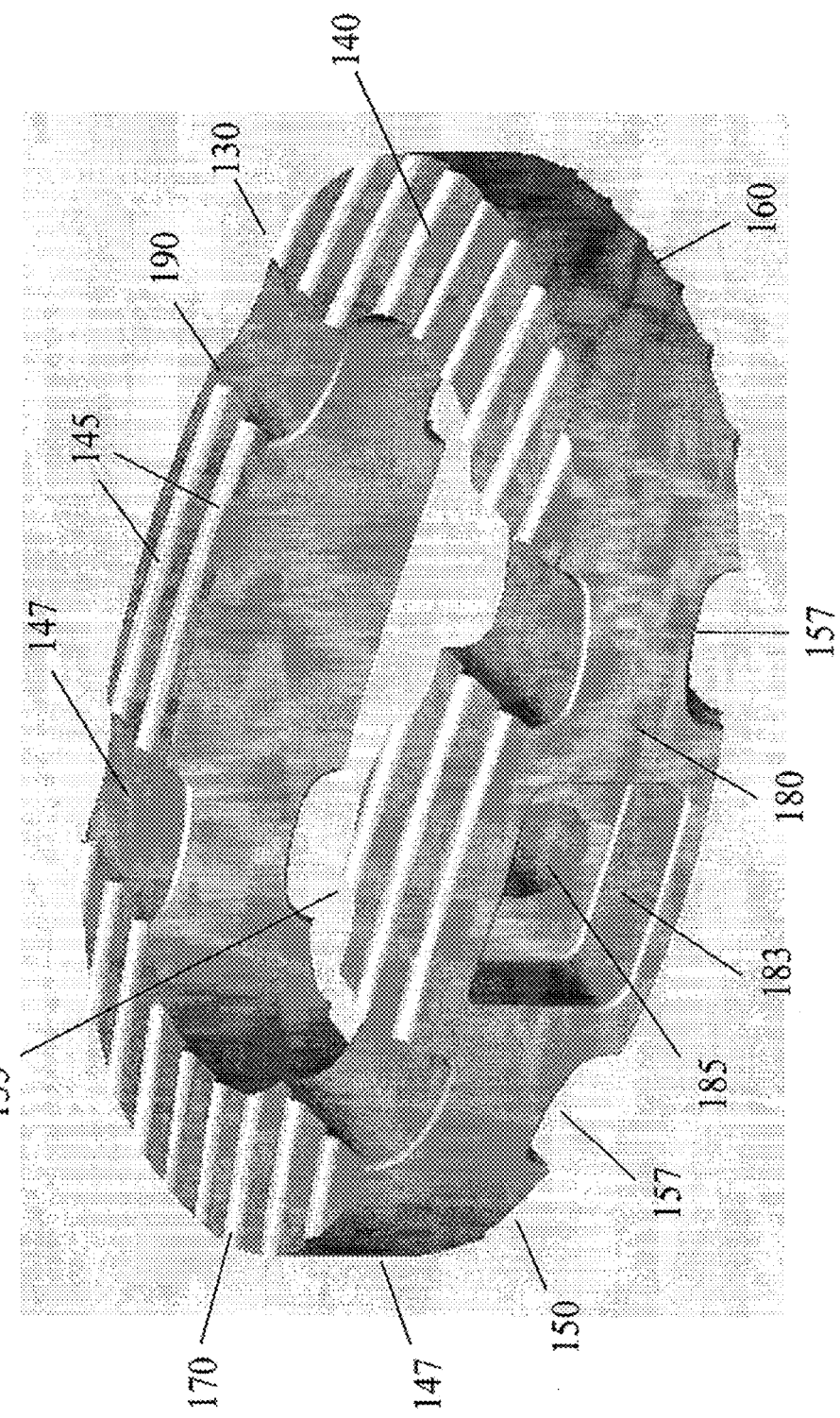
FIG. 12 provides an isometric view of one embodiment of the ALIF implant 130.
Figure 13:
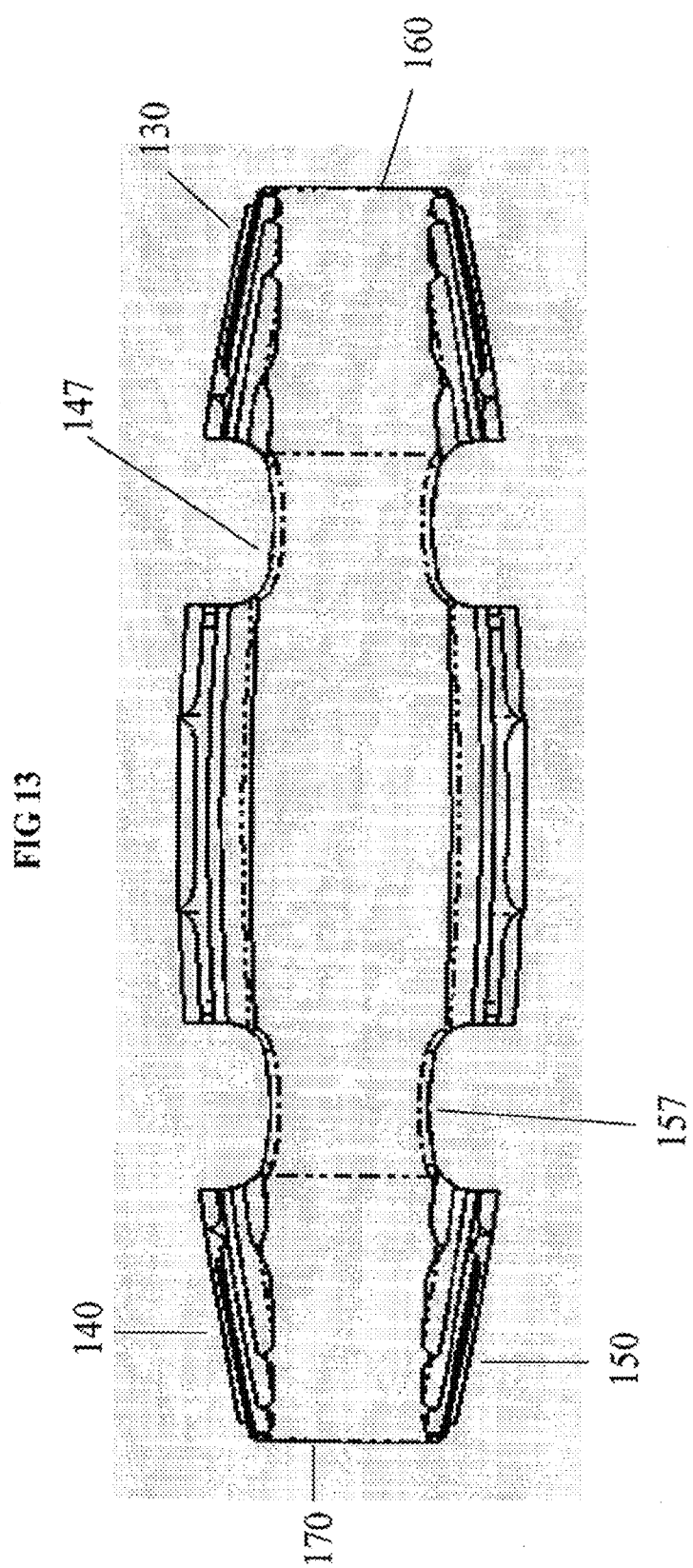
FIG. 13 provides a front view illustrating the anterior side of the ALIF implant FIG. 14 provides a side view illustrating the medial side or lateral side of the ALIF implant 130.
Figure 14:
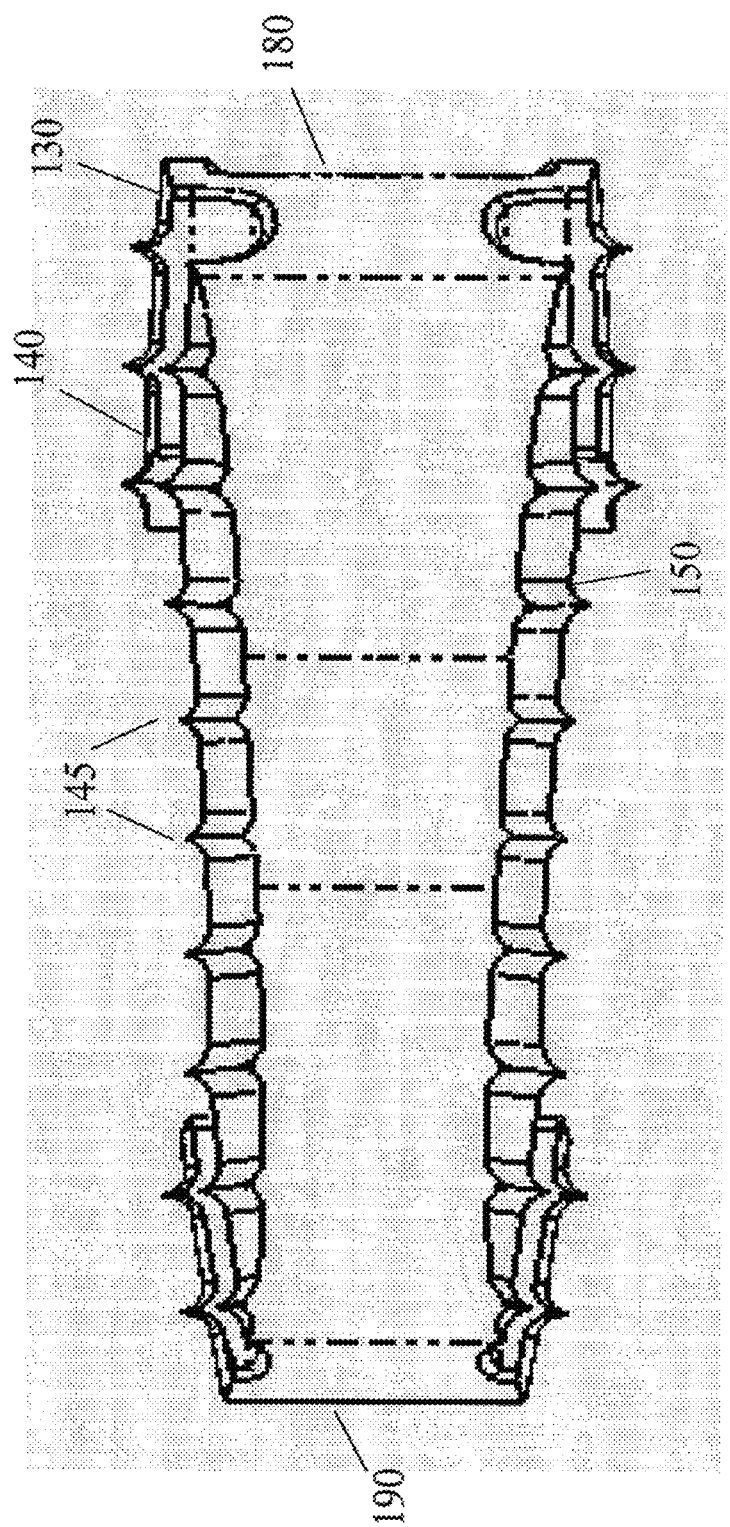

FIGS. 12 through 14 depict one embodiment of the ALIF implant 130 of the present invention. Like the cervical implant of the present invention, implant 130 may be in a variety of different sizes to accommodate differences in the patient's anatomy or the location of the spine that implant 130 will be inserted. The body may substantially form an oval shape in the longitudinal cross-section. The implant is a body comprising a bioactive substance and further comprising: an anterior side 180, a posterior side 190 opposing the anterior side 180, and a pair of opposing sidewalls 160, said sidewalls 160 being generally outwardly curved or generally "c-shaped." The anterior 180 and posterior 190 sides may be parallel and in others they are outwardly curved. The implant also has a top surface 140 and a bottom surface 150, both surfaces coupled with the sidewalls 160. Top surface 140 and the bottom surface 150 form plural projections 145 for enhancing interaction with a synthetic or natural vertebral body. At least one major recess 135 is formed in the body in communication with at least one of the top surface 140 and the bottom surface 150.

Also in FIGS. 12 and 14, top 140 and bottom 150 surfaces further include a plurality of projections 145, preferably wave-like or scalloped in shape, for gripping adjacent vertebrae. These projections share the same characteristics of the plurality of projections 25 noted in the description of the cervical implant.

FIG. 14 illustrates one embodiment of the present invention. FIG. 14 illustrates implant 130 having a lordotic angle: The lordotic angle can range from −20 degrees to +20 degrees.

Similar to the cervical implant 10, the ALIF implant has a major recess 135 that forms a through-aperture. This shape maximizes contact with the cortical bone in the thoracic and lumbar regions. In preferred embodiments, the top 140 and bottom 150 surfaces are substantially identical in size and shape. The major recess 135 also maximizes the chances of fusion because graft or resorbable material may be packed within implant 10. It should be noted that in preferred embodiments, posterior side 190 does not have an opening therethrough. This is to prevent leakage of graft materials from the major recess 135 into the spinal canal.

The implant also has a handling feature comprising recesses 147 and 157 along the top 140 and bottom 150 surfaces extending from either the anterior 180 and posterior 190 sides that act as guide rails and at least one recess 185 in the anterior or sidewalls 160 for receiving an impaction tool. FIGS. 12 and 13 show the recesses 147 and 157 that act as guide rails. The guide rails mate with an instrument, such as a parallel distraction instrument, to aid in insertion or removal of the implant. The plurality of guide rails holds the implant securely and may allow the surgeon to insert the implant more evenly.

FIG. 12, shows the implant 130 having a front recess 183 used as an anti-rotation recess and a front opening 185. The front recess 183 and opening 185 share the same characteristics as the front recess 63 and front opening 65 of the cervical implant described earlier.

Figure 15:
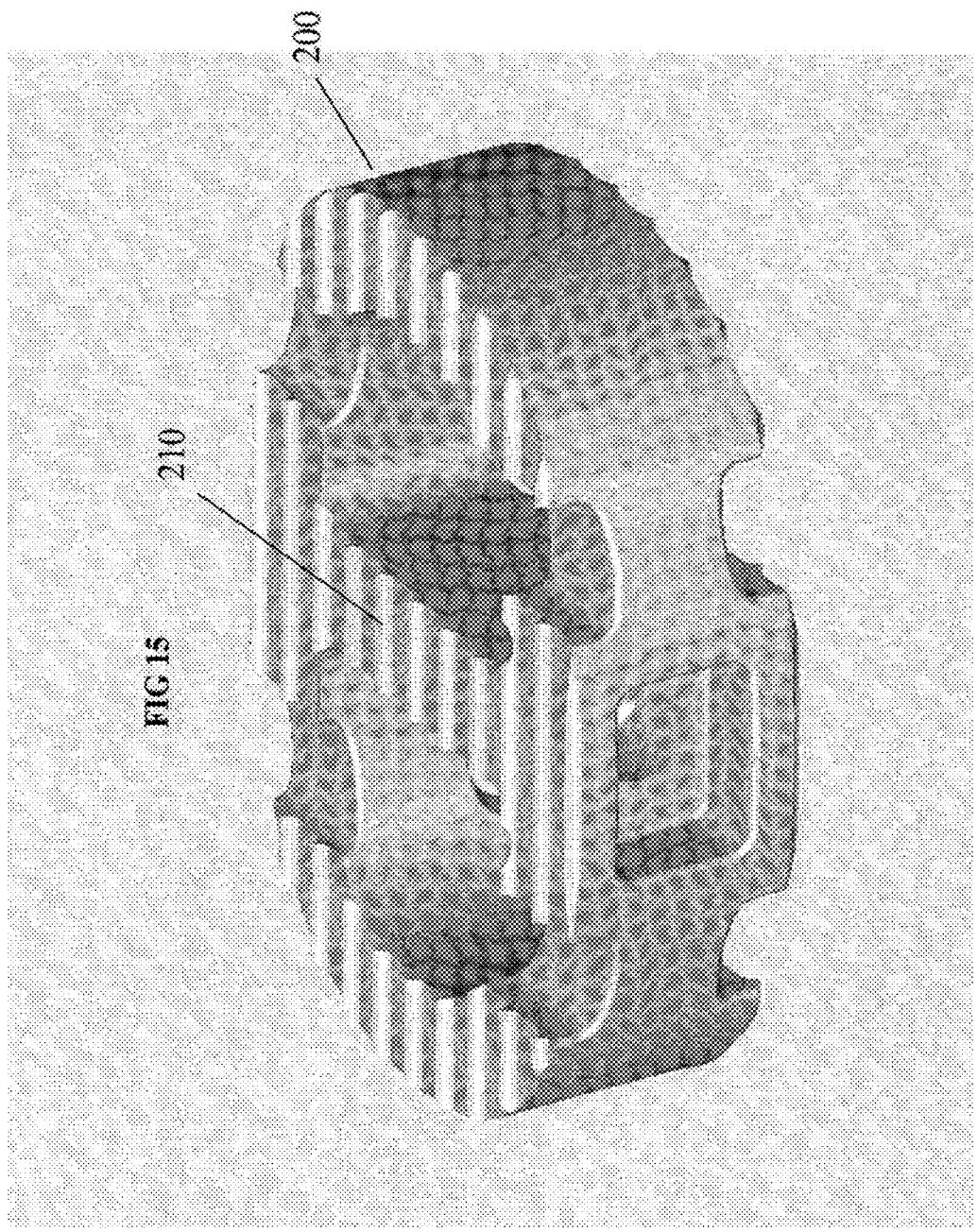
FIG. 15 provides an isometric view of an alternate embodiment of the ALIF implant 200.
Figure 16:
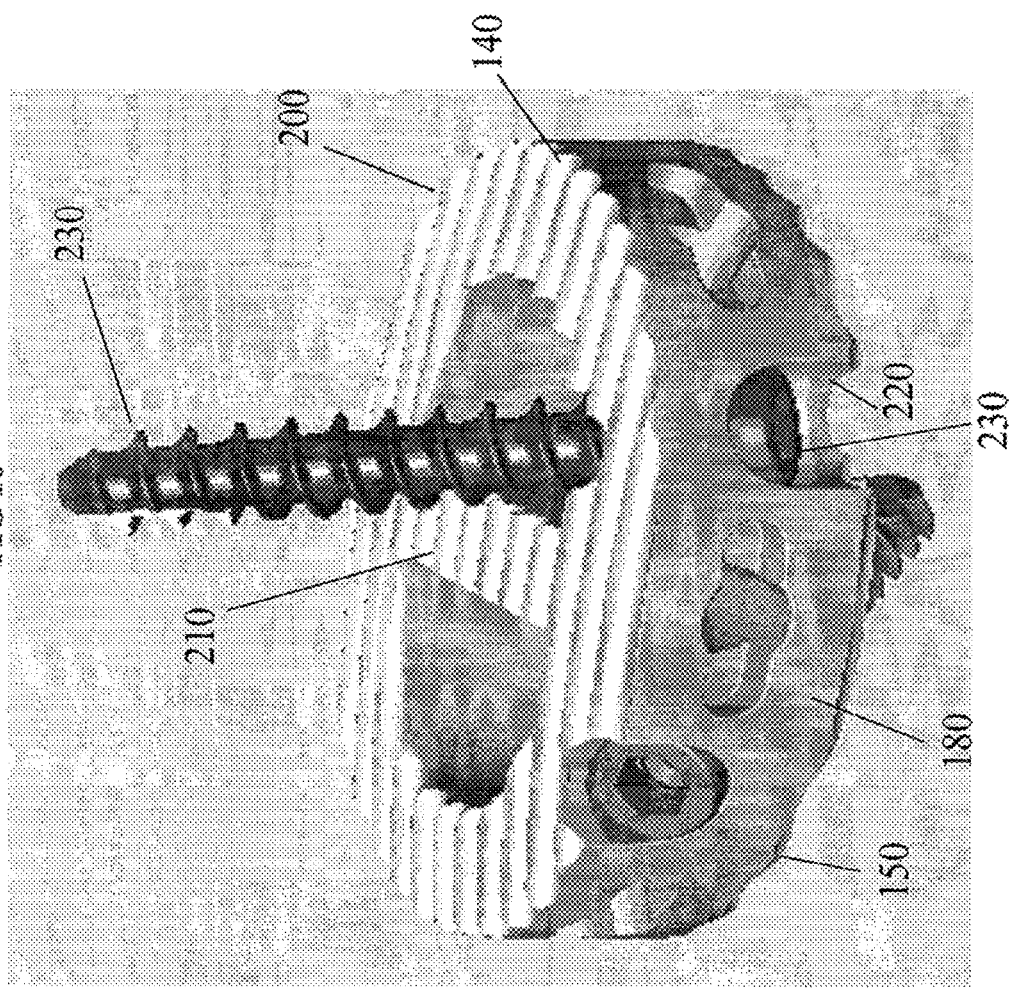
FIG. 16 provides an isometric view of the ALIF implant 200 that includes a fastening feature.
Figure 17:
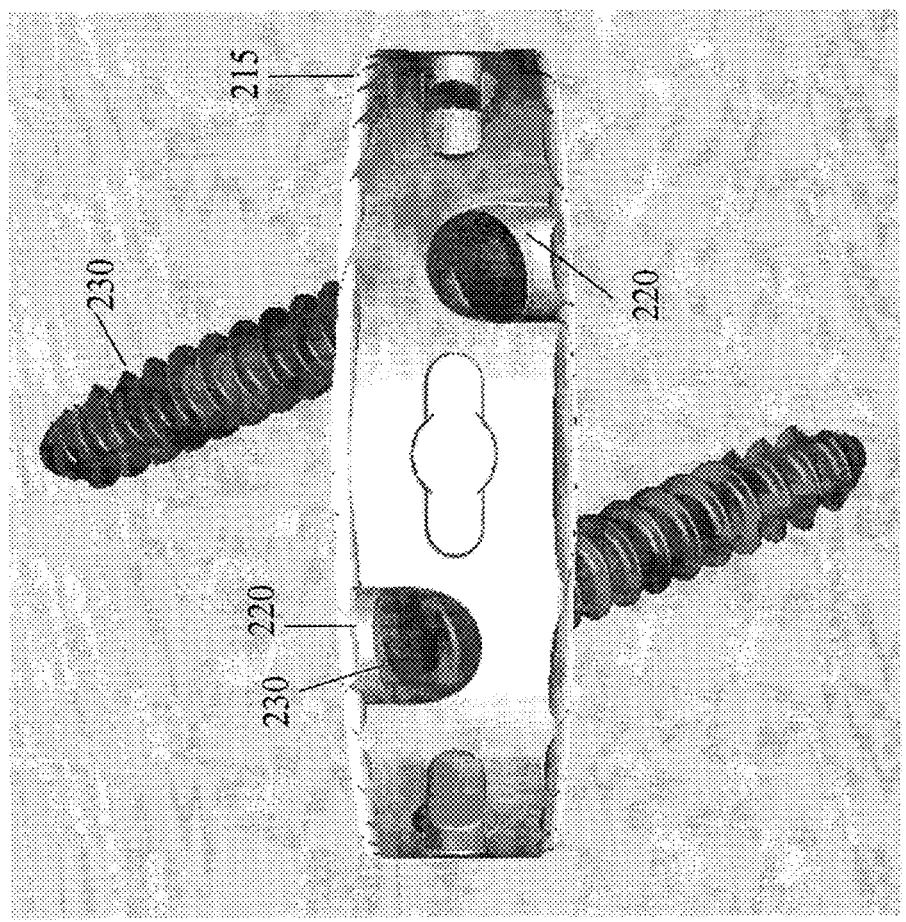
FIG. 17 provides a front view of the ALIF implant 200 and a fastening feature.
Figure 18:
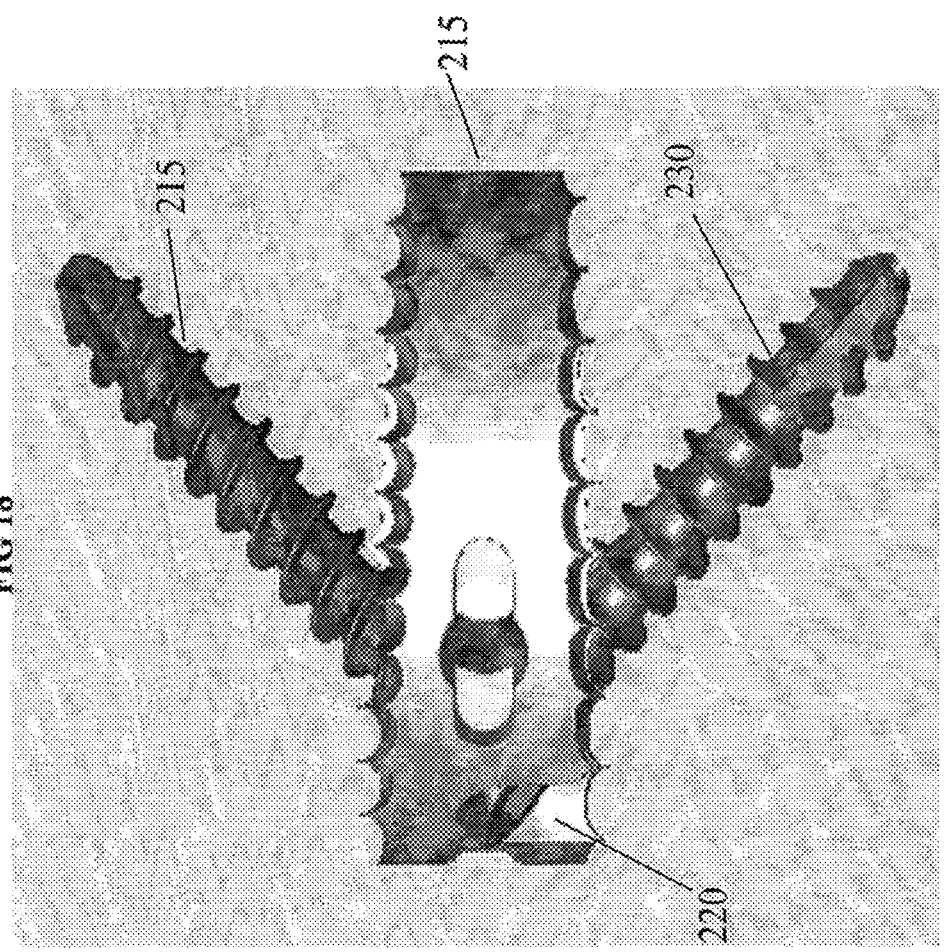
FIG. 18 provides a side view of the ALIF implant 200 and a fastening feature.
Figure 19:
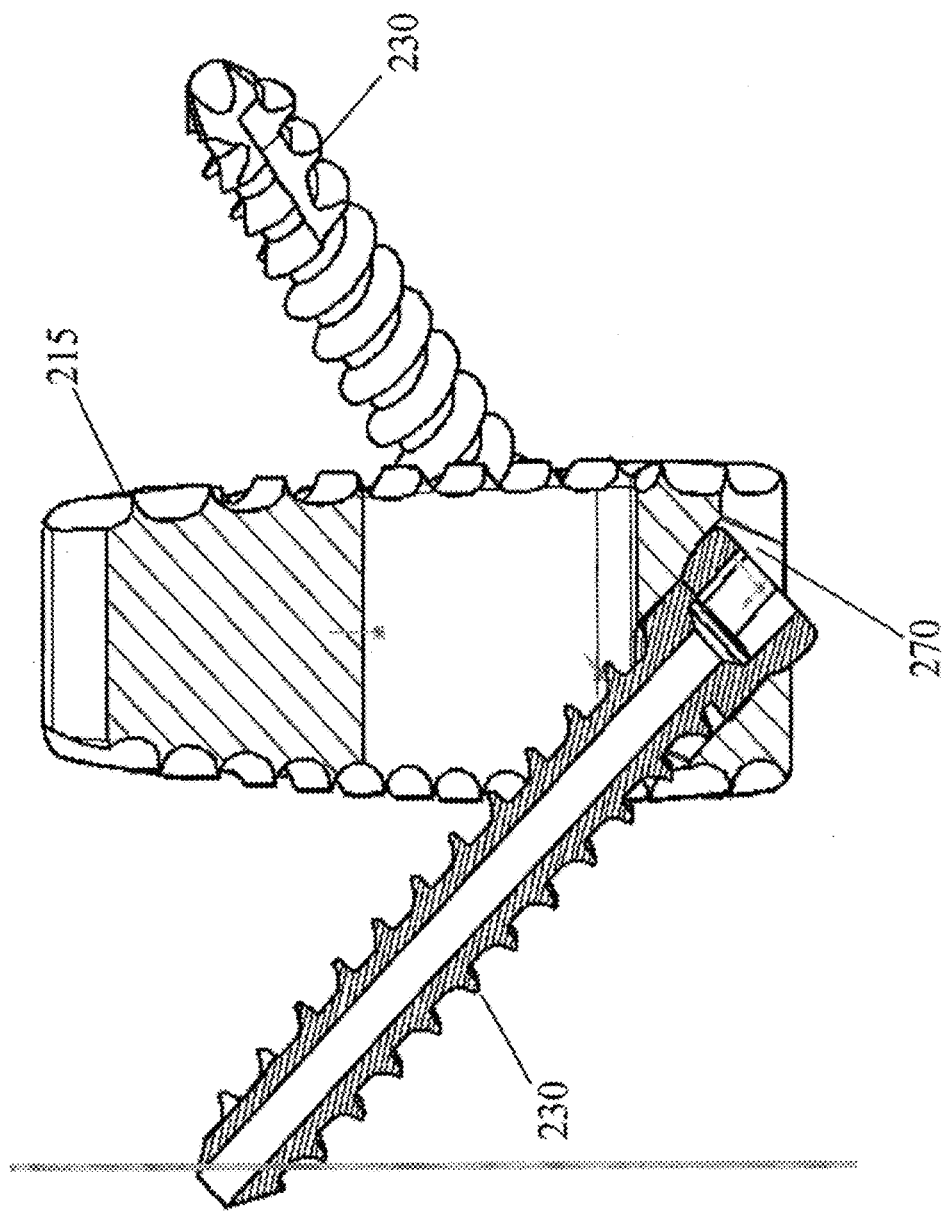
FIG. 19 provides a cross-sectional view of the ALIF implant 200 and a fastening feature.

FIG. 15 provides an isometric view of an alternative embodiment 200 of the ALIF implant of the present invention. Implant 200 includes a strut 210 that divides the major recess 135 into two through-apertures to provide support during anterior impaction of the implant during insertion. A strut 210 that has the top 140 and bottom 150 surfaces with projections 145 separates the through-apertures.

FIGS. 16 through 19 provides yet another embodiment of the present invention in which an ALIF implant 215 or implant 200 further includes a fastening feature. The fastening feature comprises at least one through-aperture 220 in communication with the anterior 180 side and either the top 140 or bottom 150 surface for insertion of fasteners 230 that communicate with a synthetic or natural vertebral body either below or above the implant. This feature includes a plurality of openings 220 on the anterior side of implant 200 for receiving fasteners 230. Fasteners 230 may include, but are not limited to, screws, pins, nails, or any other fixation devices. In certain preferred embodiments, openings 220 are angled to allow fasteners 230 to move at varying angles up and in or down and in. An angle in some embodiments that may be preferred is below about 90 degrees. In others, and angle of about 45 degrees may be preferred. Fasteners 230 help to anchor implant 215 since the upward tilted fastener is inserted into the upper vertebral body and the downward tilted fastener is inserted into the lower vertebral body.

IV. PLIF Implant

The bioactive material of the present invention may also be formed into an implant suitable as for PLIF procedures. PLIF implant devices are generally suitable for implantation in the lumbar regions of the spine.

Figure 20:
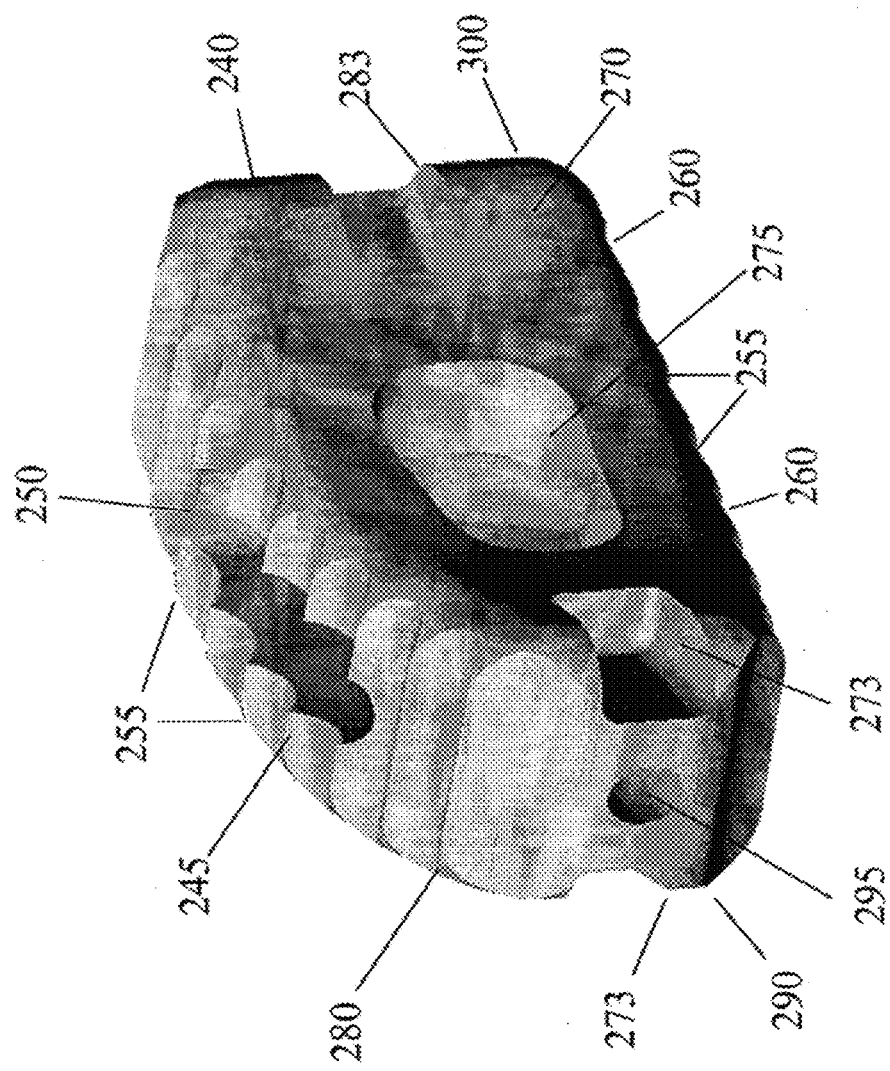
FIG. 20 provides an isometric view of one embodiment of the PLIF implant 240.
Figure 21:
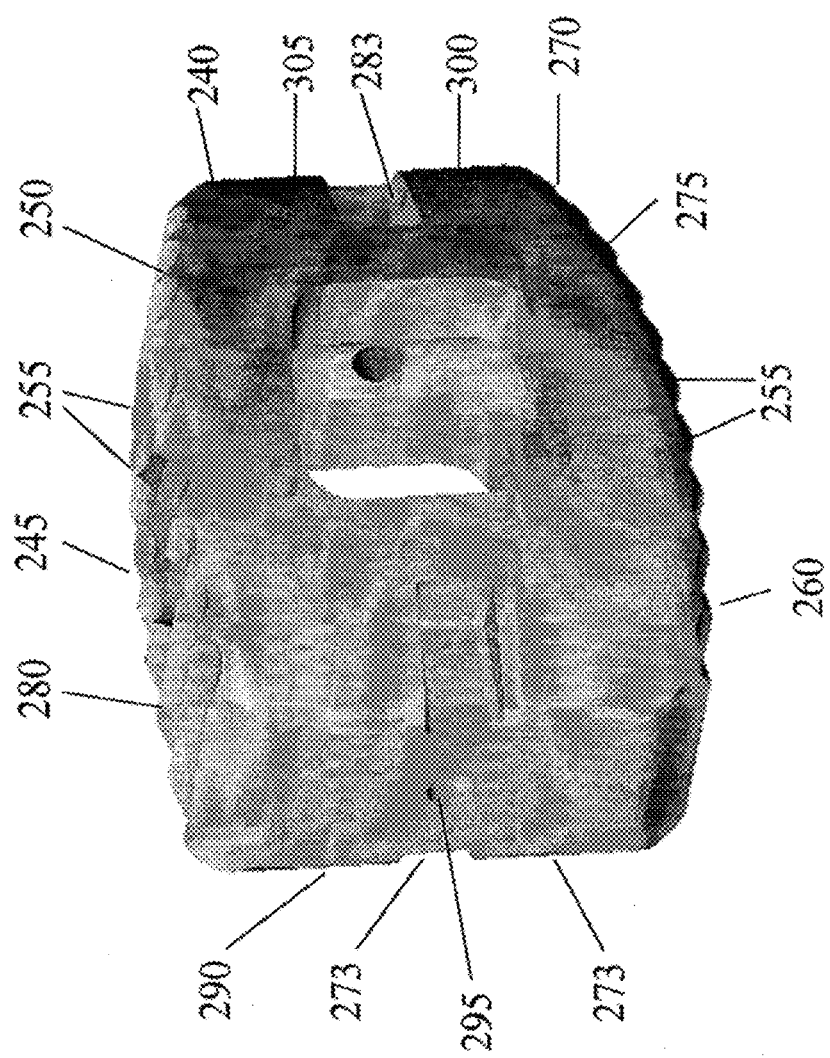
FIG. 21 provides an isometric, side view of another embodiment of the PLIF implant 240.
Figure 22:
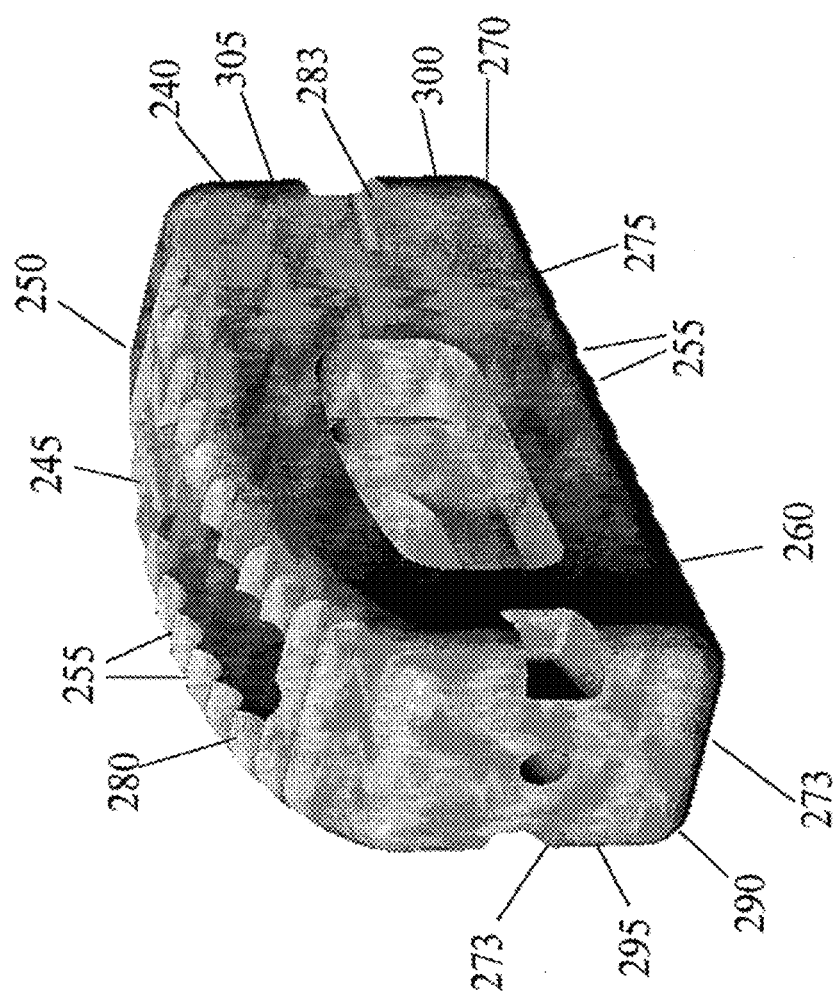
FIG. 22 provides an isometric view of yet another embodiment of the PLIF implant 240.
Figure 22A:
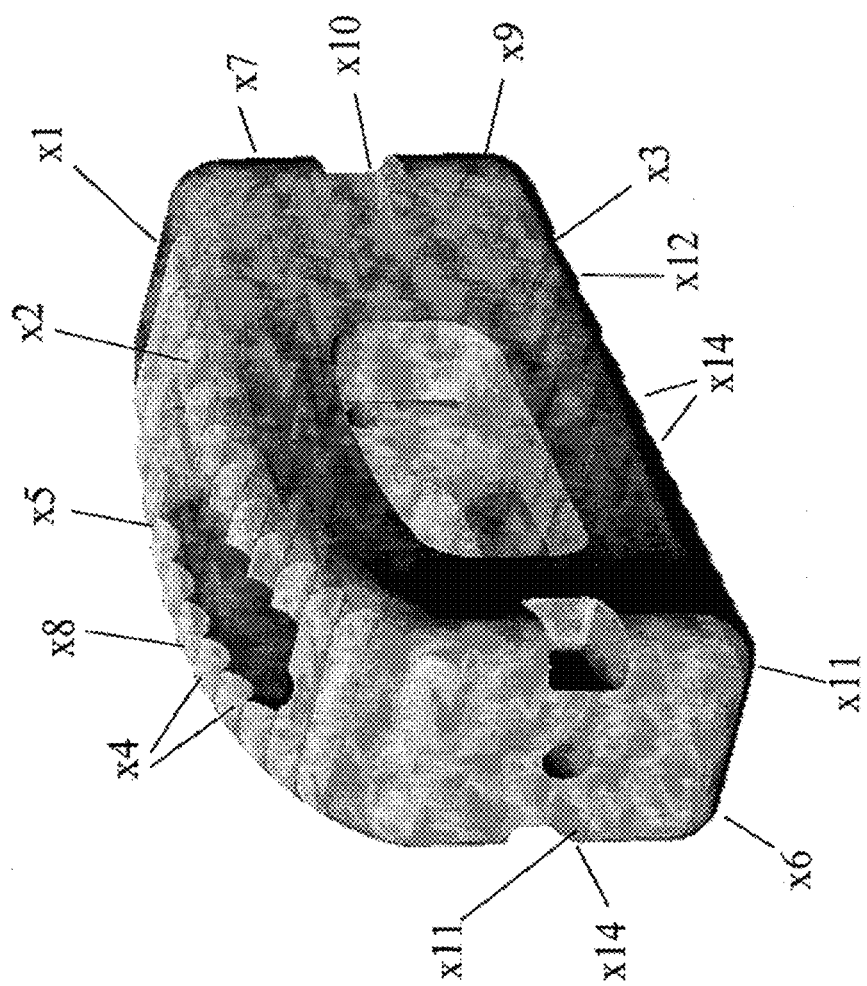
FIG. 22A provides an isometric view of one embodiment of a TLIF implant x1.
Figure 22B:
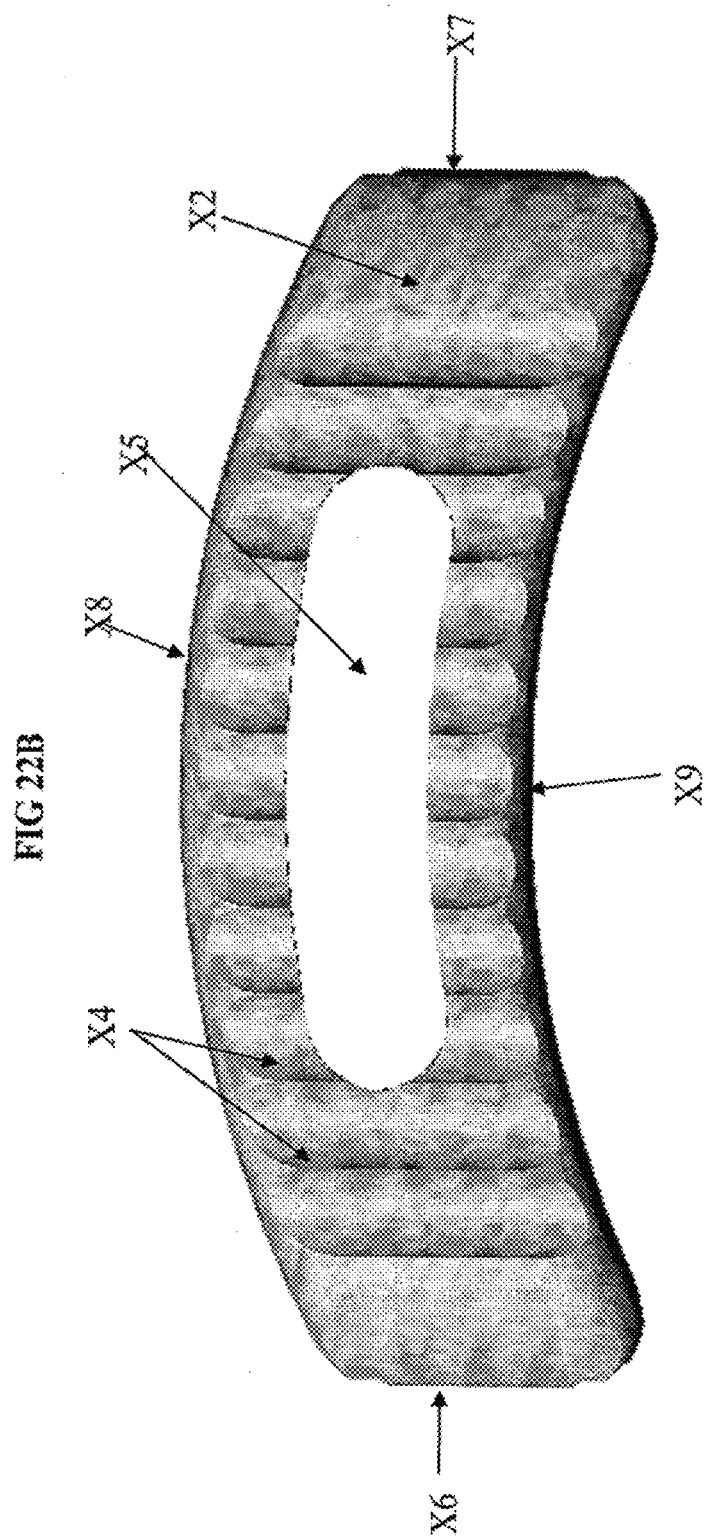
FIG. 22B provides a top and bottom planar view of implant of x1.

The PLIF implant 240 of the present invention may be in a variety of different sizes to accommodate differences in the patient's anatomy or the location in the spine. As FIGS. 20 through 22 illustrate, implant 240 comprises an anterior side 290 and a posterior side 300 being parallel to and opposing the anterior side 290; a medial 280 side and a lateral 270 side with one side being outwardly curved and the other being inwardly curved; and a top surface 250 and a bottom surface 260, each of the top 250 and bottom surfaces 260 including plural projections 255 for enhancing interaction with a synthetic or natural vertebral body. The projections 255 are similar in geometry to the protrusions in the cervical and ALIF implants of the present invention.

The implant also comprises a major recess 245 formed in the body creating a longitudinal through-aperture in communication with the top 250 and bottom 260 surfaces, at least one minor recess 275 formed in the body creating a latitudinal through-aperture in communication with the medial 280 and lateral 270 sides, both through apertures in communication with each other. The convergence of these through-apertures forms a cavity inside the implant in which graft material may be placed. This cavity formed by the through-apertures promotes bone growth and fusion between the adjoining vertebral bodies. Opening 245 may be packed with graft material to promote bone growth and fusion. Graft materials suitable for this purpose includes any of the materials disclosed herein. Blood and other biological fluids can be provided to the graft material through the minor recess 275.

The implant also comprises a handling feature comprising a pair of anterior recesses 273 formed at points where the anterior 290 side communicates with the medial 280 and lateral 270 sides. The anterior recesses 273 are used for receiving a manipulator. There are also a pair of posterior recess 283 formed at points where the posterior 300 side communicates with the medial 280 and lateral sides. The handling feature also includes a front opening 295 formed in the anterior 290 side. The handling feature facilitates the handling and insertion of the spinal implant into an intervertebral space.

FIGS. 20 and 22 illustrate implant 240 having a lordotic angle. The lordotic angle can range from −20 degrees to +20 degrees. In other embodiments, anterior side 300 and posterior side 290 are of the same height and have no lordotic angle.

In FIGS. 20 through 22, the anterior recesses 273 and the posterior 283 recesses may mate with an instrument, such as forceps, to add in the insertion or removal of the implant. The front 295 and rear openings 305 also allow implant 280 to be gripped and mated with an insertion tool. In certain embodiments, the medial 270 and lateral 280 sides may further comprise at least one minor recess 275 (or 285) to allow fluid to enter the interior of the implant after insertion.

Implant 240 may further include an opening 295 in posterior side 300, that is preferably internally threaded to accommodate an insertion tool, but that does not completely extend through the thickness of the posterior wall. This facet of the design is a safety feature implemented to prevent leakage of graft materials and the like, that may be placed in the hollow interior of the implant, into the spinal canal.

Implant 240 may be used alone or in conjunction with a complimentary implant. The two implants can be placed alongside one another as in a mirror image with the lateral 270 sides facing one another. This configuration allows bone graft material to be placed between two implants 240 and provides for maximum contact between natural bone and the implants.

V. TLIF

The bioactive material of the present invention may also be formed into an implant (FIGS. 22A-22D) suitable for TLIF procedures. TLIF implant devices are generally suitable for implantation in the lumbar regions of the spine.

In another embodiment of the present invention, the TLIF implant x1 of the present invention may be in a variety of different sizes to accommodate differences in patient's anatomy or the location of the spine that the implant x1 will be inserted. The TLIF implant x1 may be a variety of different sizes to accommodate differences in the patient's anatomy or the location in the spine. As FIGS. 20 through 22 illustrate, implant x1 comprises an anterior side x6 and a posterior side x7 being parallel to and opposing the anterior side x6 and a medial x8 side and a lateral x9 side with at least one side being outwardly curved. The implant also comprises a top surface x2 and a bottom surface x3, each of the top x2 and bottom surfaces x3 including plural projections x4 for enhancing interaction with a synthetic or natural vertebral body. Wave-like projections x4 are similar to the cervical, ALIF, and PLIF implants of the present invention.

Top surface and bottom surface x2 and x3 further define at least one major recess x5 to promote bone growth and fusion between the adjoining vertebral bodies. The major recess x5 creates a longitudinal through-aperture in communication with the top x2 and bottom x3 surfaces. The major recess x5 may be packed with graft material to further promote bone growth and fusion. Graft materials suitable for this purpose includes any of the materials disclosed herein.

As FIGS. 22A through 22D illustrate, the anterior x6 and posterior x7 sides are generally flat and parallel. In certain preferred embodiments, the medial x8 side is outwardly curved and the lateral x9 side is inwardly curved.

The implant also comprises a handling feature comprising a pair of anterior recesses x11 formed at points where the anterior x6 side communicates with the medial x8 and lateral x9 sides and a pair of posterior recess x10 formed at points where the posterior x7 side communicates with the medial x8 and lateral x9 sides. The pairs of recesses (x10 and x11) may be used for communication with a manipulator or instrument, such as, forceps. The handling feature also includes a front recess x14 formed in the anterior x6 side and a rear recess formed in the postelior x7 side both communicating with a through-aperture. This through-aperture is also in communication with the cavity formed in the spinal implant by the longitudinal and latitudinal through-apertures. The handling feature facilitates the handling and insertion of the spinal implant into an intervertebral space.

In certain embodiments, medial x8 and lateral x9 sides may further comprise at least one opening x12 and x13 to allow fluid to enter the interior of the implant after insertion to provide graft material placed in the center of the implant with blood or other biological fluids. FIGS. 22C and 22D show an embodiment of the implant x1 with two side openings x12 and x13 per wall. However, it should be understood that the implant x1 may not have side openings, or may have multiple pinhole openings along the length.

Implant x1 may further include an opening x14 in both of the anterior x6 and posterior x7 sides that may be internally threaded to accommodate an insertion tool. The front recess x14 may have an internal taper to mate with a tapered insertion instrument.

As shown in FIG. 22D, the top and bottom surfaces x2 and x3 may be outwardly curved. Further, implant x1 may be wedge shaped such that there is a lordotic angle. The lordotic angle may be same as those described earlier in other embodiments of the invention. In some embodiments the height of the wall of the anterior side x8 is greater than the height of the wall of the posterior side x9. Alternatively, the height of these walls may be equal.

The TLIF implant of the present invention is designed to engage the cortical rim of the vertebrae, the strongest portion of the vertebrae, and, as such, increases biomechanical stability. Additionally, the placement of this type of implant is generally less invasive and less destructive than other procedures, and may be cost effective since only one implant is used.

VI. Surgical Instrumentation

The present invention also provides surgical instrumentation to aid in the insertion, placement, or removal of the implants of the present invention.

Figure 23:
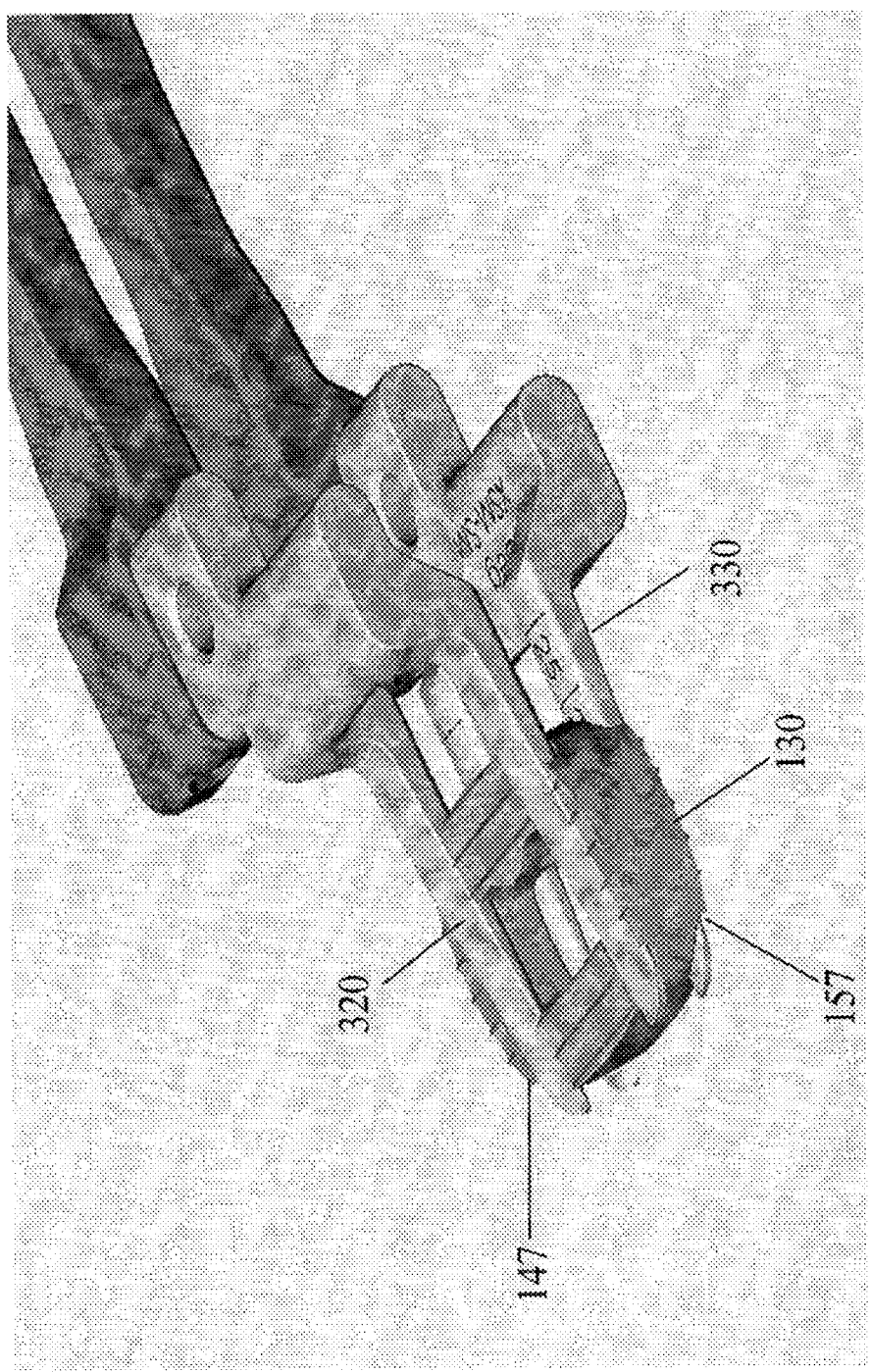
FIG. 23 provides an isometric view of one embodiment of the parallel distraction instrument 310 engaging the ALIF implant 130.
Figure 24:
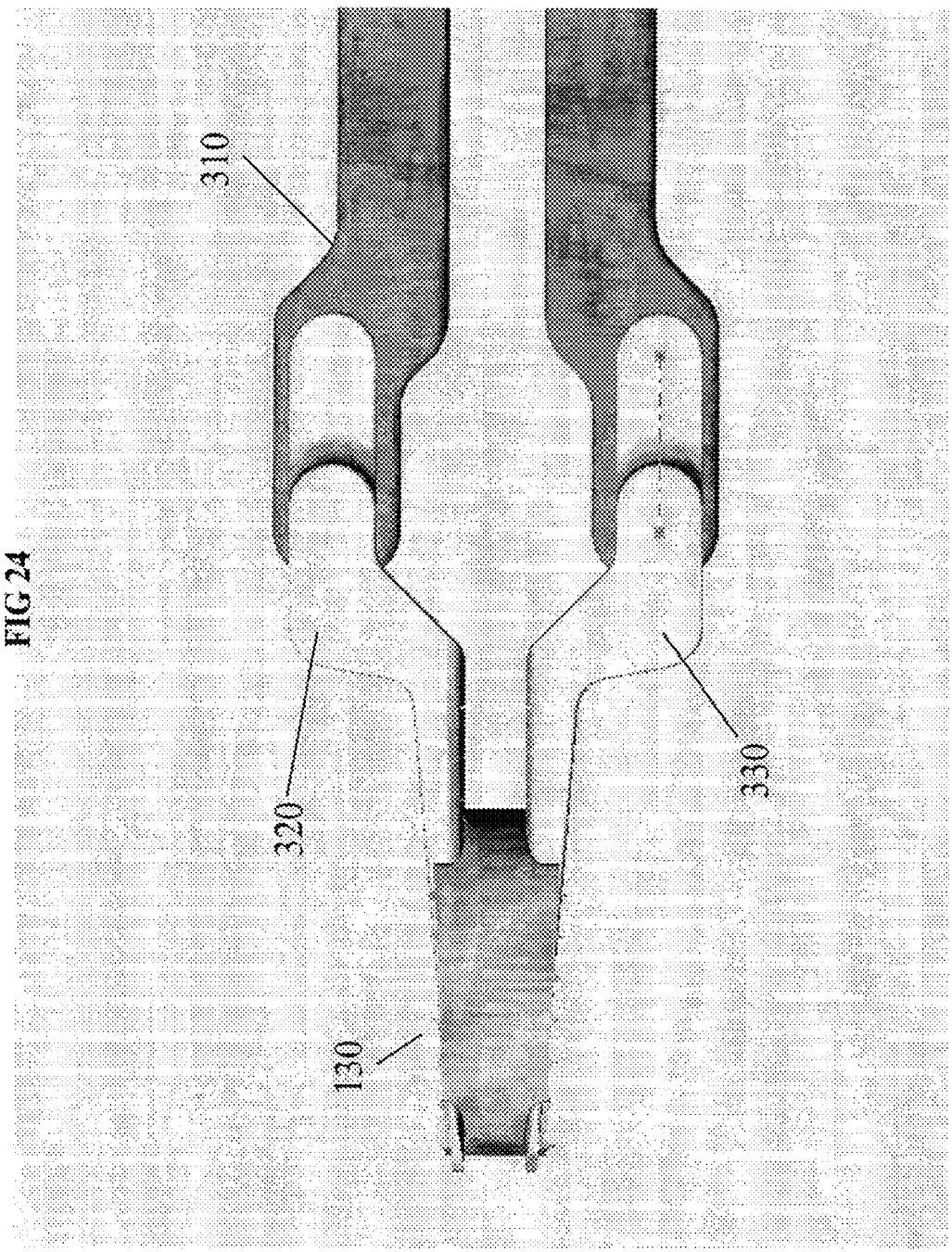
FIG. 24 provides a side view of the parallel distraction instrument 310 engaging the ALIF implant 130.
Figure 25:
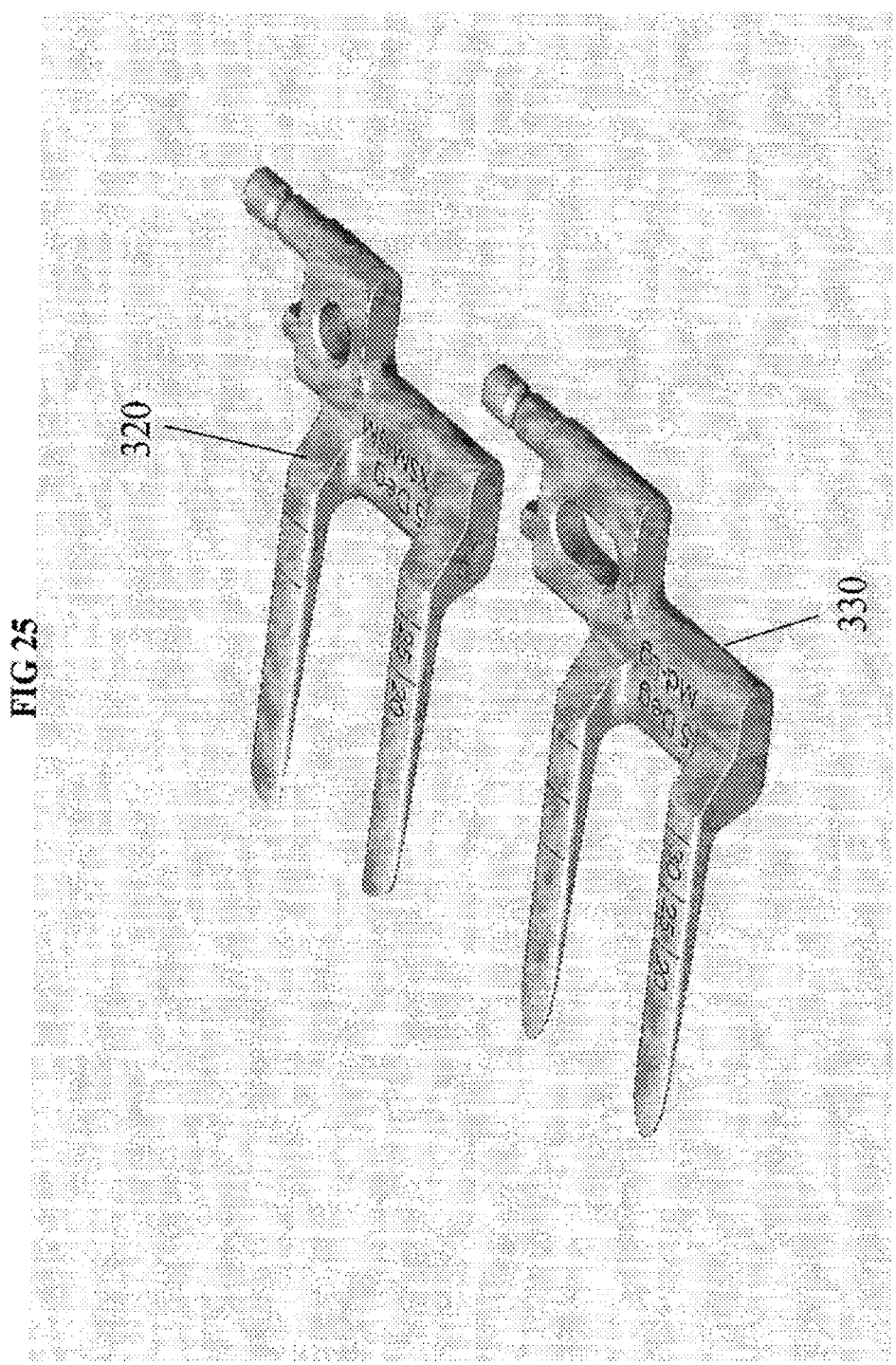
FIG. 25 provides an exploded view of the pair of upper 320 and lower forks 330 of the parallel distraction instrument 310.

FIGS. 23 through 27 illustrate various aspects of the parallel distraction instrument 310 of the present invention. Parallel distraction instrument 310 is suitable for the insertion of the ALIF implant of the present invention. The instrument 310 includes a pair of upper 320 and lower 330 forks that mate with the guide rails of the ALIF implant. For example, FIGS. 23 and 24 show instrument 310 engaging implant 130 via upper fork 320 engaging guide rails 147 on the top surface 140 of implant 130 and lower fork 330 engaging guide rails 157 on the bottom surface 150 of implant 130. Once instrument 310 holds the implant securely in place, the surgeon can insert the implant into the intervertebral space. Upon insertion of the instrument 310 with the implant, the handle 340 (see FIG. 27) of instrument 310 is depressed to actuate the two pairs of forks 320 and 330 in a parallel manner. In an alternate embodiment, a further insertion tool may slide between instrument 310 to place the implant in the intervertebral space. Instrument 310 further includes a scissor hinge and ratchet catch to allow for faster actuation than traditional screw style stops of the prior art and a faster release. Once instrument 310 is actuated, a device of the type shown in FIGS. 28-32 can pass through forks 320 and 330 and screw into opening 185 of the implant.

FIGS. 28 through 31 illustrate various features of an implant insertion and impactor tool 350. The tool 350 may be suitable for the insertion or removal of the cervical, ALIF, and PLIF implants of the present invention. Accordingly, the dimensions of tool 350 may vary depending upon the implant being inserted. Tool 350 includes a tip 360 that is comprised of a shock absorbing material that can withstand impact, such as a RADEL® tip and a sturdy body comprised of a material such as metal and a gripping handle 355. Tip 360 can be modular so that it is removable from the body of tool 350. Tip 360 has a projection 363 that mates with the anti-rotation convexity of the implant. The tip 360 further includes at least one opening 365, preferably a central opening that allows a "guide wire" with a threaded tip 370 to advance. In certain embodiments, threaded tip 370 advances through opening 365 upon rotation of the advancer 380 adjacent to the tool handle 353 (see FIGS. 28 and 30). Both the threaded tip 370 and projection 363 on the tool tip 360 mate with the threaded opening and anti-rotation convexity of the implant to allow for insertion or removal of the implant.

Figure 32:
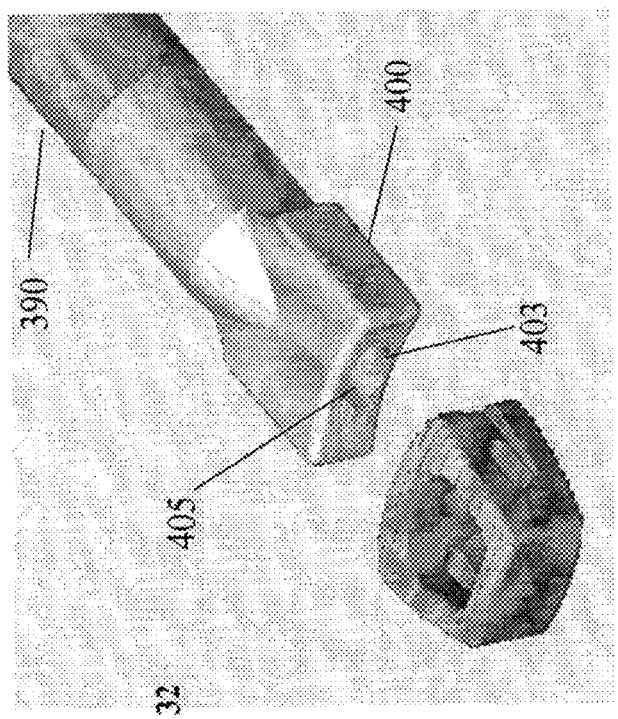
FIG. 32 provides an isometric view of the implant insertion tool 390 prior to engaging cervical implant 10.
Figure 33:
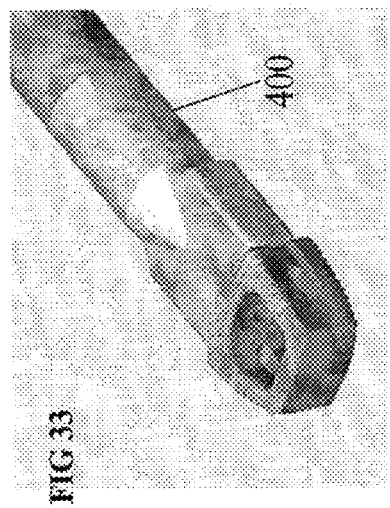
FIG. 33 provides an isometric view of the implant insertion tool 390 engaging cervical implant.
Figure 34:
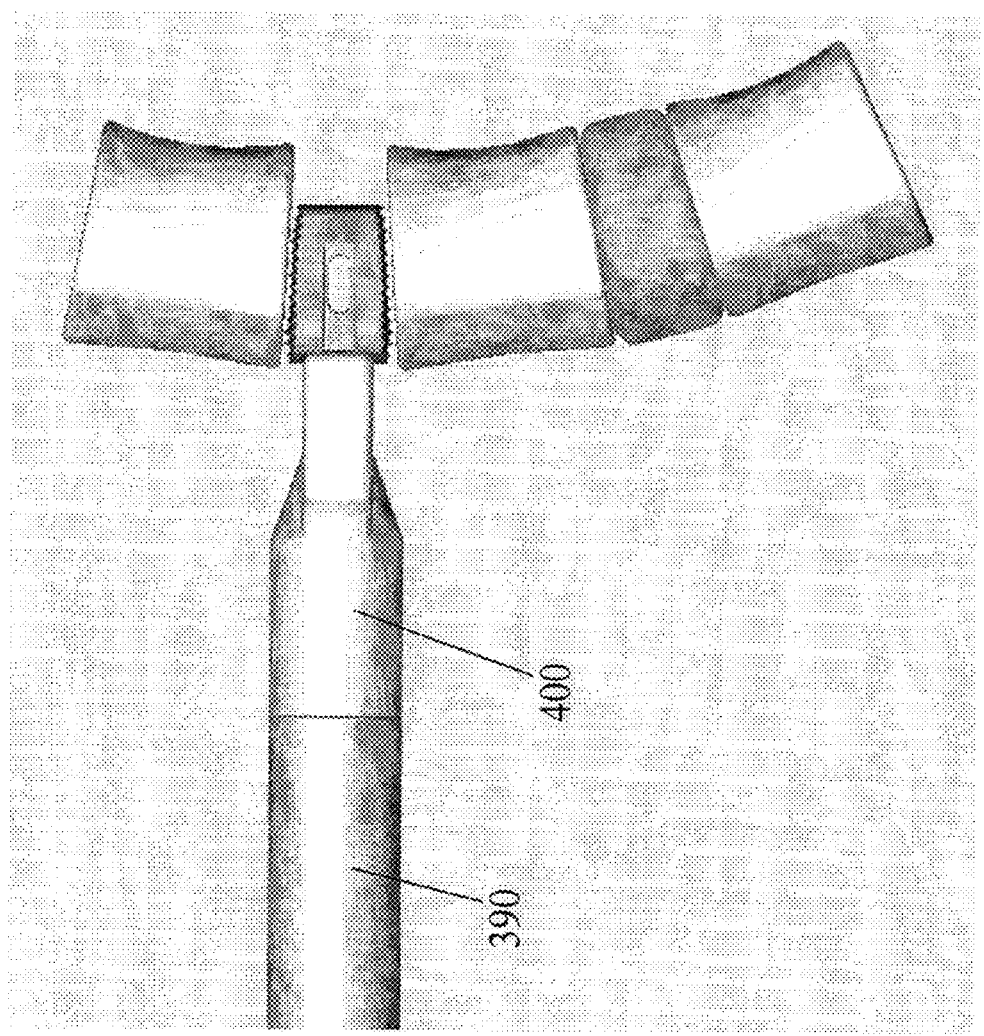
FIG. 34 provides a side view of the implant insertion tool 390 inserting cervical implant 10 between two vertebral bodies.

FIGS. 32 through 34 illustrate various features of another embodiment of an insertion and impaction tool 390 of the present invention. Tool 390 mates (lushly with the implant face and allows for impaction at the opposite end of the tip. Similar to tool 350, tool 390 has a tip 400 that is comprised of a shock absorbing material such as RADEL® and a sturdy body 393 which is comprised of a metal and a gripping handle 395. Tip 400 has a projection 403 that mates with the anti-rotation convexity of the implant. Tip 400 may further include at least one opening 405, preferably a central opening, that allows a "guide wire" with a threaded tip to advance.

Figure 30:
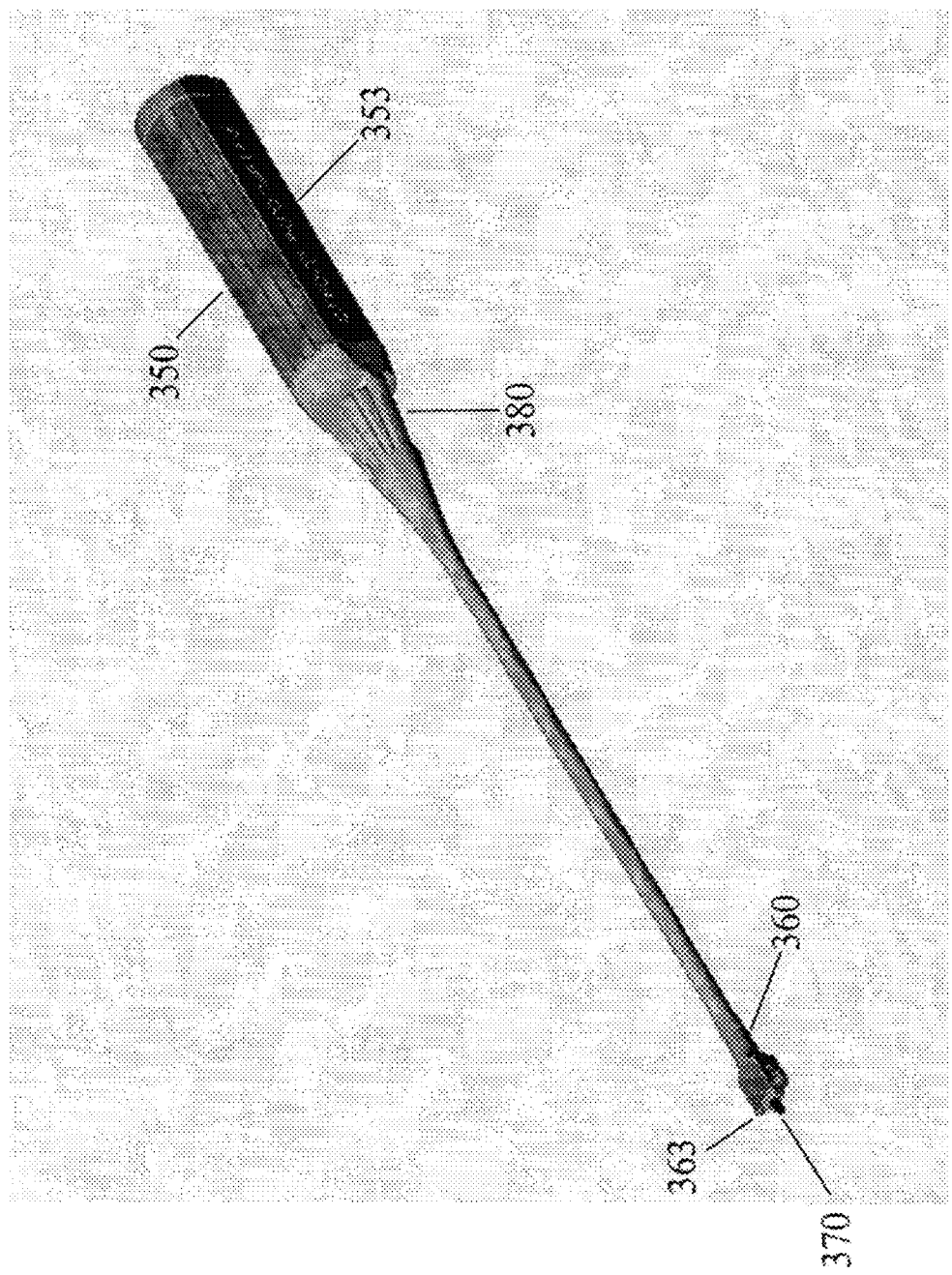
FIG. 30 provides an isometric view of another embodiment of the implant insertion tool 350 featuring a threaded tip.
Figure 31:
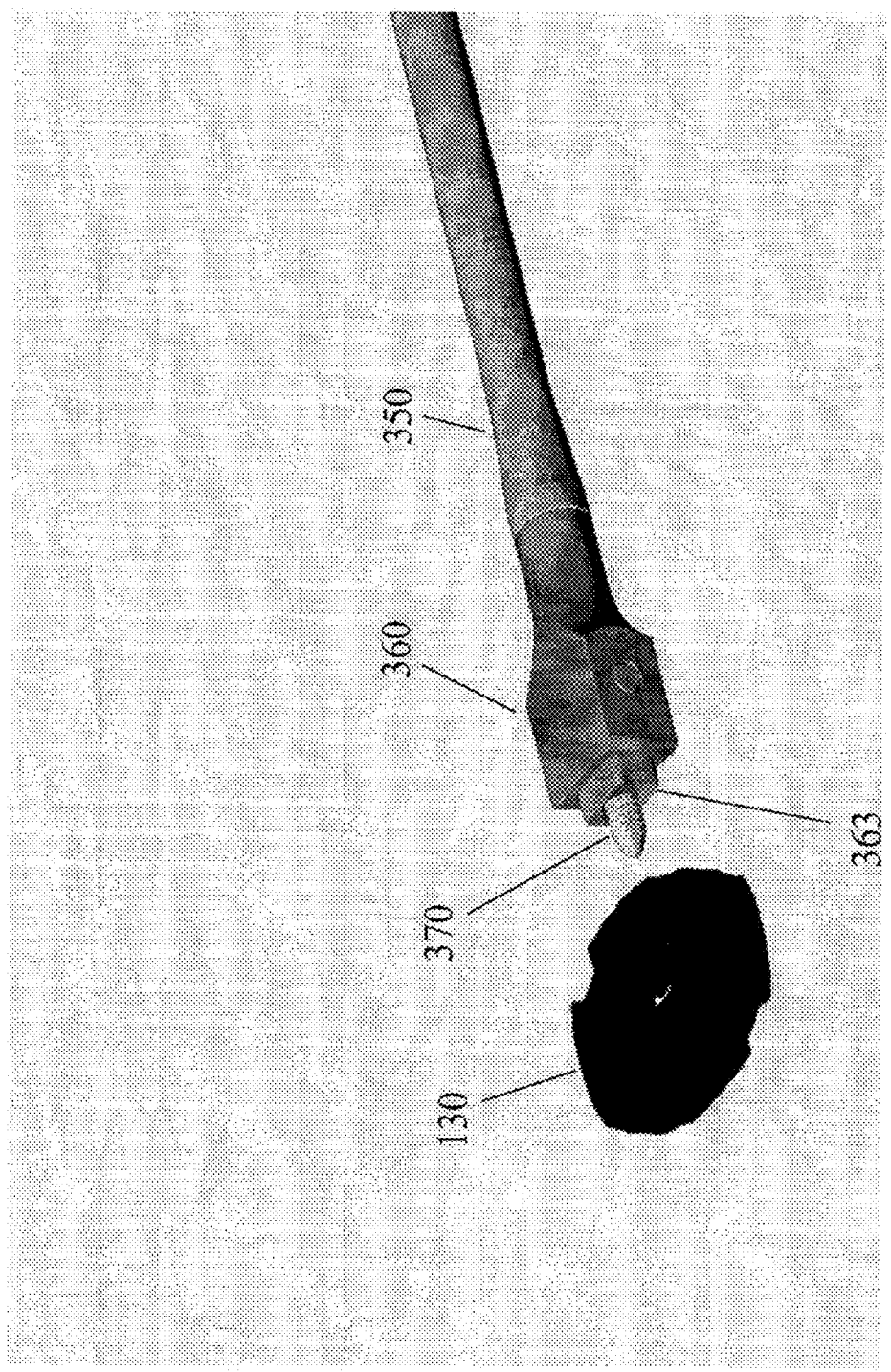
FIG. 31 provides a detailed, isometric view of the implant insertion tool 350 about to engage the ALIF implant 130.
Figure 35:
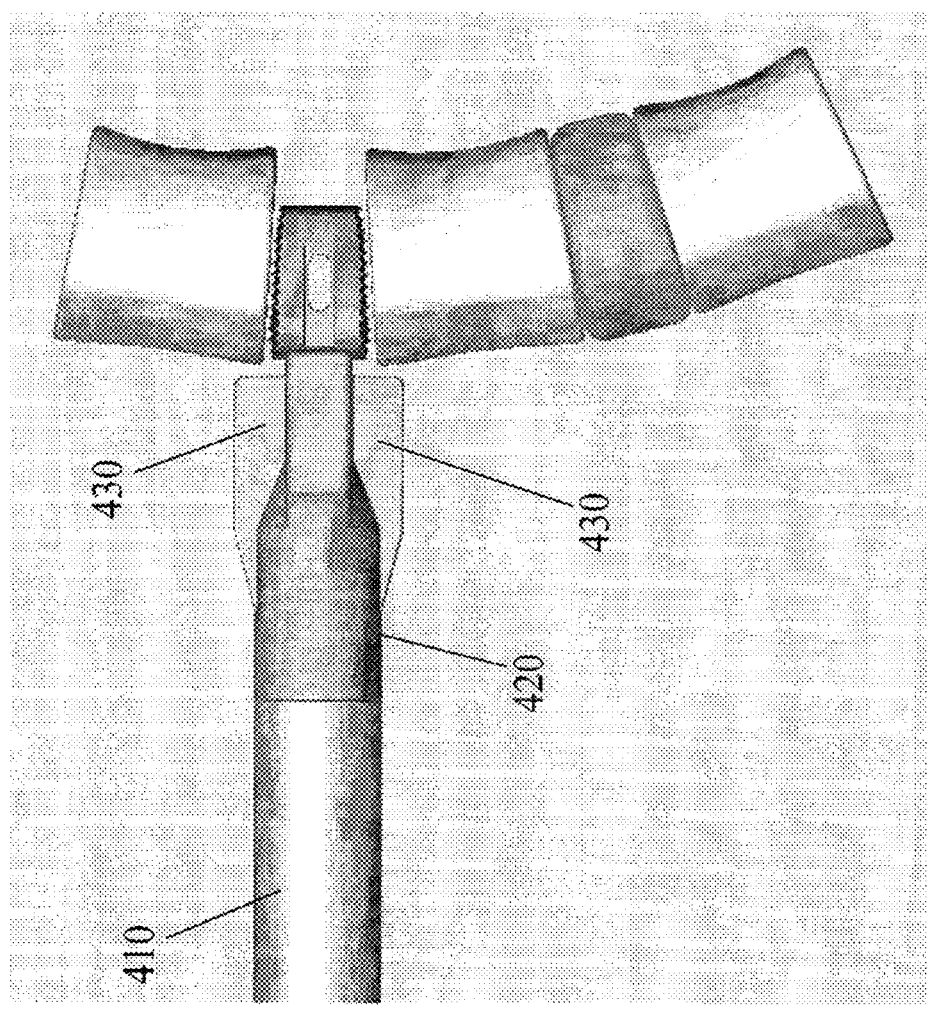
FIG. 35 provides a side view of another embodiment of the implant insertion tool 110 inserting the cervical implant 10 between two vertebral bodies.
Figure 38:
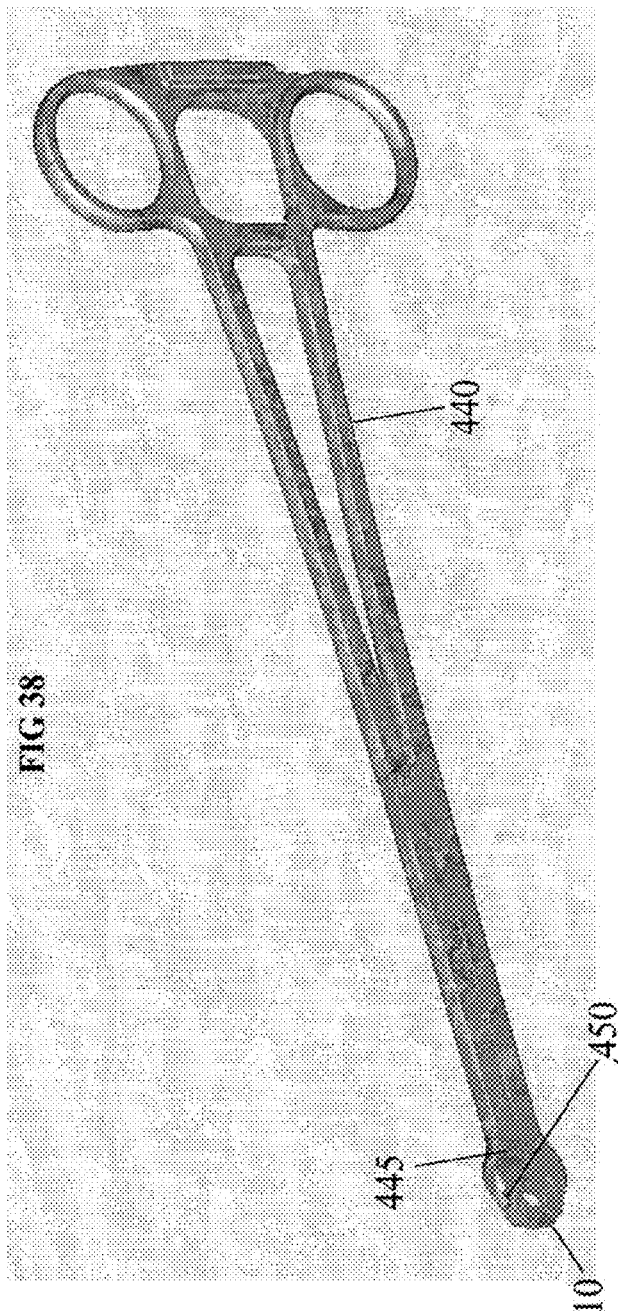
FIG. 38 provides an isometric view of the forceps 440 engaging the cervical implant 10.
Figure 39:
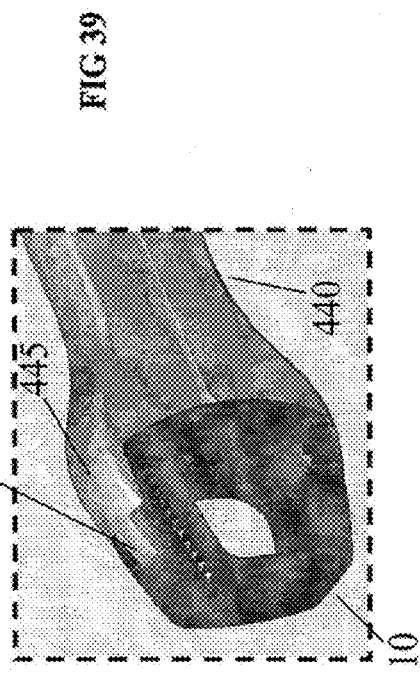
FIG. 39 provides a detailed, isometric view of the forceps 440 engaging the cervical implant 10.
Figure 45:
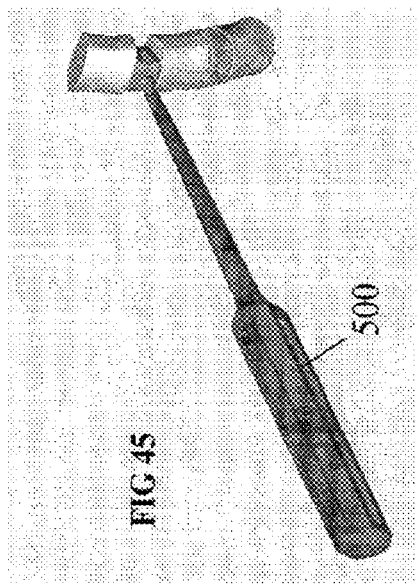
FIG. 45 provides an isometric view of the insertion tool 500 and the cervical implant 10 being inserted between two vertebral bodies.
Figure 46:
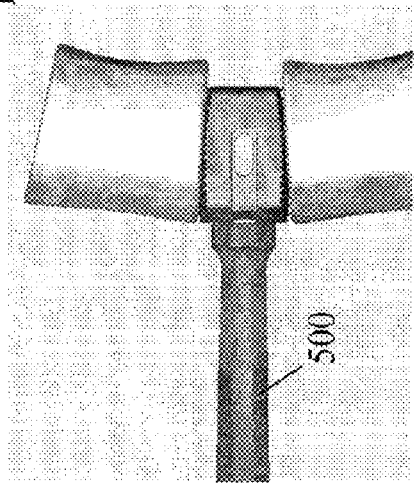
FIG. 46 provides a side view of the insertion tool 500 and the cervical implant 10 being inserted between two vertebral bodies.

FIG. 35 illustrates an alternate embodiment of the implant insertion and impaction tool 410 of FIG. 30 that includes a limiting impaction tip 420. Limiting impaction tip 420 has stops 430 that allow the surgeon to gauge how far tip 420 and the implant is displaced in the anterior to posterior direction with respect to the vertebral bodies. The height of stops 430 in a vertical direction may be any height that prevents tool 410 from going in-between adjacent vertebral bodies. The limiting impaction tip 420 may be modular or removable from tool 410. Tip 420 may be made with a set stop length that ranges between about 2 mm to about 4 mm to allow the surgeon to gauge how far into the intervertebral space the implant is being inserted.

FIGS. 36 through 39 illustrate various aspects of forceps 440 of the present invention that may be used for insertion of implants, such as the cervical implants 10 of the present invention. Forceps 440 may be used to as an alternative to the insertion and impaction tools 350 and 390 of the present invention. Forceps 440 are generally scissor-like in shape and have two openings at the handle to accommodate the fingers of the surgeon. Forceps 440 may include nubs 450 on the inside of each tip 445 for mating with the openings on the medial and lateral sides 43 and 45 and 53 and 55 of the implant 10. Tip 445 may further include shock absorbing pads 460 that are comprised of a material such as RADEL® to cushion the implant if the forceps 440 are also used for impaction.

FIGS. 40 and 41 provide an exploded and isometric view of an insertion and impaction tool 470 that is suitable for use with any of the implants of the present invention. Tool 470 may be provided with a modular tip 480 that may be made of a shock absorbing material, such as but not limited to RADEL®, that is secured to tool 470 with a fastener 490 or other means. This allows tip 480 to be replaced after wear due to repeated use. Alternatively, the insertion and impaction tool may be integral with the tool body and handle such as tool 500 in FIG. 42. Preferably the tip of tool 470 or 500 is rounded and smooth-edged. In use, the impactor and insertion tool 500 is placed flush against the implant 10 (see FIG. 43) and then tapped via impaction hammer 510 to adjust the position of the implant (see FIGS. 44 through 47c). The impaction and insertion tool allows for the surgeon to focus on various contact spots such as the medial aspect, the lateral aspect or the center of the implant for medial, lateral, and the anterior to posterior positioning of the implant (see FIGS. 45 through 47c).

Figure 47C:
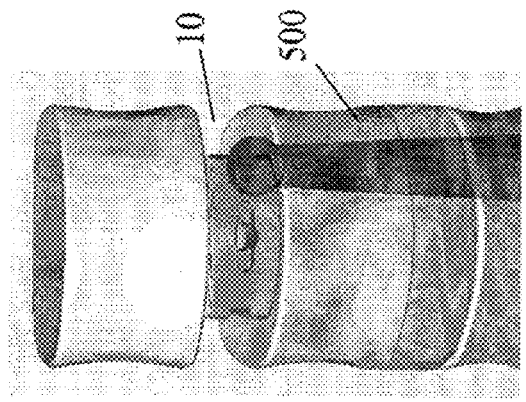
FIGS. 47a through 47c provide a front view of the insertion tool 500 being used to adjust the position of the implant 10 between the two vertebral bodies.
Figure 47B:
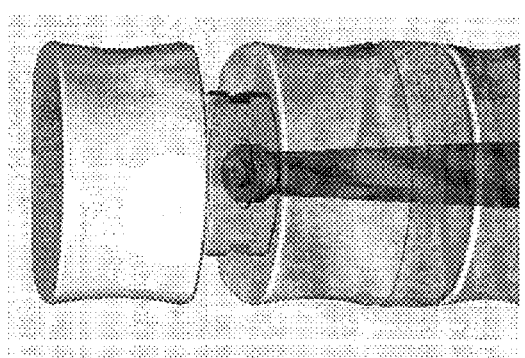
Figure 47A:
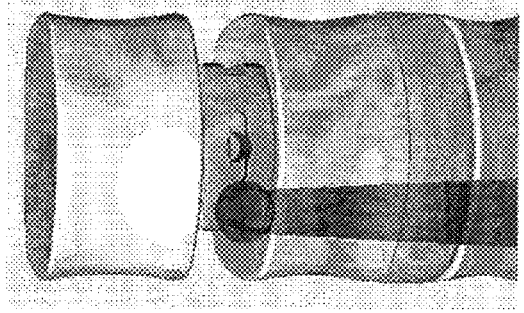
Figure 47D:
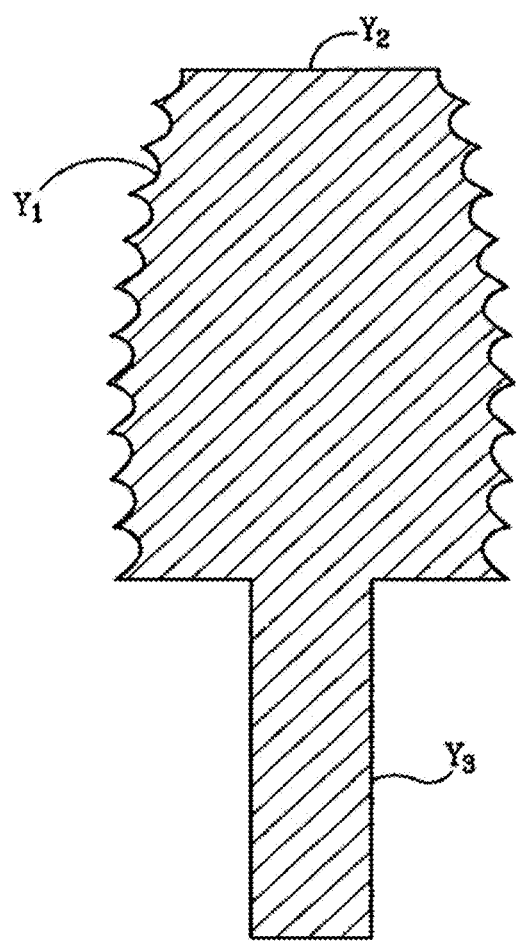
FIG. 47D provides a side view illustrating a rasp instrument y1 of the present invention to be used to shape the endplate prior to implant insertion.

FIG. 47D shows a side view of a rasp y1 of the present invention used in the preparation of the endplate. The rasp y1 is in the shape of the implant being inserted so as to contour the endplates to accommodate the eventual implant being inserted and provide for good contact between the endplate bone and the implant. Although FIG. 47D shows a rasp y1 with a headpiece y2 in the shape of a cervical type implant, it should be understood that the headpiece y2 of the rasp y1 could be in any implant shape including the ALIF, PLIF and TLIF types disclosed herein. Rasp y1 also includes a handle y3, which may be integral to or a modular with the headpiece y2, for gripping and manipulating the rasp y1. FIGS. 48 and 49 provide an isometric and detailed isometric view of trial tools 520 with plugs 530 of the present invention. Tool 520 is used after preparation of the intervertebral space and prior to insertion of the implant to determine the size of the implant to insert. Plugs 530 can be modular (i.e., fasten or snap onto the end of tool 520) or be integrated into tool 520. Plugs 530 are generally the same size and shape of the implant. In FIG. 49, plug 530 may be similar in size and shape to the cervical implant 10 of the present invention.

Figure 52:
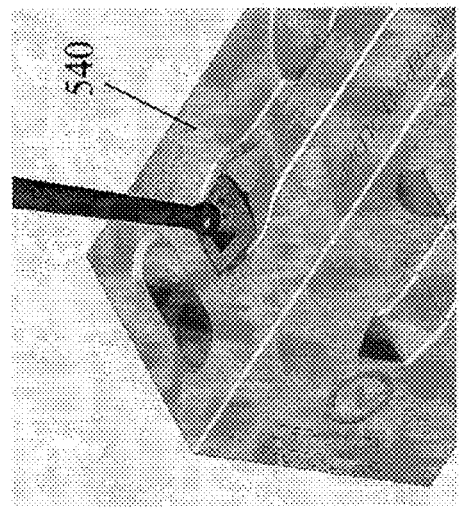
FIG. 52 provides an isometric view of the graft impaction block 540 and the inseltion of graft material into the cervical implant 10.
Figure 50:
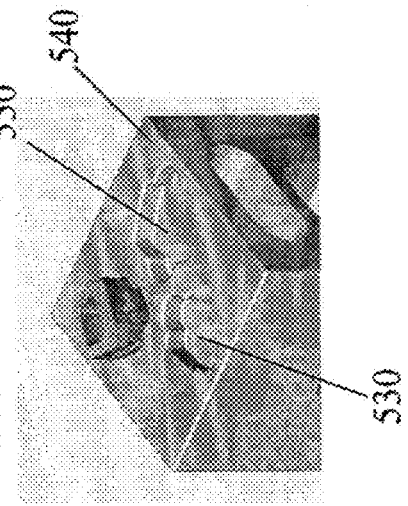
FIG. 50 provides an isometric view of one embodiment of the graft impaction block 540 of the present invention.
Figure 51:
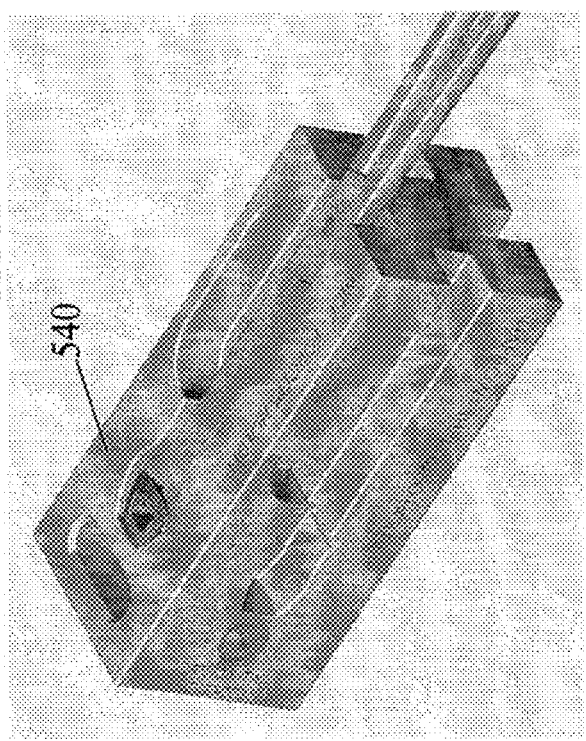
FIG. 51 provides an isometric view of the graft impaction block 540 and the forceps tool 440 engaging the cervical implant 10.

FIGS. 50 through 52 illustrate various aspects of the view of graft impaction block and implant/tool holder 540 of the present invention. Graft impact block 540 comprises a plurality of recesses 550 of various sizes to accommodate various sizes of implants of the present invention. Block 540 allows the graft material to be packed into the hollow interior of the implant.

EXAMPLES

Example 1

Bioactive Spinal Implant Material

An exemplary implant material for the manufacture of spinal implants in accordance with the invention was formulated to exhibit biocompatibility and bioactivity for bone bonding, radiopacity similar to bone in order to be able to assess fusion, mechanical strength to support physiologic loads, and bone-like stiffness to allow for good load sharing among the elements of the spine.

One implant material includes a polymeric blended resin, comprising 20% to about 50% by weight of the implant material total composition. The resin blend can be further comprised of from about 30% to about 90% by weight of resin OUOMA, about 10% to about 0.25% by weight of butyrated hydroxy toluene (BHT).

The remainder of the implant material is comprised of a plurality of fillers. The fillers can be further comprised up to about 40% by weight of filler surface treated E-Glass® fibers to impart fracture toughness and mechanical strength. The filler also can have an average length of about 3000 μm or less and an average diameter range of about 5 μm to 50 μm; about 5% to about 50% by weight of filler surface treated, silanated combeite filler having bioactive characteristics which promote bone bonding; up to about 50% by weight of filler of a surface treated borosilicate glass filler having an average diameter of −10 μm (e.g., 90% of the particles have a diameter of less than 10 μm, measured by laser analysis); and up to about 30% by weight of filler of a surface treated silica for imparting mechanical strength and to act as a rheology modifier. In this particular example, the filler is comprised of about 20% by weight surface treated E-Glass® fibers, about 20% by weight of filler surface treated, silanated combeite filler, about 23% by weight of filler of a surface treated borosilicate glass filler, and about 5% by weight of filler is surface treated silica. Once all components are combined, the formulated material is hardened via conventional heating processes, which initiates the polymerization reaction.

Example 2

Radiopacity of a Bioactive Spinal Implant

Quantitative Evaluation: Three tensile bar samples of polymerized bioactive material of the type described herein, approximately 4 mm in thickness, were arranged onto x-ray film, and a 16-step Aluminum step was placed on top. The 10-mm thick Aluminum step was placed so that it was partly shielding a polymerized sample and partly over x-ray film only (these materials were situated in a Faxitron x-ray cabinet). The use of an Aluminum background allowed for more reproducible comparison between x-rays than the use of exposed film alone. The other two samples were placed at the ends of the wedge in order to balance it.

The lowest stage in the Faxitron cabinet was used and its focus-film distance was 50 mm. The 4-mm thick samples were exposed using appropriate exposure time and voltage (180 sec., 80 kVp). A background optical density ranging from 0.8 to 1.2 defined an appropriate exposure.

After the film had been exposed to x-rays, it was removed from the Faxitron and developed.

Using the densitometer, Background (B), Sample(S) and Aluminum (A) density values were recorded.

The same process was used to determine the radiopacity values of gamma irradiated material as prepared in accordance with Example 1 above.

Calculations

The percent relative linear attenuation coefficient, α, was calculated as follows:

$$\alpha = \frac{(B-S)}{(B-A)} \times 100$$

where:

B=background optical density of 10 mm of Al, in the range of 0.8 to 1.2.

A=optical density under the 14 mm thickness of Al (4 mm Al sample added to 10 mm Al background), and S=optical density of the image of the 4 mm thick sample.

Results

Quantitatively, the material, before gamma irradiation, had an average radiopacity value of 45.55.

TABLE 1

Optical density values for three lots of material prior to gamma irradiation.

| Lot Number | Sample | Background, B | Sample, S | Aluminum, A | Linear attenuation coefficient, a |
|---|---|---|---|---|---|
| 022601-067 | 1 | 0.89 | 0.76 | 0.58 | 41.94 |
|  | 2 | 0.86 | 0.73 | 0.57 | 44.83 |
|  | 3 | 0.92 | 0.78 | 0.61 | 45.16 |
| Mean |  | 0.89 | 0.76 | 0.59 | 43.98 |
| S.D. |  | 0.03 | 0.03 | 0.02 | 1.77 |
| 022601-074 | 1 | 0.92 | 0.78 | 0.61 | 45.16 |
|  | 2 | 0.83 | 0.71 | 0.55 | 42.86 |
|  | 3 | 0.93 | 0.78 | 0.60 | 45.45 |
| Mean |  | 0.89 | 0.76 | 0.59 | 44.49 |
| S.D. |  | 0.06 | 0.04 | 0.03 | 1.42 |
| 032601-082 | 1 | 0.92 | 0.78 | 0.60 | 43.75 |
|  | 2 | 0.91 | 0.77 | 0.66 | 56.00 |
|  | 3 | 0.85 | 0.72 | 0.56 | 44.83 |
| Mean |  | 0.89 | 0.76 | 0.61 | 48.19 |
| S.D. |  | 0.04 | 0.03 | 0.05 | 6.78 |
| 022601-067 | Mean | 0.89 | 0.76 | 0.59 | 43.98 |
| 022601-074 | Mean | 0.89 | 0.76 | 0.59 | 44.49 |
| 032601-082 | Mean | 0.89 | 0.76 | 0.61 | 48.19 |
| Mean |  | 0.89 | 0.76 | 0.60 | 45.55 |
| S.D. |  | 0.00 | 0.00 | 0.01 | 2.30 |

Quantitatively, the material, after gamma irradiation, had an average radiopacity value of 42.94.

TABLE 2

Optical density values for three lots of material after gamma irradiation

| Lot Number | Sample | Background, B | Sample, S | Aluminum, A | Linear attenuation coefficient, a |
|---|---|---|---|---|---|
| 022601-067 | 1 | 1.01 | 0.85 | 0.62 | 41.03 |
|  | 2 | 0.99 | 0.84 | 0.63 | 41.67 |
|  | 3 | 1.05 | 0.89 | 0.68 | 43.24 |
| Mean |  | 1.02 | 0.86 | 0.64 | 41.98 |
| S.D. |  | 0.03 | 0.03 | 0.03 | 1.14 |
| 022601-074 | 1 | 1.01 | 0.85 | 0.64 | 43.24 |
|  | 2 | 1.00 | 0.84 | 0.62 | 42.11 |
|  | 3 | 1.01 | 0.85 | 0.64 | 43.24 |
| Mean |  | 1.01 | 0.85 | 0.63 | 42.86 |
| S.D. |  | 0.01 | 0.01 | 0.01 | 0.66 |
| 032601-082 | 1 | 0.99 | 0.84 | 0.63 | 41.67 |
|  | 2 | 0.98 | 0.83 | 0.62 | 41.67 |
|  | 3 | 1.01 | 0.83 | 0.64 | 48.65 |
| Mean |  | 0.99 | 0.83 | 0.63 | 43.99 |
| S.D. |  | 0.02 | 0.01 | 0.01 | 4.03 |
| 022601-067 | Mean | 1.02 | 0.86 | 0.64 | 41.98 |
| 022601-074 | Mean | 1.01 | 0.85 | 0.63 | 42.86 |
| 032601-082 | Mean | 0.99 | 0.83 | 0.63 | 43.99 |
| Mean |  | 1.01 | 0.85 | 0.63 | 42.94 |
| S.D. |  | 0.02 | 0.02 | 0.01 | 1.01 |

Conclusions

A total of three lots of polymerized bioactive material consisting of three samples per lot of material was evaluated and compared directly to Aluminum for radiopacity determination. All testing was conducted in accordance with Orthovita's Technical Operating Procedure. Results summarized in the preceding tables indicate that the bioactive spinal material has an average radiopacity value of 45.55 before gamma irradiation and a radiopacity value of 42.94 after gamma irradiation. Statistical analysis of results demonstrates that there is not a significant amount of variance between lots and data records, p=0.445 for pre-gamma data and p=0.624 for post-gamma data. Statistical analysis also shows that there is not a significant amount of variance between pre and post gamma data. This indicates that gamma irradiation does not significantly affect the radiopacity of the material.

Radiopacity of polymerized material for medical use is clinically important due to the frequency of using x-rays in measuring the placement, function, form, and effectiveness of the material. Both pre and post gamma bioactive implants have a radiopacity value that will allow for good radiographic viewing that will aid in the placement and postoperative monitoring of spinal implants made from this material. Radiopacity values for the bioactive spinal implant material of the present invention compare favorably with human bone, which has a radiopacity range of between 24 to 52.

Figure 53A:
FIG. 53a provides a radiograph of an implant of the present invention after insertion between adjacent vertebrae in a sheep spine, and FIGS. 53b and 53c provide a radiograph and corresponding image, respectively, of a present invention implant (top) in comparison to a titanium implant (bottom) in a calf spine.
Figure 53C:
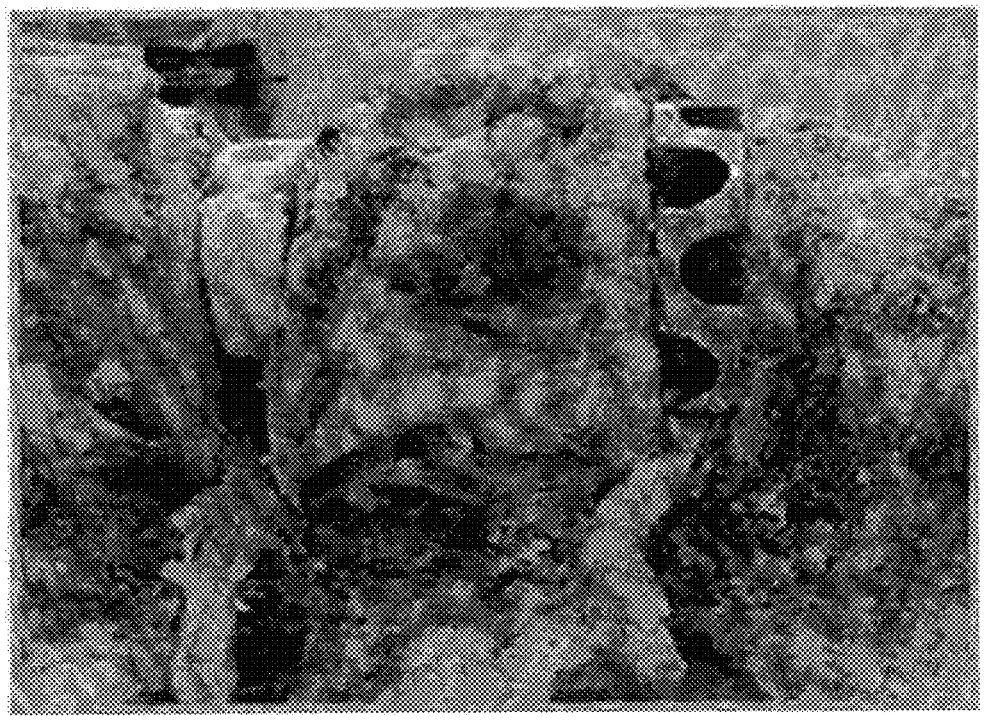
Figure 53B:
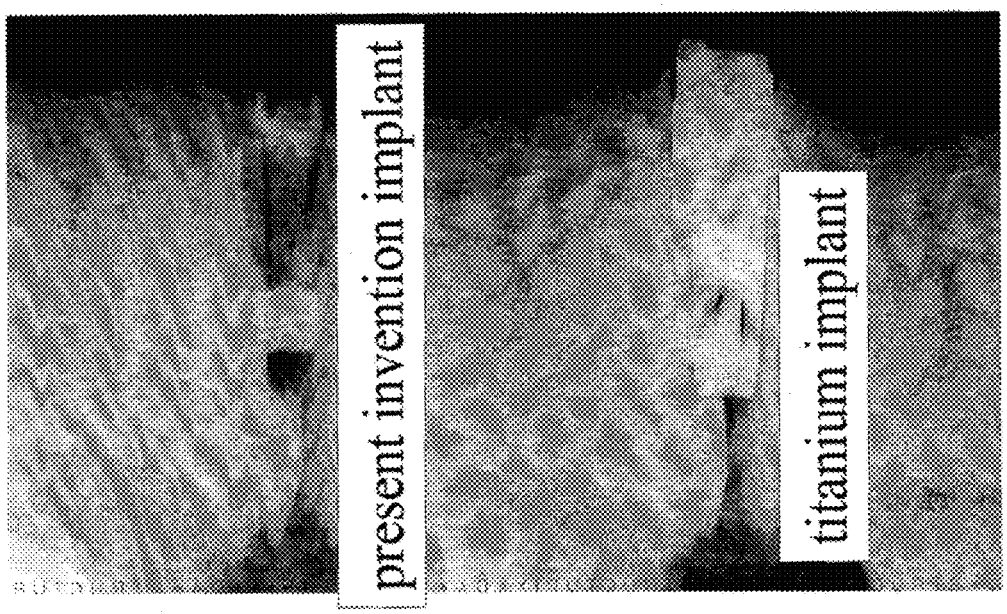

As observed in FIG. 53a, the radiopacity of the material of the present invention allows for visualization of the implant between adjacent vertebral bodies (in this case in a segment of a sheep spine), as well as visualization for the eventual assessment of fusion from a medial-lateral radiograph. This observation is also noted in FIGS. 53b and 53c, in comparison to a titanium implant.

Example 3

Mechanical Properties of a Bioactive Spinal Implant Material

Samples were prepared using the bioactive material described herein. Tests were performed using ASTM Guidelines on an Instron Model 8516 in order to obtain ranges of values of mechanical properties of the material as shown in the table below.

TABLE 3

Mechanical Properties of a Bioactive Spinal Implant Material

| TEST | RESULT | HUMAN CORTICAL BONE LITERATURE |
|---|---|---|
| Compressive Strength ASTM F 451-95 and ASTM D695-91 | 220-250 MPa | 167-215 MPa |
| Compressive Modulus ASTM F 451-95 and ASTM D695-91 | 7.0-9.0 GPa | 14.7-19.7 MPa |
| Compressive Yield Strength ASTM F 451-95 and ASTM D695-91 | 170-182 MPa | 121-182 MPa |
| Tensile Strength ASTM D638-98 | 65-100 MPa | 70-140 MPa |
| Tensile Elastic Modulus ASTM D638-98 | 14-17 GPa | 10.9-14.8 MPa |
| 3-Point Flexural Strength ASTM D790-90 | 100-120 MPa | 103-238 MPa |
| Shear by Punch Tool ASTM D732-93 | 60-80 MPa | 51.6 MPa |
| Compressive Fatigue Strength ($10^6$ cycles) | 170-190 MPa | >100 MPa |
| Tensile Fatigue Strength ($10^6$ cycles) | 35-55 MPa | 49 MPa |

Example 4

Bioactivity Testing of a Spinal Implant

Bioactivity testing was performed on disc shaped implants comprised of the material described herein. Bioactivity for this Example was defined as the ability of the implant to form a calcium phosphate layer on its surface.

Uncured samples of the material described in Example 1 were injected into 5 cc syringes. The material was heated at 100° C. for 1 hour for complete polymerization. The rods formed within the syringe were cut into thin disks (approximately 1 mm thick) using a Buehler diamond blade saw. Simulated body fluid (SBF) was prepared according to the Kokubo recipe (fluid which simulates blood plasma) and using a balance, 250 grams of simulated body fluid was weighed into 5 high density polyethylene (HDPE) bottles. One disk of material was placed in each of the five bottles. The containers of SBF containing the disks were placed at 37° C. for specified intervals. The time intervals were 6, 12, 19, 30, and 50 days. A sample size of 1 disk was prepared at each time period. At these time points, one disk of material was removed from its bottle. The sample was dried with compressed air prior to analysis. The SBF was not analyzed prior to immersion of samples and was discarded after the last sample was removed.

As a non-destructive test, Fourier Transform Infrared Spectroscopy (FTIR) was performed first on the samples. The samples were analyzed using the Nicolet Instruments *Magna* 560 FTIR. The stage used for this analysis was a single-bounce Attenuated Total Reflectance (ATR) with a diamond crystal and KRS-5 lenses. This stage permitted a surface analysis of the composites through the entire mid-infrared spectrum from 4000 to 400 cm$^{-1}$ samples were analyzed at a 4 cm$^{-1}$ resolution. The samples were placed in direct contact with the ATR crystal. Contact was maximized via an anvil on the opposite side of the sample. Spectra were collected on several areas of the composite samples. At each time point, spectra were analyzed for the presence of key calcium phosphate bands as compared to the Day 0 control.

After FTIR analysis, the same samples were then used for Scanning Electron Microscopy/Energy Dispersive Spectroscopy (SEM/EDS). Samples were coated with a thin layer of gold-palladium using a Hummer Sputter Coater. Samples were painted with a small amount of conductive silver paint, when necessary. The operation procedure of the SEM analysis followed the standard procedure for the operation of the JEOL JSM-840A and the EDS analysis. A few of the thin disks were cut exposing the cross-section of the composite. The cross-sections were embedded in epoxy resin revealing the cut surface. Upon complete curing of the epoxy, samples were polished on the Buehler EcoMet3. Final polishing consisted of a 1-micron diamond suspension.

The characterization of bioactivity of the polymerized composite surface by scanning electron microscopy consisted of the following parameters: appearance of calcium phosphate deposition (white in back-scattered electron imaging "BSEI" mode) and thickness of calcium phosphate layer. The characterization of bioactivity of the polymerized composite surface by energy dispersive spectroscopy consisted of the following parameters: calcium and phosphorous detection and reduction in sodium levels at a bioactive filler.

FTIR Results

Figure 54:
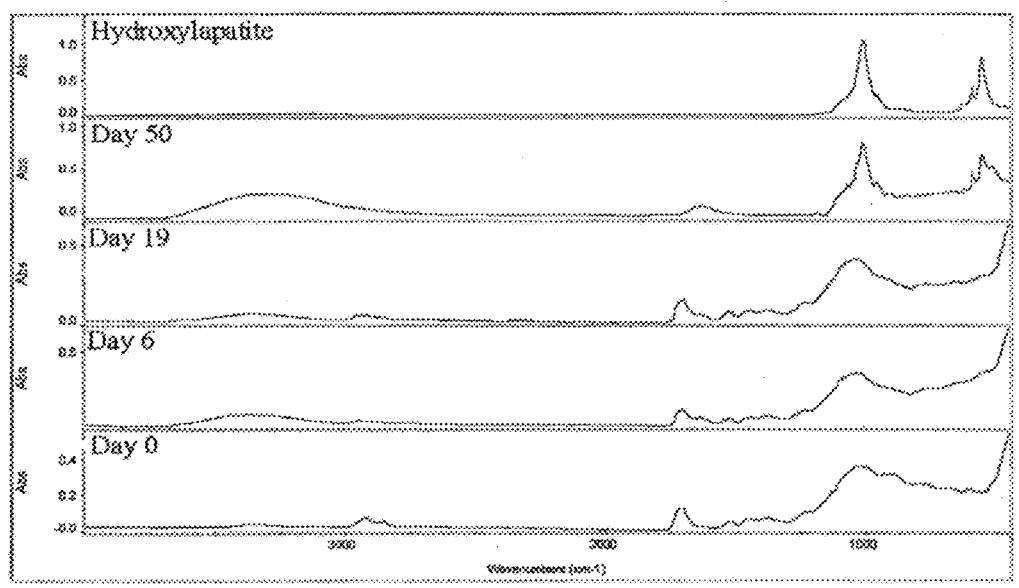
FIG. 54 provides Fourier Transform Infrared Spectroscopy (FTIR) spectrum of the material of the present invention at Day 0, 6, 19 and 50 in comparison to hydroxyapatite.

The Rhakoss FTIR results are shown in FIG. 54. The displayed results show few spectral changes are observed in the early time periods. However, the Day 50 spectrum demonstrates dramatic changes and is very similar to hydroxyapatite. The Day results show the maturity of the calcium phosphate growing on the material. Note the sharpness of the 1014 cm$^{-1}$ band in Day 50 spectra.

The following table outlines the peaks seen on the material in comparison with hydroxyapatite at Day 50 and the molecular assignments:

TABLE 4

FTIR Peaks of the Material of the Present Invention and Hydroxyapatite

ABSORBANCE BAND (cm$^{-1}$)

| HYDROXY-APATITE | RHAKOSS | MOLECULAR ASSIGNMENT |
|---|---|---|
| — | 3292 | O—H and hydrogen bonding from residual water on the composite |
| — | 1632 | Olefin stretch from the composite |
| 1092 | 1075 | Three components of the out of phase |
| 1014 | 1014 | stretch of the phosphate ion |
| 956 | 960 | |
| — | — | Possibly an out of phase deformation band of a carbonate ion resulting from residual SBF salt |
| 602 | 598 | A split bending mode of the phosphate |
| 559 | 556 | ion |

SEM/EDS Results

Figure 55:
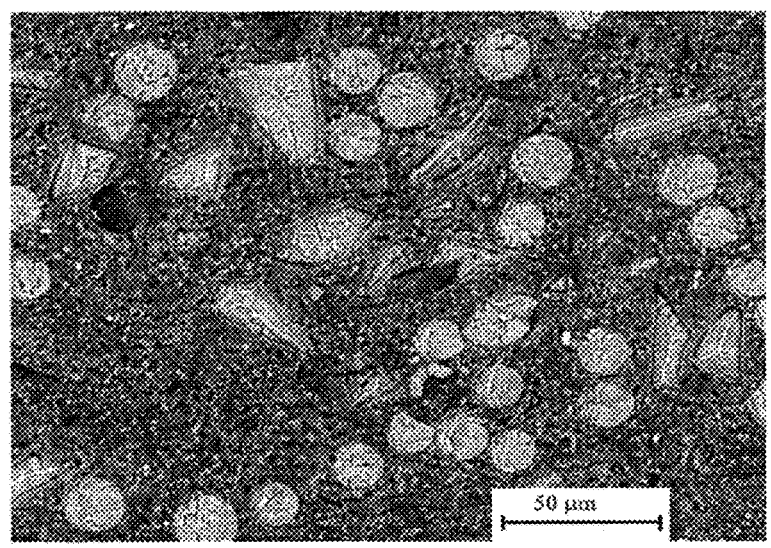
FIG. 55 provides back-scattered electron (BSE) microscopy images of the material of the present invention at Day 0.
Figure 56:
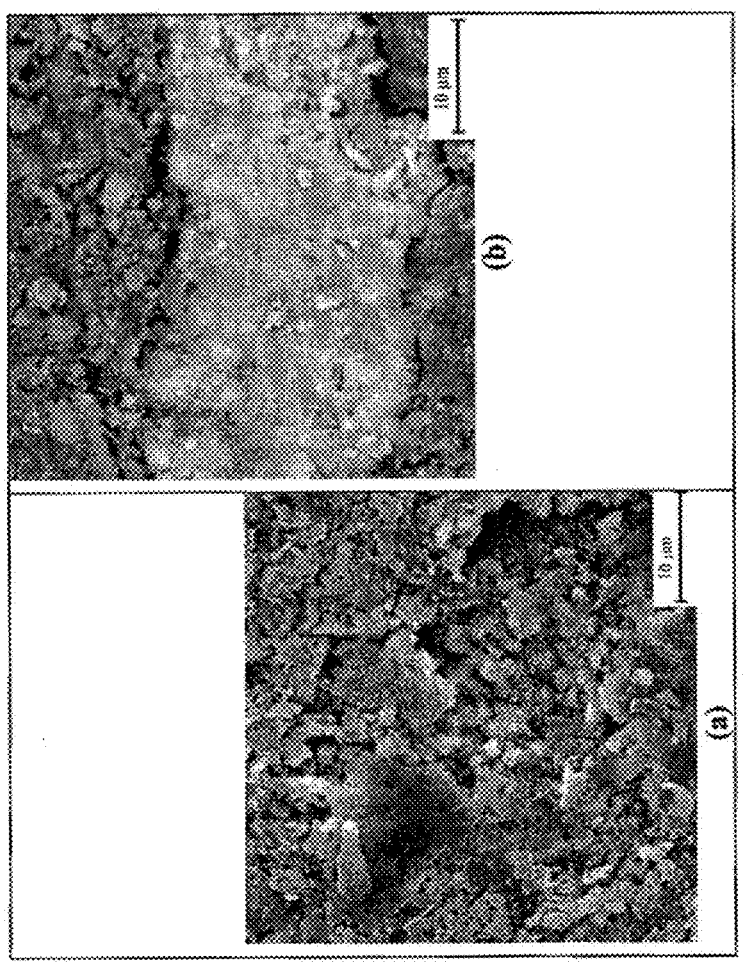
FIG. 56 provides (a) a Scanning Electron Microscopy (SEM) image of a Day 6 sample of the material of the present invention with a layer of calcium phosphate on the surface of a bioactive filler (2500X), (b) SEM of a cross-section of Day 19 with a CaP growth on the surface of a bioactive filler (2500X).

Day 0 back-scattered electron (BSE) image of a cross-section of the material is illustrated in FIG. 55 (500×). The material demonstrated a calcium phosphate crystal (CaP) as early as 6 days as confirmed by EDS analysis. The Day 6 sample showed the growth was limited to a few bioactive fillers. The Day 19 sample showed little differences from the earlier time period as demonstrated in FIG. 56.

Figure 57:
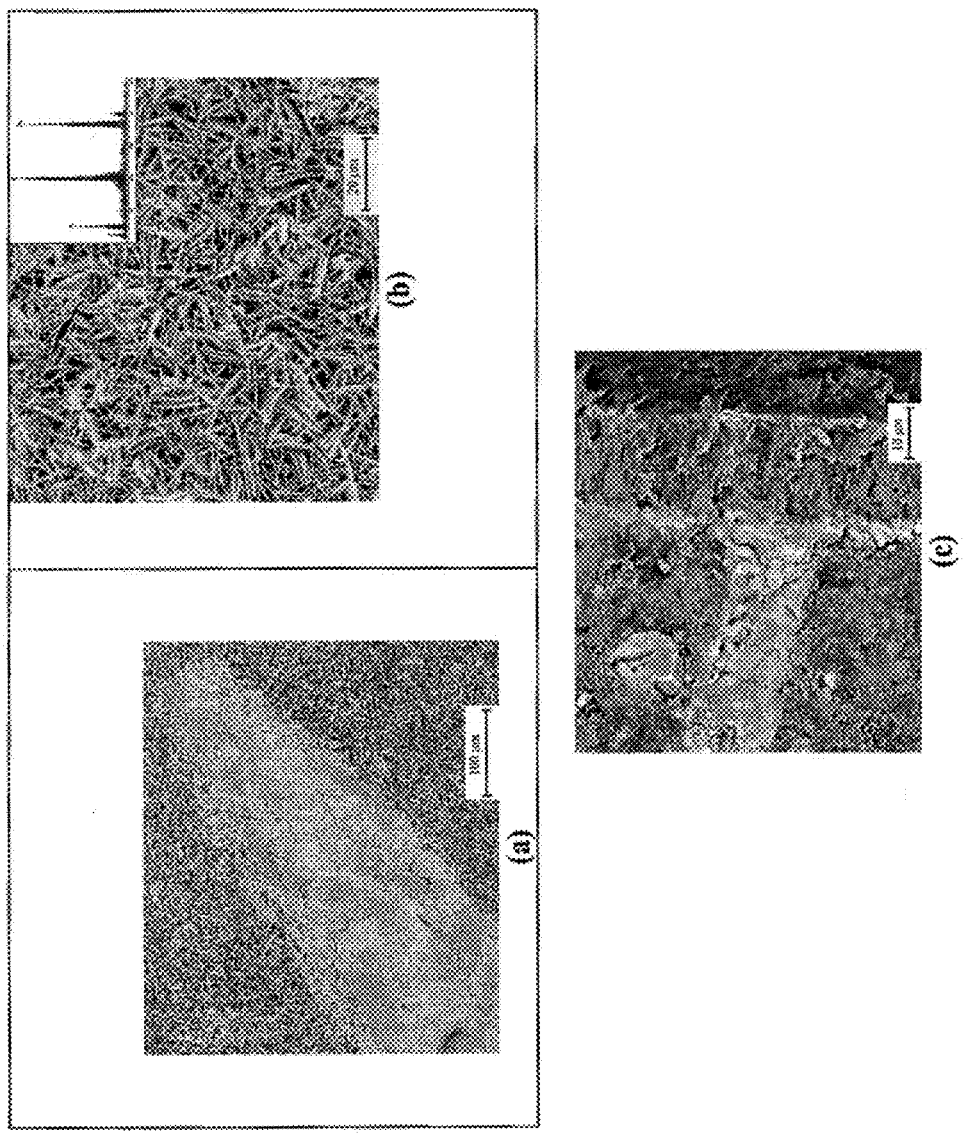
FIG. 57 provides (a) a SEM of a Day 50 sample of the material of the present invention with a layer of CaP on its surface (250X), (b) SEM of a Day 50 sample of the material of the present invention with a thick, dense, needlelike growth of CaP on its surface (1000X) (c) SEM of a cross-section of a Day 50 sample of the material of the present invention, CaP has covered the surface and grown into the bioactive filler (1500X).

By 50 days, the material exhibited a thick, dense CaP layer. Again, this layer covered the entire surface of the composite. The CaP crystals were mature with the appearance of stacked plates. The CaP thickness was measured as approximately 10 microns, and was interdigitated into bioactive fillers at the surface of the composite. FIG. 57 illustrates the CaP crystal on the surface of Rhakoss.

FTIR Conclusions

The early FTIR results showed few spectral changes in the material. Both the Day 6 and Day 19 samples showed the same type of strong organic absorptions as seen in the Day 0 sample.

By Day 50, the material exhibited a thick surface coating of calcium phosphate. Spectra taken at various locations on the material showed only inorganic phosphate absorbencies, and none of the organic bands seen in the previous samples (Day 0, 6, and 19). The depth of penetration for this FTIR technique is 2-microns. This indicates that the thickness of the calcium phosphate growth is at least 2-microns thick.

The Day 50 spectra were compared against several types of calcium phosphates in the User library. The best spectral match for both samples was hydroxyapatite. This close match indicates that hydroxyapatite is the calcium phosphate species growing on the sample surface. The primary hydroxyapatite band seen occurs around 1014 $cm^{-1}$. This band demonstrates a more resolved hydroxyapatite shoulder at 955 $cm^{-1}$, pointing to a mature species.

SEM/EDS Conclusions

At the Day 50 time period, the material appears to have a larger surface coverage of calcium phosphate and a thickness of CaP deposition. The evaluations of the cross-sectioned samples provided an accurate measurement of the CaP thickness. Also, the CaP layer was evaluated for its interdigitation into the composite. Several observations of the CaP migrating into a bioactive E-glass ceramic filler at the surface were noted.

Based on the results presented herein, the material of the present invention can be described as bioactive.

Example 5

Static Compression and Compression Shear of a Cervical Implant

Static compression was performed on 6 spinal implants of the type shown in FIGS. 1-4 with a 7° lordotic angle. All implants withstood at least 8.1 kN of axial load before yielding. In compression-shear testing, the weakest implant type (6 mm extra wide) had a yield of approximately 2.7 kN. Note that human cervical endplates fail at 2.0 kN direct compression.

Example 6

Fatigue Test (Compression) of Cervical Implant

Fatigue testing was performed on 6 spinal implants of the type shown in FIGS. 1-4. All implants successfully withstood 5×10⁶ cycles in 37° C. phosphate buffered saline solution at a 5 Hz loading frequency from −50N to −500N with negligible deformation.

Example 7

Compression Tests of Spinal Implant

An axial compression test was performed on a spinal implant of the type represented in FIGS. 12-14 using an Instron 8516 at a crosshead speed of 1.5 mm/min. Glass-filled Delrin was used as an interface between the implant and the steel fixtures. The Delrin was machined to mate approximately with the angle of the implant design. The implant was designed to include a 5° lordotic angle. Implant failure occurred at approximately 41 kN (about 9000 lbf), approximately 12 times body weight.

An axial compression test was performed on two spinal implants of the type represented in FIGS. 12-14 and one spinal implant of the type represented in FIGS. 1-4 using an Instron 8516 at a crosshead speed of 1.5 mm/min. Polyacetal inserts were machined to match each of the implant's lordotic angle and/or superior and inferior surface contours (e.g., convex top and bottom surfaces). The two implants of the type in FIGS. 12-14 had a maximum implant height of 10 mm and a 5° lordotic angle. Failure occurred at loads of 31 kN and 48.8 kN (10,960 lbf), respectively. The implant of the type in FIGS. 1-4 had a maximum implant height of 10 mm and 7° lordotic angle. Failure occurred at a load of 14.1 kN (3170 lbf).

Example 8

In Situ Testing of a Spinal Implant Tooth Design Study in Foam Bone

Figure 58A:
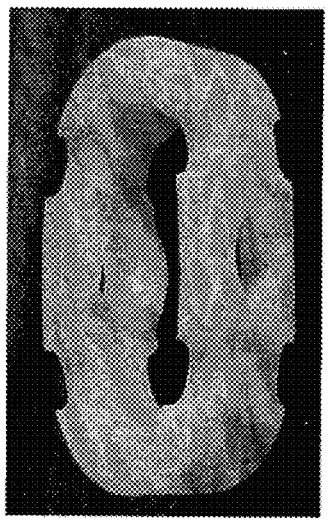
FIG. 58 a, b, c provide implants of the present invention with basic or wave-like tooth profile, pyramid tooth profile, and oblique tooth profile, respectively.
Figure 58B:
Figure 58C:
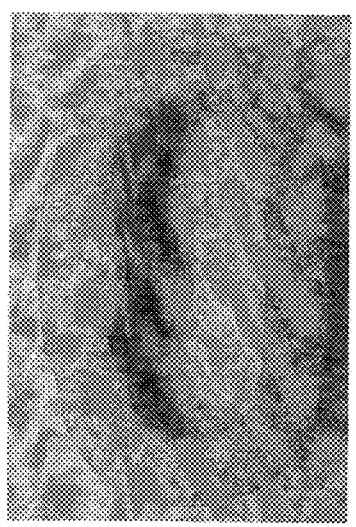

Pull-out testing of various implants was performed in order to evaluate various teeth profiles. Implants of the type shown in FIG. 12 were machined to produce three different tooth design groups (n=5 per group): basic (or wave-like), pyramid and oblique as shown in FIGS. 58*a*, 58*b*, and 58*c*, respectively. The basic implant tooth profile was comprised of parallel rows of continuous teeth (or waves) in line with the long axis of the ellipsoid implant footprint. The pyramid implant tooth profile was comprised of rows of discontinuous pyramid-shaped teeth parallel to the long axis of the ellipsoidal implant footprint. The oblique implant tooth profile was comprised of rows of discontinuous teeth 45° to the long axis of the ellipsoid implant footprint.

For testing, each implant from each group was placed between foam bone squares in an MTS with a preload of 500 N, a value chosen for its relevance to the lumbar spine. Pull-out tests were performed at 0.4 mm/s and load-displacement was recorded. The maximum average pull-out load for the basic design was approximately 1000 N, for the pyramid design was approximately 650N and for the oblique design was approximately 710N. The basic tooth profile appeared to have the greatest pull-out resistance based on this test-in which the pull was in the AP direction.

Example 9

Biocompatibility of a Spinal Implant

Samples of a bioactive spinal implant material were tested for biocompatibility using ISO Guidelines 10993-1, Biological evaluation of medical devices. Under these guidelines and in compliance with U.S. Food and Drug Administration's Good Laboratory Practice Regulation, 21 CPR, Part 58, the material was evaluated for cytotoxicity, sensitization, intracutaneous reactivity, acute toxicity, and genotoxicity. All results were negative and showed the material to be non-cytotoxic, non-allergenic, a non-irritant, non-toxic, non-mutagenic, and non-genotoxic. In addition, material exhibits a degree of polymerization above 98% and analysis revealed organic leachate less than 0.01 ppm/g of monomer elution.

Example 10

In Vivo Implantation of a Spinal Implant

Spinal implants of the type shown in FIGS. 20-22 were implanted in three non-human primates via an anterior interbody spinal surgical technique. Each animal was positioned supine. A standard anterior approach was then used to expose the lumbar spine. A midline incision was made from the umbilicus toward the symphysis pubis. Dissection was carried down through the skin and subcutaneous tissue to expose the midline raphe, which was then incised to enter the abdomen through a transperitoneal approach. Bowel contents were retracted and packed cephalad to protect the bowel and maintain position out of the exposed operative field. At this point, the posterior peritoneal sheath was incised and the great vessels noted. The aorta, vena cava and bifurcation of the left and right common iliac vessels were dissected for free mobility overlying the spine. Middle sacral artery and venous branch were ligated. The vessels were retracted with blunt retractors to allow direct approach to the ventral aspect of the lumbar spine. When the disc space $L_{5-6}$ was identified, a marker probe was placed in position and a lateral x-ray was obtained to confirm the appropriate level of disc. After confirmation of level, the probe was removed and a complete discectomy was performed. The anterior longitudinal ligament was cut away as well as anterior annulus material. The disc was then removed in total.

The bony endplates were cleaned and penetrated so that there was vascular blood flow across the endplate. To facilitate placement of the implants, the disc space was distracted using a distracter instrument. Two bioactive spinal implants of the type shown in FIGS. 20-22 were placed into the distracted disc space, and carefully impacted. A calcium phosphate/bone marrow aspirate (BMA) bone graft material was packed around and between the implants in the disc space.

An interference screw and washer system was placed ventrally to prevent hyperextension of the motion segment and subsequent dislodgment or migration of the implant devices. Following placement, the vessels were allowed to return to their normal position. The posterior peritoneal sheath was then closed with running absorbable suture. The bowel content was allowed to go back into position followed by standard closure of the ventral abdominal wall, the midline fascia, and the skin with subcuticular absorbable suture material.

Radiographs were taken immediately postoperative to verify implant placement and serve as baseline for comparison.

Figure 59:
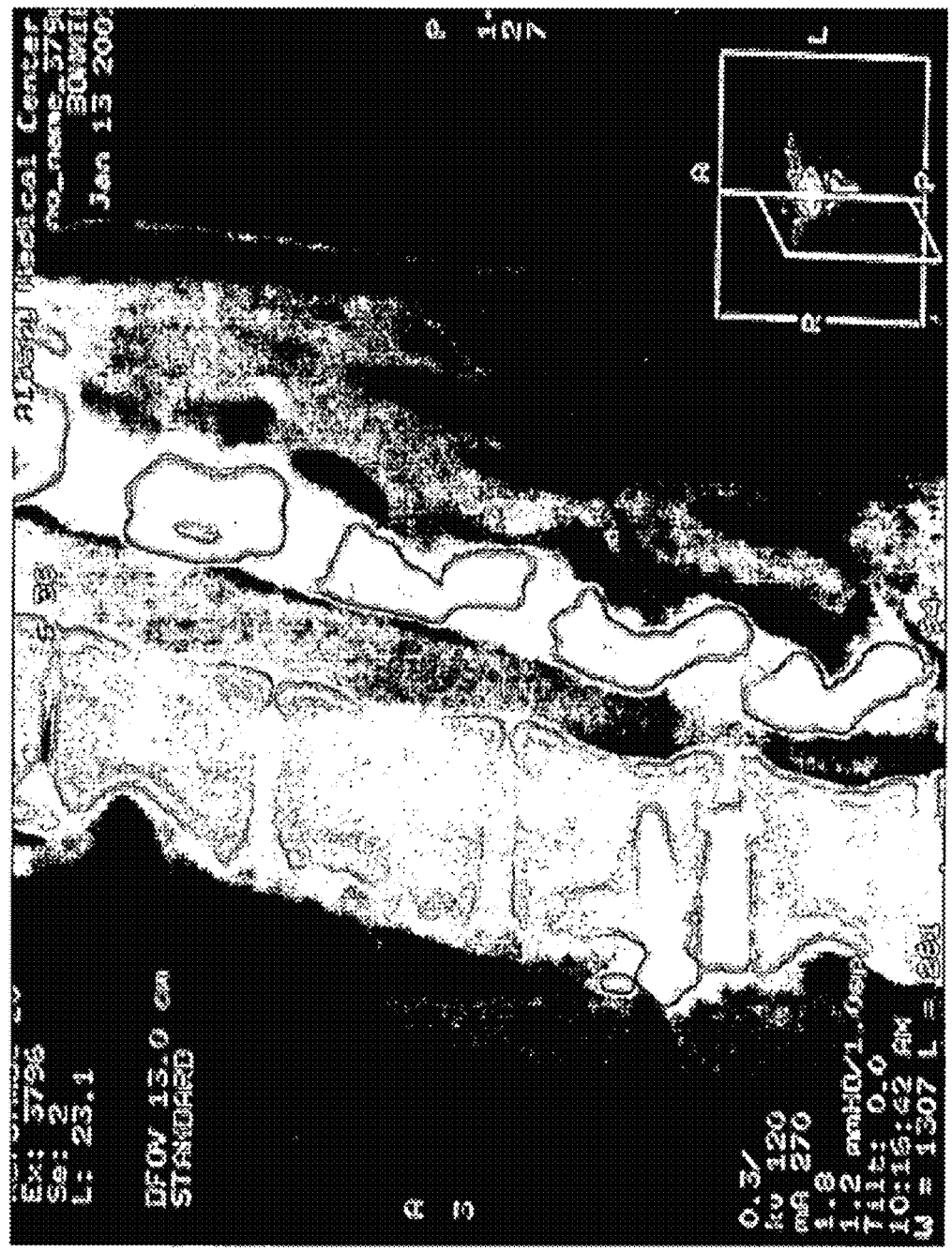
FIG. 59 provides a cat-scan (CT) image of the implant of the present invention implanted in a non-human primate model.
Figure 60:
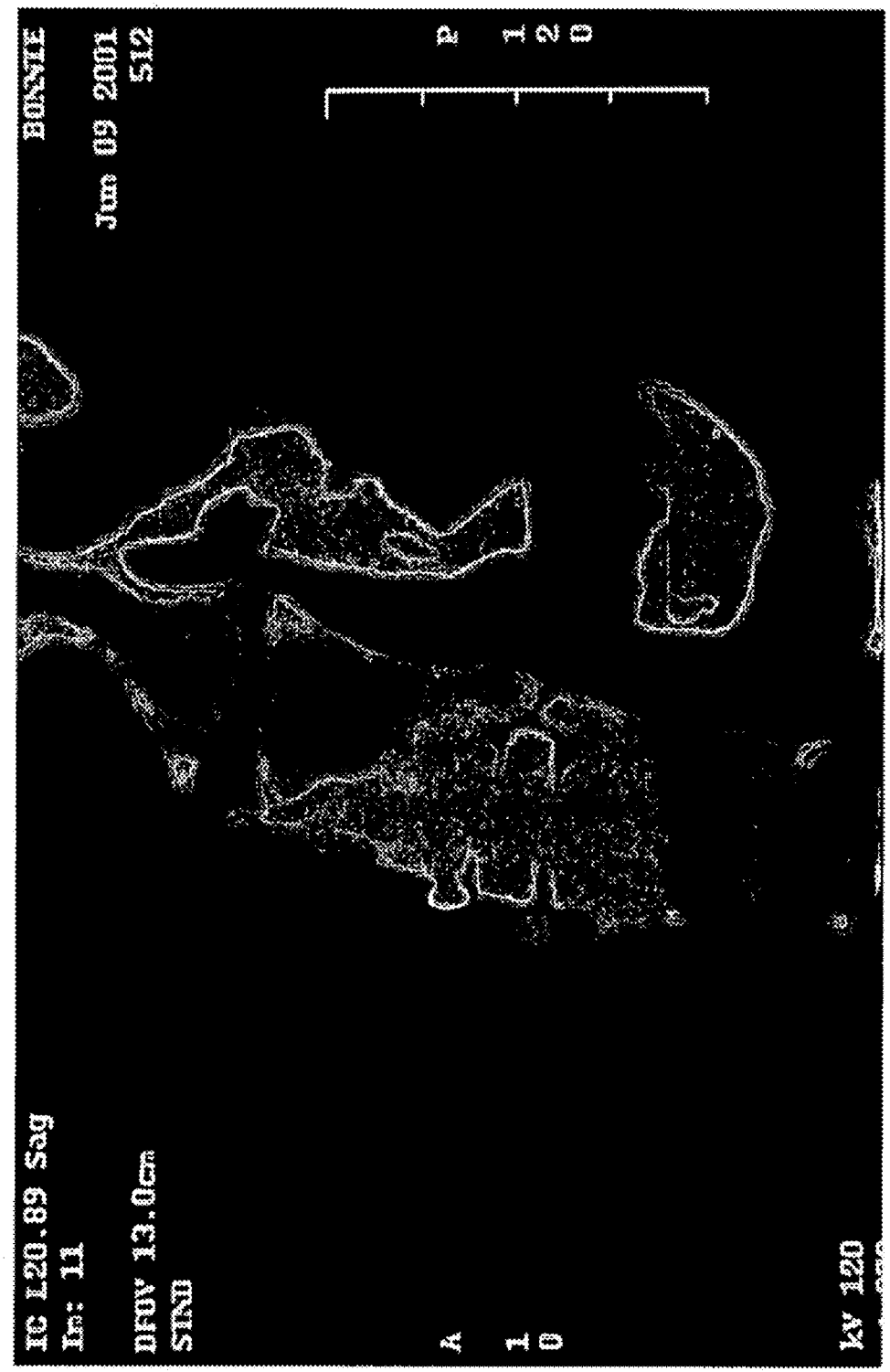
FIG. 60 provides a cat-scan (CT) image of the implant of the present invention implanted in a non-human primate model.

The rate and quality of healing were assessed using radiographs and CT scans taken at 1, 2, 3 and 6 months (FIGS. 59 and 60).

At six months post-operatively, animals were anesthetized (induction by ketamine (10-15 mg/kg BW IM), and, at the discretion of the attending veterinarian, diazepam (10 mg, IM) or acepromazine (1.0 mg/kg, IM) and then euthanized. Following euthanasia, the lumbar spine was retrieved en bloc and the specimens were photographed and observed grossly.

Immediately after sectioning, the excised spinal specimens were inspected for successful fusion and structural integrity of each motion segment. The screw and washer system was removed and the cranial segments were separated from the caudal segments and the specimens photographed and observed grossly.

Specimens without sufficient structural integrity for mechanical testing were immediately prepared for histologic evaluation. Those with sufficient structural integrity were mechanical tested and then prepared for histological evaluation.

All procedures were performed in accordance with Albany Medical College's Internal Animal Care and Use Committee and Quality Assurance Unit.

Results

Bridging bone was found around the implants in all cases. In all cases, the non-destructive flexion testing supported the presence of fusion. There were no Rhakoss particulates noted, and there were no signs of adverse response to the implants. In fact, minimal scar tissue was observed.

Example 11

Manufacture of Spinal Implants

A resin blend (about 20% to about 50% of total implant composition) of urethane dimethacrylate (DUDMA), triethyleneglycol dimethacrylate (TEGDMA), initiator and stabilizer were poured into a Ross planetary mixing system (Hauppauge, N.Y.). The mixer was sealed, mixing was commenced and a vacuum was applied. After the mixer was turned off and the vacuum released, one or more fillers (about 15% to about 80% of the total implant composition) such as E-glass fibers, borosilicate fillers, silica fillers, and combeite fillers were added. Mixing was commenced and a vacuum was drawn upon the addition of each increment of filler. Once all of the fillers were incorporated into the resin, a vacuum was drawn for additional minutes. The mixture was then agitated on a vibrating table with vacuum for about 5 minutes to 60 minutes. The material was extruded into a mold cavity for molding into various bulk geometries.

The mold cavities were heated in a Despatch LFD Series oven and cured at about 40° C. to about 180° C. for a time duration of about 1 hour to 20 hours to form a molded body. Various shaped bodies or implant bodies were then formed.

The materials can also be hot extruded, injection molded, compression molded, or reacted in a mold with a catalyst other than heat.

The cylindrical stock was machined at MedSource (Laconia, N.H.) into spinal implants of the various shapes disclosed herein, having a generally anatomical shape with convex superior and inferior surfaces, lordotic angles and the like.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

The invention claimed is:
1. A spinal implant system comprising:
 a body comprising:
  an anterior side, a posterior side opposing the anterior side, and a pair of opposing side walls, the anterior side, the posterior side, and side walls joining at points that generally define, in transverse cross section, a trapezoid said sides being generally outwardly curved;
  a top surface and a bottom surface, each of the top and bottom surfaces including plural projections for enhancing interaction with a synthetic or natural vertebral body; and
  a handling feature comprising a pair of elongated side recesses and a front recess, the handling feature facilitating handling and insertion of the spinal implant into an intervertebral space, wherein the elongated recesses each comprise an opening; and a manipulator comprising a first arm and a second arm, the first and second arms being engageable with the elongated side recesses.

2. The spinal implant system of claim 1 wherein the generally outwardly curved sides are convex as viewed from outside said spinal implant.

3. The spinal implant system of claim 1 wherein the body forms a lordotic angle of about −20 degrees to about +20 degrees.

4. The spinal implant system of claim 1 wherein the height of the anterior side is greater than a height of the posterior side.

5. The spinal implant system of claim 1 wherein the body substantially forms a trapezoidal shape in longitudinal cross-section.

6. The spinal implant system of claim 1 wherein the projections are substantially uniform, upwardly protruding ribs.

7. The spinal implant system of claim 1 wherein the projections are randomly disposed.

8. The spinal implant system of claim 1, wherein the first arm includes a first projection and the second arm includes a second projection, the first and second projections being configured for insertion into a respective one of the openings of the elongated recesses.

9. A spinal implant system comprising:
 a body comprising a bioactive substance, further comprising:
 sides that are generally outwardly curved in transverse cross-section;
 a top surface and a bottom surface, both surfaces coupled with the sides, each one of the top surface and the bottom surface forming plural projections for enhancing interaction with a synthetic or natural vertebral body;
 a major recess formed in the body in communication with at least one of the top surface and the bottom surface; and
 a handling feature comprising a pair of elongated side recesses and a front recess, the handling feature facilitating handling and insertion of the spinal implant into an intervertebral space, wherein the elongated recesses each comprise an opening; and
 a manipulator comprising a first arm and a second arm, the first and second arms being engageable with the elongated side recesses.

10. The spinal implant system of claim 9 wherein the body forms a lordotic angle of about −20 degrees to about +20 degrees.

11. The spinal implant system of claim 9 wherein the height of the anterior side is greater than the height of the posterior side.

12. The spinal implant system of claim 9 wherein the body substantially forms a trapezoidal shape in longitudinal cross-section.

13. The spinal implant system of claim 9 wherein the projections are substantially uniform, upwardly protruding ribs.

14. The spinal implant system of claim 9, wherein the first arm includes a first projection and the second arm includes a second projection, the first and second projections being configured for insertion into a respective one of the openings of the elongated recesses.

15. A spinal implant system comprising:
 a body comprising a bioactive substance, further comprising:
 an anterior side, a posterior side opposing the anterior side, and a pair of opposing sidewalls, said sidewalls being generally outwardly curved;
 a top surface and a bottom surface, both surfaces coupled with the sides, each one of the top surface and the bottom surface forming plural projections for enhancing interaction with a synthetic or natural vertebral body;
 at least one major recess formed in the body in communication with at least one of the top surface and the bottom surface;
 a handling feature comprising recesses in the top and bottom surfaces in communication with the anterior and posterior sides and at least one recess in the anterior or sidewalls for receiving an impaction tool, the handling feature facilitating handling and insertion of the spinal implant into an intervertebral space; and
 a fastening feature comprising a first through-aperture angled through the anterior side, such that a fastener inserted into the first through-aperture is directed into a first synthetic or natural vertebral body.

16. The spinal implant system of claim 15 wherein the anterior and posterior sides are parallel.

17. The spinal implant system of claim 15 wherein the anterior and posterior sides are generally outwardly curved.

18. The spinal implant system of claim 15 wherein the lordotic angle ranges from about −20 degrees to about +20 degrees.

19. The spinal implant system of claim 15 wherein the height of the anterior side is greater than a height of the posterior side.

20. The spinal implant system of claim 15 wherein the major recess forms a longitudinal through-aperture.

21. The spinal implant system of claim 15, wherein the fastening feature further comprises a second through-aperture angled through the anterior side, such that a fastener inserted into the second through-aperture is directed into a second synthetic or natural vertebral body.

22. The spinal implant system of claim 15, wherein the at least one recess in the anterior or sidewalls has a geometry that matches a geometry of a portion of the impaction tool, such that upon engagement of the portion of the impaction tool with the at least one recess, the implant is rotationally fixed relative to the impaction tool.

* * * * *